US006025194A

United States Patent [19]
Funk

[11] Patent Number: 6,025,194
[45] Date of Patent: Feb. 15, 2000

[54] NUCLEIC ACID SEQUENCE OF SENESCENCE ASSSOCIATED GENE

[75] Inventor: Walter Funk, Hayward, Calif.

[73] Assignee: Geron Corporation, Menlo Park, Calif.

[21] Appl. No.: 08/974,180

[22] Filed: Nov. 19, 1997

[51] Int. Cl.$^7$ .......................... C07H 21/04; C12N 15/63; C12N 15/85; C12N 15/11
[52] U.S. Cl. .................... 435/320.1; 536/23.1; 536/23.5; 536/24.1; 435/320.1; 435/325
[58] Field of Search .................................. 536/23.5, 23.1, 536/24.1; 435/320.1, 325

[56] References Cited

U.S. PATENT DOCUMENTS 5,580,726 12/1996 Villeponteau et al. ...................... 436/6

FOREIGN PATENT DOCUMENTS

WO 96/13610 5/1996 WIPO .............................. C12Q 1/68

OTHER PUBLICATIONS

Hillier et al GenBank Acc. No: N98695 Publically Available Apr. 10, 1996.

Marra et al GenBank Acc. No: AA388297 Publically Available Apr. 23, 1997.

Matsubara et al WO 9514772–A1 (Sequence Alignment Provided. The Actual Reference is over 2000 pages—will be Provided if Required & Requested by Applicant. 1995.

Li et al.; "Expression of Human Dopamine β–hydroxylase in Drosophila Schneider 2 Cells"; 1995; No. 313, pp. 57–64.

Berkowitz et al.; "Effects of the Novel Dopamine β–Hydroxylase Inhibitor SK&F 102698 on Catecholamnes and Blood Pressure in Spontaeously Hypertensive Rats"; *The Journal of Pharmacology and Experimental Therapeutics;* 1988; vol. 245, No. 3, pp. 850–857.

Robertson et al.; "Dopamine β–Hydroxylase Deficieny—A Genetic Disorder of Cardiovascular Regulation"; *Hypertension;* Jul. 1991; vol. 18, No. 1, pp. 1–8.

Ohlstein, et al.; "Cardiovascular Effects of a New Potent Dopamine β–Hydroxylase Inhibitor in Spontaneously Hypertensive Rats"; *The Journal of Pharmacology and Exprimental Therapeutics;* 1987; vol. 241, No. 2, pp. 554–559.

Linskens et al.; "Cataloging altered gene expression in young and senescent cells using enhanced differential display"; *Nucleic Acids Research;* 1995; vol. 23, No. 16:3244–3251 (1995).

Frigon, et al.; "Human Plasma Dopamine β–Hydroxylase"; *The Journal of Biological Chemistry;* Oct. 10, 1978; vol. 253, No. 19, pp. 6780–6786.

*Primary Examiner*—Sheela Huff
*Assistant Examiner*—Geetha P. Bansal
*Attorney, Agent, or Firm*—David J. Earp; Kevin Kaster

[57] ABSTRACT

Human gene GC6 is expressed more abundantly in senescent cells than young cells. Isolated, purified, and recombinant nucleic acids and proteins corresponding to the human GC6 gene and its mRNA and protein products, as well as peptides and antibodies corresponding to the GC6 protein can be used to identify senescent cells, distinguish between senescent and young cells, identify agents that alter senescent gene expression generally and GC6 expression specifically; such agents as well as GC6 gene and gene products and products corresponding thereto can be used to prevent and treat diseases and conditions relating to cell senescence.

10 Claims, No Drawings

NUCLEIC ACID SEQUENCE OF SENESCENCE ASSSOCIATED GENE

BACKGROUND OF THE INVENTION

1. Field of the Invention

The present invention relates to cellular senescence, markers of cellular senescence, and methods and reagents for identifying senescent cells and agents that alter senescent gene expression expression of cells, as well as for detecting, diagnosing, preventing, and treating senescence-related diseases and conditions in humans and other mammals. The invention provides oligonucleotide probes and primers, polynucleotide plasmids or vectors, peptides, proteins, and antibodies relating to genes and gene products associated with the senescence in mammalian cells. The invention thus relates to the fields of molecular biology, chemistry, gerontology, pharmacology, oncology, and screening and diagnostic technology.

2. Description of Related Disclosures

Somatic cells have a finite replicative capacity (Hayflick and Moorhead, 1961, *Exp. Cell Res.* 25:585–621; Hayflick, 1965, *Exp. Cell Res.* 37:614–636; and Hayflick, 1970, *Exp. Geront.* 5: 291–303). This process is a major etiological factor in aging and age-related disease (Goldstein, 1990, *Science* 249:1129–1133; Stanulis-Praeger, 1987, *Mech. Aging Dev.* 38:1–48; and Walton, 1982, *Mech. Aging Dev.* 19:217–244). As cells undergo replicative senescence in vitro and in vivo, cells not only lose the ability to divide in response to growth stimuli, but also exhibit significant deleterious changes in the pattern of gene expression (West, 1994, *Arch. Derm.* 130:87–95). As an individual grows older, senescent cells make up an increasing percentage of the cells present in the tissues of the aging individual. The altered pattern of gene expression exhibited by senescent cells contributes significantly to age-related pathologies. Reversal of, or a delay in the onset of, senescence provides an effective therapy for diseases in which replicative senescence is a factor.

One fundamental cause of cellular senescence is the progressive loss of telomeric DNA in somatic cells that lack the enzyme, telomerase (Nakamura et al., Aug. 15, 1997, *Science* 277:955 et seq.). This arrest appears to be mediated by a DNA checkpoint by which the cell recognizes the shortened telomere as damaged DNA and causes cell cycle arrest similar to that observed in normal cells after DNA damage.

As cells progress to a senescent state, the cells exhibit an elongation of the G1 phase of the cell cycle, leading to a longer cell time of cycle transit. As the progression from a mitotically active to a senescent state continues, cells fail to respond to mitotic signals and remain in G1. This inability of senescent cells to enter the cell cycle represents a significant difference between young and old cells. Unlike old cells, young cells become quiescent entering G0 but can be subsequently induced to reenter the cell cycle and divide. However, senescent cells, while remaining viable and metabolically active, become refractile to entering the cell cycle.

A characteristic of replicative senescence is that changes in the pattern of gene expression can be observed as the cell progresses through its replicative lifespan. These changes are reflected in a decrease in the expression of "young-specific" genes and an increase in the expression of "old-specific" genes. Together, these young- and old-specific genes are referred to herein as "senescence-specific" genes, where a senescence-specific gene is any gene for which the product of the gene is differentially expressed between young quiescent cells and senescent cells. Not only do these changes affect the structure and function of the senescent cell, but also such changes can influence the physiology of surrounding cells and the tissue matrix by altering the extracellular environment, i.e., in a paracrine fashion through the release of different proteins or through changes in cell-cell interactions. Several senescence-specific genes have been described (Linskens et al., PCT No. WO 96/13610, published May 9, 1996 and incorporated herein by reference).

Changes in mRNA levels and cellular content of specific proteins provides evidence of a senescence-specific program of gene expression, leading to a differentiated genotypic and phenotypic state (Linskens et al., supra). Changes in steady state mRNA levels can translate into changes in protein expression and levels, as the rate and extent of mRNA translation represents an additional mechanism of controlling gene expression at the protein level. Cell structure and function also change when gene expression at the protein level changes.

Thus, as an individual grows older and the percentage of senescent cells in the aging individual's tissues increases, the resultant altered pattern of gene expression can contribute significantly to the pathophysiology of age-related changes in specific tissues (e.g., skin) and age related diseases. There is a need for therapeutic agents and treatments targetting the underlying biology of aging and age-related diseases, particularly the biology relating to the fundamental changes in gene expression that occur with cell senescence and lead to the development of age-related disease. The present invention helps meet that need by providing new methods and agents for discriminating between young and senescent cells, for identifying agents that modulate senescent gene expression, and for treating diseases induced or exacerbated by cellular senescence.

SUMMARY OF THE INVENTION

The present invention provides methods and reagents for identifying compounds and compositions that alter senescent gene expression and for identifying or distinguishing senescent cells from non-senescent cells, as well as methods, reagents, and compositions that are specific and effective for treating conditions and diseases associated with cellular senescence. In particular, the invention provides methods, reagents, and compounds relating to a novel senescence-related gene referred to herein as GC6. The methods, reagents, and compositions of the invention can be applied to a wide variety of cell types.

The invention provides synthetic and recombinant oligonucleotides and nucleic acids in a variety of forms, i.e., isolatable, isolated, purified, or substantially pure, and for a variety of purposes, i.e., as probes, primers, polynucleotides, and plasmid or vector nucleic acids. Thus, the invention provides recombinant or synthetic nucleic acids comprising at least about 8 to 10 to 15 to 25 to 100 or more contiguous nucleotides substantially identical or complementary in sequence to a contiguous nucleotide sequence of the human GC6 gene.

Nucleic acids and polynucleotides comprising such sequences can be isolated from plasmid pCIneoGC6 (available from the American Type Culture Collection, ATCC, under accession number ATCC 209608; an ~3 kb XhoI-XbaI restriction fragment of this plasmid comprises the complete coding sequence of the GC6 gene, which encodes a protein, designated pGC6, present in human cells. Homologues of the pGC6 protein and the GC6 gene are present in other mammalian cells and are also provided by the invention.

The recombinant expression vectors of the invention typically comprise at least about 25 to 100 to 1000 or more, up to the full length coding or open reading frame sequence, contiguous nucleotides identical or complementary in sequence to a contiguous nucleotide sequence of the human GC6 gene. In other embodiments, the invention provides recombinant expression vectors that encode the promoter of the GC6 gene operably linked to the coding sequence of pGC6 or to a coding sequence for a reporter molecule, such as beta-galactosidase or secreted alkaline phosphatase, or other coding sequence not naturally associated with the GC6 gene promoter. The GC6 gene promoter can be isolated from libraries of human genomic DNA by probing with probes of the invention and identifying clones with inserts including all or a portion of the ORF of the gene and 5' upstream sequences or with primers of the invention using techniques such as 5'-RACE.

The expression vectors have many useful applications, including for production of the protein, pGC6, peptides derived from the protein, oligonucleotides and nucleic acids identical or complementary to at least a portion of the pGC6 coding sequence or other regions of the GC6 gene, or heterologous polynucleotides or polypeptides. The expression vectors of the invention can also be used in therapeutic methods of the invention for altering senescent gene expression, either to upregulate, down-regulate, or inhibit expression of pGC6 or mRNA transcribed from the GC6 gene in a target cell or tissue. Such expression vectors also include those that encode variants or "muteins" of pGC6 proteins, i.e., express proteins that differ from pGC6 by deletion, substitution, and/or addition of one or more amino acids, as well as those that encode useful nucleic acids, such as antisense, ribozyme, and triple-helix forming nucleic acids that target GC6 gene products, e.g., mRNA or pGC6. The recombinant expression vectors of the invention can be employed in recombinant host cells, cell free transcription and/or translation system, and in intact mammals, including humans.

The recombinant host cells and vectors of the invention are also useful in screens to identify agents that prevent or modulate senescent gene expression. For example, the vectors can be used to produce recombinant pGC6 that is employed in assays to identify agents that inhibit its function in cells. Also, vectors that employ the promoter of the GC6 gene to drive expression of a reporter molecule are useful in screens to identify agents that modulate the activity of the promoter of the GC6 gene.

As indicated above, the present invention also provides peptides and proteins corresponding to all or part of pGC6. While such compounds can be produced by recombinant methods using the vectors, host cells, and translation systems of the invention, the peptide and protein compounds of the invention, similarly to the oligonuclcotides and vectors of the invention, can also be produced by synthetic means. In particular, the invention provides synthetic and recombinant peptides and proteins comprising at least about 6 to 10 to 15 to 25 to 100 or more, up to the full length of pGC6, contiguous amino acids identical or substantially identical in sequence to an amino acid sequence encoded by the GC6 gene. The present invention also provides methods for isolating the proteins and peptides of the invention in isolated or purified form from host cells and translation systems expressing recombinant pGC6.

The proteins and peptides of the invention can be used to generate antibodies specific for pGC6 and for particular epitopes specific to this protein. Thus, the invention provides polyclonal and monoclonal antibodies that specifically bind to pGC6. These antibodies can in turn be used to isolate pGC6 from normal or recombinant cells and so are useful in methods of the invention to purify the protein as well as other proteins associated therewith. These antibodies also have important application in the detection of cells comprising pGC6 in complex mixtures of cells. Such detection methods have application in screening, diagnosing, and monitoring diseases and other conditions associated with aging, such as hypertension, particularly as pGC6 exhibits significant homology to dopamine beta-hydroxylase (DBH). See Berkowitz et al., 1988, *J. Pharm. Exp. Ther.* 245(3) :850–7; Frigon and Stone, Oct. 10, 1978, *J. Biol. Chem.* 253(19):6780–6786; Ohlstein et al., 1987, *J. Pharm. Exp. Ther.* 241(2):554–9; Robertson et al., July 1991, *Hypertension* 18(1): 1–8; and Li et al., 1995, *Biochem J.*: 313:57–64.

The present invention provides methods for identifying agents, i.e., test compounds and compositions, that can prevent or alter the pattern of senescent gene expression in mammalian, especially human cells, which method comprises: (a) contacting said cells with an agent; (b) measuring an amount of a GC6 gene product in said treated cells to obtain a measured amount, i.e., by using a GC6 gene product-specific nucleic acid primer or probe or antibody or assay of the invention; (c) comparing said measured amount with a control amount of said GC6 gene product determined by measuring said GC6 gene product in said cells in absence of said agent; and (d) identifying as an agent that can alter said pattern of senescent gene expression in cells as those agents that produce an increased or decreased measured amount relative to said control amount.

Any of a variety of GC6 gene products can be used in the method, for example, one can measure an amount of GC6-specific mRNA or pGC6 or one can measure an activity of pGC6. In addition, the assay or screen can be conducted in combination with analysis of the affect of the agent on other known senescent specific markers, such as, for example, beta-galactosidase, collagenase, interferon gamma, collagen I, collagen III, elastase, elastin, TIMP3, or IL-Ia, autofluorescence, acridine-orange fluorescence, and telomere length. A preferred method involves the measurement of a combination of markers including a GC6 gene product.

The present invention also provides methods for identifying or distinguishing senescent cells from young (also referred to as quiescent, presenescent, or non-senescent) cells in tissues or in culture. In general, a young cell produces lower amounts of GC6 gene products than a senescent cell. Thus, the present invention allows one to identify young cells, to identify senescent cells, to determine where in the development from young to fully senescent a cell or tissue sample is located, to identify the proportion or relative amounts of young and senescent cells in a sample, and to distinguish young from senescent cells. One such method comprises contacting a GC6 gene product within a cell or tissue with an agent that binds specifically to said GC6 gene product under conditions such that said agent and said GC6 gene product bind to one another; determining whether specific binding has occurred; and correlating the presence of senescent and non-senescent cells with occurrence of binding.

The methods of the invention are broadly applicable to the identification of senescent cells and alteration of senescent gene expression in cells and tissues of mammals. The methods are especially useful and applicable to the identification of senescent cells and alteration of senescent gene expression in samples of biological material obtained from humans. Such samples will contain cells or cellular materials and will typically be obtained from humans for the purposes of determining agents that alter senescence gen expression and diagnosing or treating diseases or disease conditions induced or exacerbated by cell senescence. These and other aspects of the invention are described in more detail below.

DETAILED DESCRIPTION OF THE INVENTION

To facilitate understanding of the invention, the disclosure of the invention is organized in sections as follows. First, a glossary is provided to define terms and phrases used throughout the specification and claims. The next section describes useful reagents and compounds of the invention, which include oligonucleotides, recombinant expression vectors, peptides and proteins, as well as methods employing the same. The next section describes methods of the invention for identifying compounds that alter senescent gene expression expression; such compounds are referred to as modulators. The following section describes methods for identifying, or distinguishing between, senescent and non-senescent cells, followed by a description of the diagnostic and therapeutic methods and applications of the invention, as well as compounds and compositions effective for treating conditions and diseases associated with senescent gene expression and aging by modulating expression levels of senescent specific genes. The specification concludes with a number of examples relevant to the invention and its practice and application.

I. Glossary

Unless otherwise specified, all technical and scientific terms used herein have the same meaning as commonly understood by those of ordinary skill in the art to which the invention pertains. Commonly used terms herein for purposes of describing how to make and use present invention are defined below.

"Affinity purification" refers to the purification or molecular separation of a compound from one or more, typically many more, compounds and compositions with which the compound desired to be purified is associated by binding to an agent that specifically binds the desired compound relative to the other compounds and compositions in the unpurified mixture. Typically, such binding is reversible, and the binding agent or compound is a biomolecule, i.e., an oligonucleotide or antibody. For example, one type of binding agent is an "affinity oligonucleotide" (i.e., an antisense oligonucleotide is an affinity oligonucleotide related to nucleic acids that comprise a complementary sequence of nucleotides). After binding of the affinity purification reagent to the compound to be purified, one typically, but not always, displaces the compound from the binding agent in a step referred to as elution. For example, one can use a "displacement oligonucleotide" to elute a desired nucleic acid from its specific binding agent.

An "agent" or "compound" refers to a chemical compound or composition, including, but not limited to, organic molecules, polynucleotides, proteins, peptides, and the like, a mixture of chemical compounds, an array of spatially localized compounds (e.g., a peptide array, polynucleotide array, and/or other molecular array; where "array" refers to a collection of different molecular species, which can be immobilized on a surface), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues.

An "antibody" refers to a naturally occurring or recombinant polypeptide or associated polypeptides and proteins that specifically bind to or "recognize" an analyte or "antigen". Naturally occurring antibodies are encoded by immunoglobulin genes, but a wide variety of antibodies and antibody-like molecules and fragments thereof, are available through recombinant DNA technology. Immunoglobulin genes include the kappa, lambda, alpha, gamma, delta, epsilon and mu constant region genes, as well as myriad immunoglobulin variable region genes. An antibody can exist as an intact immunoglobulin or as any one of a number of well characterized fragments, e.g., Fab' and F(ab)'2 fragments, and such antibodies can be produced by various means, including, as noted above, recombinant DNA methodology and from naturally occurring antibodies; for example, antibody fragments can be produced by digestion with various peptidases. See also, Harlow and Lane Antibodies, A Laboratory Manual, Cold Spring Harbor Publications, New York (1988), incorporated herein by reference.

An "antigenic determinant" or "epitope" refers to a particular chemical group or groups of an antigen that binds to a particular antibody and confers antigenic specificity. When a protein or fragment of a protein is used to immunize a host animal, numerous regions of the protein may induce the production of antibodies that bind specifically to a given region or three-dimensional structure on the peptide or protein; these regions or structures are referred to as antigenic determinants. An antigenic determinant may compete with the intact antigen (i.e., the immunogen used to elicit the immune response) for binding to an antibody.

"Antisense" refers to oligonuleotides or polynucleotides comprising sequences of nucleotides that are complementary to a sequence in another oligonucleotide or polynucleotide (e.g., mRNA). Antisense oligonucleotides can be produced by a variety of methods, as is commonly known in the art. For example, but not limitation, antisense RNA can be synthesized by splicing the gene(s) or coding sequence of a gene of interest in a reverse orientation, relative to its orientation in nature, to a promoter that directs the synthesis of the antisense nucleic acid. An antisense oligonucleotide can bind to a complementary sequence in its "target" nucleic acid, such as a naturally occurring mRNA produced by a cell, via hydrogen bonding to form a duplex or double-stranded nucleic acid. Such duplex formation can reduce or completely inhibit the translation of proteins from the target mRNA or, if the antisense oligonucleotide is bound to DNA in a gene, transcription of that gene. In this manner, alteration or modulation of gene expression can be achieved.

"Biologically active" refers to compounds, such as, for example but without limitation, organic molecules such as drugs and synthetic or recombinant nucleic acids, peptides, proteins or the like, that exhibit an activity, i.e., inhibit or increase transcription or translation of a nucleic acid or activity of an enzyme or property of a structural molecule, in a cell extract, cell, tissue, organism or animal.

A "cDNA" refers to a deoxyribonucleic acid produced by reverse-transcription and for double-stranded cDNA second-strand synthesis of mRNA or other RNA produced by a gene, as well as recombinant or synthetic replicas or derivatives thereof.

"Complementary" or "complementarity" refers to the well known property of nucleic acids arising out of hydrogen bonding or "base-pairing" between nucleotides to form double-stranded complexes. A first oligonucleotide or polynucleotide is complementary to or has complementarity with a second oligonucleotide or polynucleotide if the sequence of nucleotides in the first and second molecules allows them to form a stable duplex arising out of hydrogen bonding between A (adenosine) residues in one with T (thymidine) residues in the other and C (cytosine) residues in one with G (guanosine) residues in the other. By way of illustration only (because typically longer sequences of complementarity are required) the oligonucleotide having sequence "5'-A-G-T" is complementary to an oligonucleotide having the sequence "5'-T-C-A." Complementarity may be "partial," in which only some of the nucleic acid bases in an oligonucleotide are hydrogen bonded to bases in the other oligonucleotide, or "complete," in which all of the nucleic acids in one of the oligonucleotides are hydrogen bonded to a contiguous sequence of nucleotides in the other. The formation of a duplex nucleic acid from two single-stranded nucleic acids (such as an oligonucleotide probe to a target mRNA) is often referred to as "hybridization." Hybridization can be carried out or prevented by a variety of conditions, the cumulative effect of which is often referred to as "the stringency" of hybridization. Factors and conditions such as the length and composition (DNA, RNA, base composition) of the probe and target, the concentration of salts and other components (e.g., the presence or absence of formamide, dextran sulfate, polyethylene glycol), temperature, solvent, and time of hybridization all contribute to the stringency of hybridization, as is well known in the art. Conditions of low stringency allow for hybridization of nucleic acids of partial complementarity, while conditions of high stringency can select for complete hybridization of a probe to a target nucleic acid. Thus, "stringent conditions" or "stringency" can refer to temperature and ionic conditions used in nucleic acid hybridization. Generally, stringent conditions are selected to be about 5 to 20 degrees C. lower than the thermal melting point (Tm) for the specific sequence at a defined ionic strength and pH. The Tm is the temperature (under defined ionic strength and pH) at which half of a population of complementary double-stranded nucleic acid molecules becomes dissociated into single stranded molecules. The equation for calculating the Tm of nucleic acids is well known in the art. See, e.g., Anderson and Young, Quantitative Filter Hybridization, in Nucleic Acid Hybridization (1985).

"Encoding" refers to an inherent property of a sequence of nucleotides in a nucleic acid, such as a gene in a chromosome or an mRNA, to serve as a template for synthesis of other polymers and macromolecules in biological processes having a defined sequence of nucleotides (rRNA, tRNA, other RNA molecules) or amino acids (peptides and proteins). For example, a gene encodes a protein if transcription and translation of mRNA produced by that gene produces the protein in a cell or other biological system. Both the coding strand of the gene, the strand having the nucleotide sequence identical to the sequence of nucleotides in the mRNA produced by the gene, and the complemenatary, non-coding strand of the gene can be referred to as encoding the protein or other product of that gene. Due to the degeneracy of the genetic code, a variety of different nucleic acid sequences can encode the same peptide or protein. Also, genes and mRNA of mammals (and other organisms) can include non-coding sequences called introns but still be referred to herein as "encoding" a peptide or protein.

An "expression control sequence" refers to a nucleotide sequence in a nucleic acid that regulates the expression (transcription and/or translation) of a nucleotide sequence operatively linked thereto. Expression control sequences can include, for example and without limitation, sequences of a promoter, enhancer, and transcription terminator, all of which can be involved in transcription of DNA to form RNA, and a ribosome-binding site, start codon (i.e., ATG), splicing signal for an intron/exon, and a stop codon, all of which can be involved in translation of RNA to form a protein.

An "immunoassay" refers to an assay in which an antibody or fragment thereof is used to detect an analyte.

"Immunologically active" refers to the ability of natural, recombinant, or synthetic protein or peptide (or a nucleic acid) to induce an immune response in an animal.

A "label" refers to a compound or composition that facilitates detection of a compound or composition with which it is specifically associated, which can include conferring a property that makes the labeled compound or composition able to bind specifically to another molecule. "Labeled" refers to a compound or composition that is specifically associated, typically by covalent bonding but non-covalent interactions can also be employed to label a compound or composition, with a label. Thus, a label may be detectable directly, i.e., the label can be a radioisotope (e.g., $^3H$, $^{14}C$, $^{32}P$, $^{35}S$, 125I, 131I) or a fluorescent or phosphorescent molecule (e.g., FITC, rhodamine, lanthanide phosphors), or indirectly, i.e., by enzymatic activity (e.g., horseradish peroxidase, beta-galactosidase, luciferase, alkaline phosphatase) or by its ability to bind to another molecule (e.g., streptavidin, biotin, an antigen, epitope, or antibody). Incorporation of a label can be achieved by a variety of means, ie., by use of radiolabeled or biotinylated nucleotides in polymerase-mediated primer extension reactions, epitope-tagging via recombinant expression or synthetic means, or binding to an antibody. Labels can be attached directly or via spacer arms of various lengths, i.e., to reduce steric hindrance. Any of a wide variety of labeled reagents can be used for purposes of the present invention. For instance, one can use one or more labeled nucleoside triphosphates, primers, linkers, or probes. The term label can also refer to a "tag", which can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect the presence of HRP. In a similar fashion, the tag can be an epitope or antigen (e.g., digoxigenin), and an enzymatically, fluorescently, or radioactively labeled antibody can be used to bind to the tag.

"Naturally occurring" refers to a substance, typically an amino acid, nucleotide, nucleic acid, or protein that exists in nature without human intervention. For example, deoxyribonucleic acid or DNA is naturally occurring. If a naturally occurring substance is produced by human intervention, the resulting substance is referred to as "synthetic" or "recombinant."

An "oligonucleotide" refers to a polymer of composed of nucleotides. Naturally occurring oligonucleotides include DNA and RNA and, as discussed above, can exist as single-stranded polymers or as duplexes, triplexes, or higher-order compositions of single-stranded polymers. An oligonucleotide can also be referred to as a polynucleotide or nucleic acid; typically, the latter terms are used to describe oligonucleotides of substantial (i.e., 50 to 100 to 1000 to 10,000 or more nucleotides in) length, while the term oligonucleotide is most often used to refer to a polynucleotide from about 8 to 30 nucleotides in length. Oligonucleotide, as used herein, also refers to synthetic and non-naturally occurring forms or analogues of naturally occurring oligonucleotides, and such analogues can differ, relative to their naturally occurring counterparts, either in the linkages between nucleotides or in the base or sugar components of the nucleotides. For example, but without limitation, synthetic oligonucleotides include peptide-nucleic acids (PNAs), phosphoramidates, phosphorothioates, methyl phosphonates, 2-O-metyl ribonucleic acids, and the like. See also, Nielsen et al., 1993, *Anticancer Drug Des.* 8:53–63, incorporated herein by reference. Polynucleotides and fragments or analogs thereof, may be prepared according to methods known in the art and described in Maniatis et al., Molecular Cloning: A Laboratory Manual, 2nd Ed., (1989), Cold Spring Harbor, N.Y., and Berger and Kimmel, Methods in Enzymology, Volume 152, Guide to Molecular Cloning Techniques (1987), Academic Press, Inc., San Diego, Calif., which are incorporated herein by reference.

The phrase "open reading frame" or "coding sequence" refers to a nucleotide sequence that encodes a polypeptide or protein. Such sequences are typically bordered on the 5'-end by an initiation codon (ATG) or another codon that does not encode a stop codon and on the 3'-end by a stop codon.

A "pharmaceutical composition" refers to a composition suitable for pharmaceutical or therapeutic use in a mammal. A pharmaceutical composition comprises a pharmacologically effective amount of an active agent and typically a pharmaceutically acceptable carrier.

The phrase "pharmaceutically acceptable carrier" refers to a pharmaceutical carrier, buffer, or excipient, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral, oral, parenteral, subcutaneous, intramuscular, intravenous, intraperitoneal, topical, transdermal, or transmucosal administration.

"Pharmacologically effective amount" refers to that amount of an agent effective to produce the intended pharmacological result.

"Physiological conditions" refer to temperature, pH, ionic strength, viscosity, and like biochemical parameters compatible with a viable organism, such as those that exist intracellularly in a viable mammalian cell. For example, the intracellular conditions in a mammalian cell grown under typical laboratory culture conditions are physiological conditions. Suitable in vitro reaction conditions for PCR and many polynucleotide enzymatic reactions and manipulations are generally physiological conditions. In general, in vitro physiological conditions are 50–200 mM NaCl or KCl, pH 6.5–8.5, 20–45 degrees C., and 0.001–10 mM divalent cation (e.g., Mg++, Ca++); preferably about 150 mM NaCl or KCl, pH 7.2–7.6, 5 mM divalent cation, and often include 0.01–1.0 percent protein (e.g., BSA). A non-ionic detergent (Tween, NP-40, Triton X-100) can also be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

"Polymerase" refers to any enzyme capable of catalyzing a polymerization reaction, as of, for example, nucleotide to polynucleotides. It is intended that the term encompass any polymerase suitable for use in the amplification of nucleic acids of interest, including DNA polymerases such as Taq DNA polymerase obtained from *Thermus aquaticus*, although other polymerases, both thermostable and thermolabile, are also encompassed by this definition.

"Polypeptide" or "peptide" or "protein" refers to a polymer of amino acid residues and to variants and synthetic analogs of the same and are used interchangeably herein. Thus, these terms apply to amino acid polymers in which one or more amino acid residues is a synthetic non-naturally occurring amino acid, such as a chemical analog of a corresponding naturally occurring amino acid, as well as to naturally occurring amino acid polymers.

"Primer" refers to an oligonucleotide, i.e., a purified restriction fragment or a synthetic oligonucleotide, capable of acting as a point of initiation of synthesis when placed under conditions in which synthesis of a primer extension product complementary to a nucleic acid strand (the "template") is induced, i.e., in the presence of nucleotides and an agent for polymerization, such as DNA polymerase, and at a suitable temperature and pH. The primer is preferably single-stranded for maximum efficiency in amplification but may alternatively be double-stranded. If double stranded, the primer may need to be treated to separate its strands before being used to prepare extension products. Primers are typically oligodeoxyribonucleotides, but a wide variety of synthetic and non-naturally occurring oligonucleotide primers can be used for various applications. The preferred length of a primer depends on many factors, including application, temperature to be employed, template, reaction conditions, other reagents, and source. For example, depending on the complexity of the target sequence, an oligonucleotide primer typically contains 15–25 or more nucleotides, although it may contain fewer or more nucleotides. Short primer molecules generally require cooler temperatures to form stable hybrid complexes with template. Primers can be large polynucleotides, such as from about 200 nucleotides to several kilobases or more in length. A primer must be sufficiently complementary to the sequence on the template to which it is to hybridize to serve as a site for the initiation of synthesis but need not reflect the exact sequence of the template. For example, non-complementary nucleotides may be attached to the 5'-end of the primer, with the remainder of the primer sequence being complementary to the template. Alternatively, non-complementary nucleotides or longer sequences can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence of monomers in a polymer or to a moiety of another molecule. A probe can be, for example, an oligonucleotide that is capable of hybridizing to another oligonucleotide or polynucleotide of interest, often called the "target", through complementary base pairing, and such a probe can bind target nucleic acids lacking complete sequence complementarity with the probe, depending upon the stringency of the hybridization conditions. Oligonucleotide probes are useful in the detection, identification and isolation of particular gene sequences or products. A probe can also be an antibody that binds an antigen or epitope in a target. A probe is often labeled so that it is detectable in a detection system, such as, for example and without limitation, an enzyme (e.g., ELISA, as well as enzyme-based histochemical assays), fluorescent, radioactive, or luminescent detection system.

"Recombinant" refers to the results of methods, reagents, and laboratory manipulations in which nucleic acids or other biological molecules are enzymatically, chemically or biologically cleaved, synthesized, combined, or otherwise manipulated in vitro to produce desired products in cells or other biological systems. For example, a polynucleotide can be inserted into a suitable vector, such as a bacterial plasmid, and the plasmid can be used to transform a suitable host cell to produce a recombinant protein encoded by the polynucleotide. The transformed host cell may be a prokaryotic or eukaryotic, including a bacterial, yeast, insect, or mammalian, cell. Thus, "recombinant DNA" refers to a DNA molecule that is produced by such techniques, and a "recombinant host cell" refers to a cell that comprises a recombinant nucleic acid molecule, typically a recombinant plasmid or other expression vector. Recombinant host cells can express genes that are not found within the native (non-recombinant) form of the cell. For example, such cells can produce a "recombinant protein," which refers to a protein that is produced by expression of a recombinant DNA that encodes the amino acid sequence of the protein.

"Sample" refers to a composition of matter and typically comprises a cell extract, cell, tissue, or a compound or composition derived therefrom, such as a chromosome, genomic DNA, RNA, cDNA, and the like.

"Senescent gene expression" refers to the expression of genes and gene products that are differentially expressed in a senescent as opposed to a young cell. Senescent gene expression can be altered by increasing the expression of young cell specific genes and/or decreasing expression of senescent cell specific genes. These cell specific genes are also denoted as "senescence-related genes". The proteins encoded by the senescence-related genes are also referred to herein as "senescence-related proteins."

"Specifically binds to" or "specific binding" or "specifically binding" refers to the ability of one molecule, typically a macromolecule such as an antibody or oligonucleotide, to contact and associate with another specific molecule in the presence of other different molecules. For example, a single-stranded oligonucleotide "specifically bind to" a single-stranded oligonucleotide that is complementary in sequence, and an antibody "specifically binds to" or "is specifically immunoreactive with" its corresponding antigen.

"Specific hybridization" refers to the formation of hybrids between a probe polynucleotide (e.g., a polynucleotide of the invention which may include substitutions, deletions, and/or additions) and a specific target polynucleotide (e.g., a polynucleotide having the sequence of a GC6 gene or gene product) through base pairing, wherein the probe preferentially hybridizes to the specific target and not to other polynucleotides in the mixture that do not share sequence identity with the target.

"Standard growth conditions" refers to the use of standard culture conditions, i.e., physiological condition and medium used to grow or culture cells.

"Substantially pure" means an object species is the predominant species present (i.e., on a molar basis, more abundant than any other individual macromolecular species in the composition), and a substantially purified fraction is a composition wherein the object species typically comprises at least about 50 percent (on a molar basis) of all macromolecular species present. Generally, a substantially pure composition means that about 80 to 90 percent or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are typically not considered macromolecular species for purposes of this definition.

"Suitable reaction conditions" refers to those conditions suitable for conducting a specified reaction, typically using commercially available reagents. Such conditions are known or readily established by those of skill in the art for a variety of reactions. For example, suitable polymerase chain reaction (PCR) conditions include those conditions specified in U.S. Pat. Nos. 4,683,202; 4,683,195; 4,800,159; and 4,965,188, each of which is incorporated herein by reference.

"Target" refers to the region, sequence or object fixed as a point for amplification, binding, synthesis, isolation, or the like. For example, target can refer to the region of nucleic acid bounded by the primers used for polymerase chain reaction, the region of a nucleic acid to which a probe specifically hybridizes, or the region on a peptide or protein to which an antibody binds.

"Therapeutically effective amount or dose" refers to an amount of a pharmaceutical compositions that is administered to a patient suffering from a disease and is sufficient to cure or at least partially arrest or ameliorate the symptoms of the disease and its complications. The amount will depend on the severity of the disease and the patient and can be determined by standard pharmaceutical procedures in cell cultures or experimental animals. The therapeutic index is the ratio LD50/ED50 (ED50, the dose therapeutically effective in 50% of the population; and LD50, the dose lethal to 50% of the population), and pharmaceutical compositions that exhibit large therapeutic indices are preferred. The data obtained from cell culture assays and animal studies is used in formulating a range of dosages for human use. The dosage of such compounds lies preferably within a range of circulating concentrations that include the ED50 with little or no toxicity. The dosage varies within this range depending upon the dosage form employed, sensitivity of the patient, and the route of administration.

II. Reagents and Compounds of the Invention

The methods and reagents of the present invention in part arise out of the recognition that the structural and functional changes in organs and tissues that are intrinsic to the aging process can be attributed to an alteration in the pattern of gene expression that accompanies cell senescence. Research into cellular aging has provided insight into the mechanism through which the lifespan of cells is regulated. Hayflick and Moorhead reported in 1961 that, with continuous passage, human diploid fibroblasts reach replicative senescence at a characteristic number of population doublings. Somatic cells derived from the tissues of a young individual and grown in culture can divide a maximum of about 50–100 times before reaching senescence. Furthermore, the upper limit in the number of cell divisions is inversely related to the age of the donor. Replicative senescence is a genetically-programmed series of changes exhibited by normal cells that culminates in exit from the cell cycle and expression of a senescent genotype and phenotype.

As the body ages, the proportion of senescent cells increases. The accumulation of such cells has both direct and indirect effects that contribute to age related changes and pathologies. As a cell becomes senescent, changes in the pattern of gene expression lead to functional changes. These changes can then influence the physiology of surrounding cells by altering the extracellular environment or in a paracrine fashion through the release of different proteins. For instance, the consequence of an accumulation of senescent cells within the skin is a progressive decrease in skin structure and function. Thus, modulation of senescent gene expression can be used to ameliorate the problems associated with the accumulation of senescent cells.

One approach to alter senescent gene expression expression is through regulation of steady-state mRNA levels at the transcriptional and post-transcriptional level. However, old cells can differ from young cells not only by altered steady state mRNA levels but also by altered levels of a protein or the activity of a protein, which can be due to alterations in mRNA translation or protein structure. Thus, regulation of gene expression can occur by a variety of mechanisms. At the transcriptional level, the production of mRNAs can either increase or decrease. The level of translation or changes in post-translational modification can lead to an increase or decrease in the abundance of proteins. The activity of a protein can be modulated or the turnover rate of the protein can change. Each of these mechanisms can in turn be regulated.

The present invention provides compounds and reagents relating to the GC6 gene, the expression of which is controlled at least in part by the aging process. The present invention provides useful nucleic acids in isolated form derived from the GC6 gene, including its promoter and coding sequence. These nucleic acids are useful as primers and probes in diagnostic methods and as components of recombinant DNA cloning and/or expression vectors, as well as for other applications described herein. The present invention also provides recombinant and synthetic GC6 gene products and antibodies that bind specifically to the pGC6 gene product, as further described below.

The GC6 gene product was identified as a senescence-specific gene by a technique known as Enhanced Differential Display (EDD; Villeponteau et al., U.S. Pat. No. 5,580,726, issued Dec. 3, 1996; incorporated herein by reference). In this technique, cDNAs of differentially expressed mRNAs from young and old fibroblast strains are synthesized using 3' (T rich) primers for targeting the poly A tail of pol II mRNA transcripts and 5' arbitrary primers, as described in Linskens et al., 1995, *Nucleic Acids Research* 23:3244–3251 and Villeponteau et al., supra; both incorporated herein by reference.

A 3' primer, 5'-GCGCAAGCTTTTTTTTTTTTGG-3' (SEQ ID NO. 1), designated as "E," and a 5' primer, 5'-CGG GAA GCT TAC TCC ATG ACT C-3' (SEQ ID NO. 2), designated as "11" generated a "genetag," designated "11E3," that was cloned and partially sequenced. The sequence obtained, 5'-AGGGGCACAAGAGTTTGC GGTTATTGAATCCTGAGANAA-3' (SEQ ID NO. 3), wherein N indicates that the identity of the nucleotide at that position was not determined), did not match any known sequence.

A probe corresponding to the genetag 11E3 was prepared by restriction enzyme digestion of a plasmid containing the genetag followed by isolation of the appropriate fragment on low-melting agarose and labeling of the fragment using the random hexamer-primed method (Feinberg & Vogelstein, 1983, *Analyt. Biochem.* 132:6–13). Screening of a commercially available human cDNA library using the probe identified a plasmid, designated pGC6L, that comprised a cDNA of about 2.7 kb with an open reading frame (ORF) about 1625 nucleotides in length and encoding approximately 542 amino acids or a predicted gene product of approximately 59.5 kD. Because Northern analysis of fibroblast RNA with probes corresponding to the 11E3 genetag and clone identified two mRNA species of 3.3, and 2.7 kb in length, the coding sequence of pGC6L appeared to be incomplete.

A probe was therefore generated by PCR using one primer corresponding to the 5' end of the clone—this primer was designated KJC47 and is defined by the sequence: 5'-GCAGGAAGGCGGCACGAGAG-3' (SEQ ID NO. 4)—and another primer corresponding to an internal sequence—this primer was designated KJC48 and is defined by the sequence: 5'-TTGTATCTTTGTTTGGGATG-3' (SEQ ID NO. 5). The resulting probe was used to screen a lambda GT11 cDNA library prepared using RNA isolated from the 293 HEK cell line.

A lambda clone, designated lambda 3-1-4, was isolated, and PCR using the primer KJC42, defined by the sequence: 5'-TAGGCCCAGATCACTCTCACAGTG CTA T-3' (SEQ ID NO. 6), and a gt11 primer defined by the sequence: 5'-CACCAGACCAACTGGTAATGGTAGCGAC-3' (SEQ ID NO. 7), was used to generate a duplex DNA containing the insert. The PCR product was ligated into pCR2.1 TA cloning vector (Invitrogen) to generating a plasmid designated as pGC6-5'end. DNA sequencing showed that pGC6-5'end contained the remaining coding sequence for the GC6 protein.

The present invention provides recombinant plasmids that can be used to express biologically active pGC6. To prepare such plasmids, the nucleotide sequence encoding the GC6 ORF, or its functional equivalent, is inserted into an appropriate expression vector (i.e., a vector which contains the necessary elements for the transcription and translation of the inserted coding sequence). A GC6 eukaryotic expression vector, pCIneoGC6, comprising the full-coding sequence for GC6 was assembled by splicing the appropriate coding sequences of the pGC6L and lambda 3-1-4 and synthetic and recombinant nucleic acids.

To construct plasmid pCIneoGC6, a nucleic acid comprising the 5' end of the GC6 ORF was generated by amplifying lambda 3-1-4 with primer KJC42 and a primer, KJC51, containing an XhoI site and defined by the sequence: 5'-ATACCGCTCGAGCGGACCTGATTCCCCAGTTGG-3' (SEQ ID NO. 8). This PCR product, designated KJC51-KJC42, is defined by the sequence:

```
5'- ATACCGCTCG AGCGGACCTG ATTCCCCAGT TGGAATACTC

CAGCCCCTTG GAAATTCCCG GGATTTATAA AATAACTCTA

GACAACAAGA CTTTGTCTTT AAAGGTCCTA TGAATTCTTT

TCTCTCTGTA TTTANGTATC CTGATTTTTC TTTTCCATAT

TTTCCACAGG ATTATTTTAC AAATGCAAAT AGAGAGTTGA

AAAAAGATGC TCAGCAAGAT TACCATCTAG AATATGCCAT

GGAAAATAGC ACACACACAA TAATTGAATT TACCAGAGAG

CTGCATACAT GTGACATAAA TGACAAGAGT ATAACGGATA

GCACTGTGAG AGTGATCTGG GCCTA-3'
```

(SEQ ID NO. 9), and was ligated into TA cloning vector, pCR2.1 (Invitrogen). A restriction fragment, designated 5'GC6 XhoI/NcoI, and defined by the sequence:

```
5'- TCGAGCGGAC CTGATTCCCC AGTTGGAATA CTCCAGCCCT

TGGAAATTCC CGGGATTTAT AAAATAACTC TAGACAACAA

GACTTTGTCT TTAAAGGTCC TATGAATTCT TTTCTCTCTG

TATTTANGTA TCCTGATTTT TCTTTTCCAT ATTTTCCACA

GGATTATTTT ACAAATGCAA ATAGAGAGTT GAAAAAAGAT

GCTCAGCAAG ATTACCATCT AGAATATGC-3'
```

(SEQ ID NO. 10) was then generated by digesting the resultant plasmid with restriction enzymes NcoI and XbaI. A restriction fragment, designated GC6 NcoI/XbaI, comprising the 3' end fragment was generated by digesting pGC6L with restriction enzymes NcoI and XbaI. The DNA sequence for GC6 NcoI/XbaI is shown below (in the 5' to 3' direction).

```
                                              (SEQ ID NO.11)
CATGGAAAATAGCACACACACAATAATTGAATTTACCAGAGAGCTGCATA

CATGTGACATAAATGACAAGAGTATAACGGATAGCACTGTGAGAGTGATC

TGGGCCTACCACCATGAAGATGCAGGAGAAGCTGGTCCCAAGTACCATGA

CTCCAATAGGGGCACCAAGAGTTTGCGGTTATTGAATCCTGAGAAAACTA

GTGTGCTATCTACAGCCTTACCATACTTTGATCTGGTAAATCAGGACGTC

CCCATCCCAAACAAAGATACAACATATTGGTGCCAAATGTTTAAGATTCC

TGTGTTCCAAGAAAAGCATCATGTAATAAAGGTTGAGCCAGTGATACAGA

GAGGCCATGAGAGTCTGGTGCACCACATCCTGCTCTATCAGTGCAGCAAC

AACTTTAACGACAGCGTTCTGGAGTCCGGCCACGAGTGCTATCACCCCAA

CATGCCCGATGCATTCCTCACCTGTGAAACTGTGATTTTTGCCTGGGCTA

TTGGTGGAGAGGGCTTTTCTTATCCACCTCATGTTGGATTATCCCTTGGC

ACTCCATTAGATCCGCATTATGTGCTCCTAGAAGTCCATTATGATAATCC

CACTTATGAGGAAGGCTTAATAGATAATTCTGGACTGAGGTTATTTTACA

CAATGGATATAAGGAAATATGATGCTGGGGTGATTGAGGCTGGCCTCTGG

GTGAGCCTCTTCCATACCATCCCTCCAGGGATGCCTGAGTTCCAGTCTGA

GGGTCACTGCACTTTGGAGTGCCTGGAAGAGGCTCTGGAAGCCGAAAAGC

CAAGTGGAATTCATGTGTTTGCTGTTCTTCTCCATGCTCACCTGGCTGGC

AGAGGCATCAGGCTGCGTCATTTTCGAAAAGGGAAGGAAATGAAATTACT

TGCCTATGATGATGATTTTGACTTCAATTTCCAGGAGTTTCAGTATCTAA

AGGAAGAACAAACAATCTTACCAGGAGATAACCTAATTACTGAGTGTCGC

TACAACACGAAAGATAGAGCTGAGATGACTTGGGGAGGACTAAGCACCAG

GAGTGAAATGTGTCTCTCATACCTTCTTTATTACCCAAGAATTAATCTTA

CTCGATGTGCAAGTATTCCAGACATTATGGAACAACTTCAGTTCATTGGG

GTTAAGGAGATCTACAGACCAGTCACGACCTGGCCTTTCATTATCAAAAG

TCTCAAGCAATATAAAAACCTTTCTTTCATGGATGCTATGAATAAGTTTA

AATGGACTAAAAAGGAAGGTCTCTCCTTCAACAAGCTGGTCCTCAGCCTG

CCAGTGAATGTGAGATGTTCCAAGACAGACAATGCTGAGTGGTCGATTCA

AGGAATGACAGCATTACCTCCAGATATAGAAAGACCCTATAAAGCAGAAC

CTTTGGTGTGTGGCACGTCTTCTTCCTCTTCCCTGCACAGAGATTTCTCC
```

-continued

```
ATCAACTTGCTTGTTTGCCTTCTGCTACTCAGCTGCACGCTGAGCACCAA

GAGCTTGTGATCAAAATTCTGTTGGACTTGACAATGTTTTCTATGATCTG

AACCTGTCATTTGAAGTACAGGTTAAAGACTGTGTCCACTTTGGGCATGA

AGAGTGTGGAGACTTTTCTTCCCCATTTTCCCTCCCTCCTTTTTCCTTTC

CATGTTACATGAGAGACATCAATCAGGTTCTCTTCTCTTTCTTAGAAATA

TCTGATGTTATATATACATGGTCAATAAAATAAAACTGGCCTGACTTAAG

ATAACCATTTTAAAAAATTGGGCTGTCATGTGGGAATAAAAGAATTCTTT

CTTTCCTACTACATTCTGTTTTATTTAAATACTCATTGTTGCTATTTCAC

TTTTTGACTTGACTTTTATATTTCTTTAAAAAATTCCTTCCTTTTAAAAA

ATATAAAAGGGACTACTGTTCATTCCAGTTTTCTTCTTCTTTGTTGTTCT

TCTAGTGTGACTTTTCAAGTGTAACAGCCATTCTTCCTGACTTTAATATT

GTCCAGTTCTGGTCTTTTCTGTGAATTACCACTGGGCCCCTTACCTCAAT

GCTTTTTGTTGATGCCCACTCTGGTTCCCTTGTTTATCTGAGTCTGTTGG

TACCCCAAATGACCCCACACCCATYTTAAAGTACTTTTTTTCACCTTCCC

TGTTTAGTACTGGCCAGATGAGTTTTTT.
```

These fragments, 5'GC6 XhoI/NcoI and GC6 NcoI/XbaI, were then ligated into an expression plasmid, designated pCIneo, that had been digested with restriction enzymes XhoI and XbaI to yield the GC6 expression plasmid pCIneoGC6. The sequence of this vector was confirmed using sequencing primers KJC52, defined by the sequence: 5'-TAATACGACTCACTATAG-3' (SEQ ID NO. 12); and KJC53, defined by the sequence: 5'-ATTAACCCTCACTAAAGGGA-3' (SEQ ID NO. 13). The DNA sequence for the complete ORF of the GC6 gene, the 5' and 3' untranslated regions of the GC6 mRNA, and the amino acid sequence encoded by the ORF and that defines pGC6 are shown below (nucleic acid sequences are shown in the 5' to 3' direction; amino acid sequences are shown in the amino to carboxy terminus direction; an * designates a stop codon).

```
                                           (SEQ ID NO. 14)
ACTTTCCAAGGAAGGAAAGGCACACAATGGTATCAAATGTTC       42

ATTCATTCCATCTCTTGATGCTCTACGATATTATCAGTCTAC       82

ACTATGCTTTCCTGAAAGGCCAGAAGTTCAAAGATGGACTAG      126

TTTCCCAGGGACCTGATTCCCAGTTGGAATACTCCAGCCCC       168

TTGGAAATTCCCGGGATTTATAAAATAACTCTAGACAACAAG      210

M  N  S  F  L  S  V  F              8
ACTTTGTCTTTAAAGGTCCTATGAATTCTTTTCTCTCTGTAT       252

R  Y  P  D  F  S  F  P  Y  F  P  Q  D  Y   22
TTAGGTATCCTGATTTTTCTTTTCCATATTTTCCACAGGATT        294

F  T  N  A  N  R  E  L  K  K  D  A  Q  Q   36
ATTTTACAAATGCAAATAGAGAGTTGAAAAAAGATGCTCAGC        336

D  Y  H  L  E  Y  A  M  E  N  S  T  H  T   50
AAGATTACCATCTAGAATATGCCATGGAAAATAGCACACACA        378

I  I  E  F  T  R  E  L  H  T  C  D  I  N   64
```

```
                                                        CAATAATTGAATTTACCAGAGAGCTGCATACATGTGACATAA  420

D   K   S   I   T   D   S   T   V   R   V   I   W   A    78
    ATGACAAGAGTATAACGGATAGCACTGTGAGAGTGATCTGGG                 462

Y   H   H   E   D   A   G   E   A   G   P   K   Y   H    92
    CCTACCACCATGAAGATGCAGGAGAAGCTGGTCCCAAGTACC                 504

D   S   N   R   G   T   K   S   L   R   L   L   N   P   106
    ATGACTCCAATAGGGGCACCAAGAGTTTGCGGTTATTGAATC                 546

E   K   T   S   V   L   S   T   A   L   P   Y   F   D   120
    CTGAGAAAACTAGTGTGCTATCTACAGCCTTACCATACTTTG                 588

L   V   N   Q   D   V   P   I   P   N   K   D   T   T   134
    ATCTGGTAAATCAGGACGTCCCCATCCCAAACAAAGATACAA                 630

Y   W   C   Q   M   F   K   I   P   V   F   Q   E   K   148
    CATATTGGTGCCAAATGTTTAAGATTCCTGTGTTCCAAGAAA                 672

H   H   V   I   K   V   E   P   V   I   Q   R   G   H   162
    AGCATCATGTAATAAAGGTTGAGCCAGTGATACAGAGAGGCC                 714

E   S   L   V   H   H   I   L   L   Y   Q   C   S   N   176
    ATGAGAGTCTGGTGCACCACATCCTGCTCTATCAGTGCAGCA                 756

N   F   N   D   S   V   L   E   S   G   H   E   C   Y   190
    ACAACTTTAACGACAGCGTTCTGGAGTCCGGCCACGAGTGCT                 798

H   P   N   M   P   D   A   F   L   T   C   E   T   V   204
    ATCACCCCAACATGCCCGATGCATTCCTCACCTGTGAAACTG                 840

I   F   A   W   A   I   G   G   E   G   F   S   Y   P   218
    TGATTTTTGCCTGGGCTATTGGTGGAGAGGGCTTTTCTTATC                 882

P   H   V   G   L   S   L   G   T   P   L   D   P   H   232
    CACCTCATGTTGGATTATCCCTTGGCACTCCATTAGATCCGC                 924

Y   V   L   L   E   V   H   Y   D   N   P   T   Y   E   246
    ATTATGTGCTCCTAGAAGTCCATTATGATAATCCCACTTATG                 966

E   G   L   I   D   N   S   G   L   R   L   F   Y   T   260
    AGGAAGGCTTAATAGATAATTCTGGACTGAGGTTATTTTACA                1008

M   D   I   R   K   Y   D   A   G   V   I   E   A   G   274
    CAATGGATATAAGGAAATATGATGCTGGGGTGATTGAGGCTG                1050

L   W   V   S   L   F   H   T   I   P   P   G   M   P   288
    GCCTCTGGGTGAGCCTCTTCCATACCATCCCTCCAGGGATGC                1092

E   F   Q   S   E   G   H   C   T   L   E   C   L   E   302
    CTGAGTTCCAGTCTGAGGGTCACTGCACTTTGGAGTGCCTGG                1134

E   A   L   E   A   E   K   P   S   G   I   H   V   F   316
    AAGAGGCTCTGGAAGCCGAAAAGCCAAGTGGAATTCATGTGT                1176

A   V   L   L   H   A   H   L   A   G   R   G   I   R   330
    TTGCTGTTCTTCTCCATGCTCACCTGGCTGGCAGAGGCATCA                1218

L   R   H   F   R   K   G   K   E   M   K   L   L   A   344
    GGCTGCGTCATTTTCGAAAAGGGAAGGAAATGAAATTACTTG                1260

Y   D   D   D   F   D   F   N   F   Q   E   F   Q   Y   358
    CCTATGATGATGATTTTGACTTCAATTTCCAGGAGTTTCAGT                1302

L   K   E   E   Q   T   I   L   P   G   D   N   L   I   372
    ATCTAAAGGAAGAACAAACAATCTTACCAGGAGATAACCTAA                1344

T   E   C   R   Y   N   T   K   D   R   A   E   M   T   386
    TTACTGAGTGTCGCTACAACACGAAAGATAGAGCTGAGATGA                1386

W   G   G   L   S   T   R   S   E   M   C   L   S   Y   400
    CTTGGGGAGGACTAAGCACCAGGAGTGAAATGTGTCTCTCAT                1428

L   L   Y   Y   P   R   I   N   L   T   R   C   A   S   414
    ACCTTCTTTATTACCCAAGAATTAATCTTACTCGATGTGCAA                1470

I   P   D   I   M   E   Q   L   Q   F   I   G   V   K   428
    GTATTCCAGACATTATGGAACAACTTCAGTTCATTGGGGTTA                1512
```

```
     E   I   Y   R   P   V   T   T   W   P   F   I   I   K   442
    AGGAGATCTACAGACCAGTCACGACCTGGCCTTTCATTATCA                1554

S   L   K   Q   Y   K   N   L   S   F   M   D   A   M   456
    AAAGTCTCAAGCAATATAAAAACCTTTCTTTCATGGATGCTA                1596

N   K   F   K   W   T   K   K   E   G   L   S   F   N   470
    TGAATAAGTTTAAATGGACTAAAAAGGAAGGTCTCTCCTTCA                1638

K   L   V   L   S   L   P   V   N   V   R   C   S   K   484
    ACAAGCTGGTCCTCAGCCTGCCAGTGAATGTGAGATGTTCCA                1680

T   D   N   A   E   W   S   I   Q   G   M   T   A   L   498
    AGACAGACAATGCTGAGTGGTCGATTCAAGGAATGACAGCAT                1722

P   P   D   I   E   R   P   Y   K   A   E   P   L   V   512
    TACCTCCAGATATAGAAAGACCCTATAAAGCAGAACCTTTGG                1764

C   G   T   S   S   S   S   S   L   H   R   D   F   S   526
    TGTGTGGCACGTCTTCTTCCTCTTCCCTGCACAGAGATTTCT                1806

I   N   L   L   V   C   L   L   L   L   S   C   T   L   540
    CCATCAACTTGCTTGTTTGCCTTCTGCTACTCAGCTGCACGC                1848

S   T   K   S   L   *                                   545
    TGAGCACCAAGAGCTTGTGATCAAAATTCTGTTGGACTTGAC                1890

AATGTTTTCTATGATCTGAACCTGTCATTTGAAGTACAGGTT                1932

AAAGACTGTGTCCACTTTGGGCATGAAGAGTGTGGAGACTTT                1974

TCTTCCCCATTTTCCCTCCCTCCTTTTTCCTTTCCATGTTAC                2016

ATGAGAGACATCAATCAGGTTCTCTTCTCTTTCTTAGAAATA                2058

TCTGATGTTATATATACATGGTCAATAAAATAAAACTGGCCT                2100

GACTTAAGATAACCATTTTAAAAAATTGGGCTGTCATGTGGG                2142

AATAAAAGAATTCTTTCTTTCCTACTACATTCTGTTTTATTT                2184

AAATACTCATTGTTGCTATTTCACTTTTTGACTTGACTTTTA                2226

TATTTCTTTAAAAAATTCCTTCCTTTTAAAAAATATAAAAGG                2268

GACTACTGTTCATTCCAGTTTTCTTCTTCTTTGTTGTTCTTC                2310

TAGTGTGACTTTTCAAGTGTAACAGCCATTCTTCCTGACTTT                2352

AATATTGTCCAGTTCTGGTCTTTTCTGTGAATTACCACTGGG                2394

CCCCTTACCTCAATGCTTTTTGTTGATGCCCACTCTGGTTCC                2436

CTTGTTTATCTGAGTCTGTTGGTACCCCAAATGACCCCACAC                2478

CCATYTTAAAGTACTTTTTTTCACCTTCCCTGTTTAGTACTG                2520

GCCAGATGAGTTTTTTCTAGAGCTCTGTCACTATCTGAAAAG                2562

AAAGAGGCTATGGGAAACATAGAAATGGTATGTATTAATAAC                2604

TGATCATAGGCTGAGGAGAAAAAATGTAGCTGGCTGCAAACC                2646

CAGTGCTGTGAGGTGACTTATATGAGGTTCCAGATCAAAGAC                2688

AGGCCGTGTGAGCCAGTCCAGGAGGGTGTAAGTTCTGAATGG                2730

TTCCTTGCTGACTTTGGGTGACACATGTACCACATACTGGCT                2772

CAGTTTAAGTCATGGTTCTATTGTAGATTTATTTTTATATTA                2814

GTTAATAAATGACTTTAAATTGTCACCAATTGAAAATCTTGT                2856

CACTCTTTTGGTTTTCTTTATATAGCTCAGCCAAATCTCTGT                2898

TTTATGTCCTGTCCTCATCTCTTAAGCTAAATCTGTTTGGAT                2940

CATATTAATAAACCTCGTGCCGAATTCGAT.                           2970
```

The GC6 ORF encodes a protein of 545 amino acids with a predicted primary translation product size of 622607 Daltons. A comparison of the predicted GC6 protein (pGC6) to human (Genbank accession number P09172), bovine (Genbank accession number P15101), and rat (Genbank accession number Q05754) dopamine beta-hydroxylase (DBH), also known as dopamine monooxygenase precursor, showed that pGC6 has significant homology to these proteins, with many conserved cysteine residues suggesting a similar overall folding conformation. The ORF of the GC6 gene is:

(SEQ ID NO: 16)
```
5'-ATGAATTCTTTTCTCTCTGTAT
TTAGGTATCCTGATTTTTCTTTTCCATATTTTCCACAGGATT
ATTTTACAAATGCAAATAGAGAGTTGAAAAAAGATGCTCAGC
AAGATTACCATCTAGAATATGCCATGGAAAATAGCACACACA
CAATAATTGAATTTACCAGAGAGCTGCATACATGTGACATAA
ATGACAAGAGTATAACGGATAGCACTGTGAGAGTGATCTGGG
CCTACCACCATGAAGATGCAGGAGAAGCTGGTCCCAAGTACC
ATGACTCCAATAGGGGCACCAAGAGTTTGCGGTTATTGAATC
CTGAGAAAACTAGTGTGCTATCTACAGCCTTACCATACTTTG
ATCTGGTAAATCAGGACGTCCCCATCCCAAACAAAGATACAA
CATATTGGTGCCAAATGTTTAAGATTCCTGTGTTCCAAGAAA
AGCATCATGTAATAAAGGTTGAGCCAGTGATACAGAGAGGCC
ATGAGAGTCTGGTGCACCACATCCTGCTCTATCAGTGCAGCA
ACAACTTTAACGACAGCGTTCTGGAGTCCGGCCACGAGTGCT
ATCACCCCAACATGCCCGATGCATTCCTCACCTGTGAAACTG
TGATTTTTGCCTGGGCTATTGGTGGAGAGGGCTTTTCTTATC
CACCTCATGTTGGATTATCCCTTGGCACTCCATTAGATCCGC
ATTATGTGCTCCTAGAAGTCCATTATGATAATCCCACTTATG
AGGAAGGCTTAATAGATAATTCTGGACTGAGGTTATTTTACA
CAATGGATATAAGGAAATATGATGCTGGGGTGATTGAGGCTG
GCCTCTGGGTGAGCCTCTTCCATACCATCCCTCCAGGGATGC
CTGAGTTCCAGTCTGAGGGTCACTGCACTTTGGAGTGCCTGG
AAGAGGCTCTGGAAGCCGAAAAGCCAAGTGGAATTCATGTGT
TTGCTGTTCTTCTCCATGCTCACCTGGCTGGCAGAGGCATCA
GGCTGCGTCATTTTCGAAAAGGGAAGGAAATGAAATTACTTG
CCTATGATGATGATTTTGACTTCAATTTCCAGGAGTTTCAGT
ATCTAAAGGAAGAACAAACAATCTTACCAGGAGATAACCTAA
TTACTGAGTGTCGCTACAACACGAAAGATAGAGCTGAGATGA
CTTGGGGAGGACTAAGCACCAGGAGTGAAATGTGTCTCTCAT
ACCTTCTTTATTACCCAAGAATTAATCTTACTCGATGTGCAA
GTATTCCAGACATTATGGAACAACTTCAGTTCATTGGGGTTA
AGGAGATCTACAGACCAGTCACGACCTGGCCTTTCATTATCA
AAAGTCTCAAGCAATATAAAAACCTTTCTTTCATGGATGCTA
TGAATAAGTTTAAATGGACTAAAAAGGAAGGTCTCTCCTTCA
ACAAGCTGGTCCTCAGCCTGCCAGTGAATGTGAGATGTTCCA
AGACAGACAATGCTGAGTGGTCGATTCAAGGAATGACAGCAT
TACCTCCAGATATAGAAAGACCCTATAAAGCAGAACCTTTGG
TGTGTGGCACGTCTTCTTCCTCTTCCCTGCACAGAGATTTCT
CCATCAACTTGCTTGTTTGCCTTCTGCTACTCAGCTGCACGC
TGAGCACCAAGAGCTTG.
```

The amino acid sequence of pGC6, as predicted from the ORF sequence of the GC6 gene is shown below (in the amino to carboxy terminus direction):

(SEQ ID NO: 15)
```
MNSFLSVFRYPDFSFPYFPQDYFTNANRELKKDAQQDYHLEYAMENSTHTIIEFTRELHTCDINDKSITDSTVRVIW
AYHHEDAGEAGPKYHDSNRGTKSLRLLNPEKTSVLSTALPYFDLVNQDVPIPNKDTTYWCQMFKIPVFQEKHHVIKV
EPVIQRGHESLVHHILLYQCSNNFNDSVLESGHECYHPNMPDAFLTCETVIFAWAIGGEGFSYPPHVGLSLGTPLDP
HYVLLEVHYDNPTYEEGLIDNSGLRLFYTMDIRKYDAGVIEAGLWVSLFHTIPPGMPEFQSEGHCTLECLEEALEAE
KPSGIHVFAVLLHAHLAGRGIRLRHFRKGKEMKLLAYDDDFDFNFQEFQYLKEEQTILPGDNLITECRYNTKDRAEM
TWGGLSTRSEMCLSYLLYYPRINLTRCASIPDIMEQLQFIGVKEIYRPVTTWPFIIKSLKQYKNLSFMDAMNKFKWT
KKEGLSFNKLVLSLPVNVRCSKTDNAEWSIQGMTALPPDIERPYKAEPLVCGTSSSSSLHRDFSINLLVCLLLLSCT
LSTKSL.
```

DBH exists in both the dimeric and tetrameric forms, with two copper atoms per monomeric subunit. The four subunits are linked by disulfide bridges into two dimers, which are joined to each other by noncovalent bonds. Copper, molecular oxygen, and ascorbic acid are all essential for DBH activity. DBH expression is inducible by insulin-like growth factor-I (IGF-I), and DBH functions in catacholamine synthesis by converting dopamine to norepinephrine. Norepinephrine is a critical determinant, along with epinephrine, of minute-to-minute neural regulation of local vascular tone and arterial pressure. DBH is involved in the regulation of autonomic outflow at the level of the brain stem and spinal cord and therefore, contemporaneously has a significant influence on cardiac, renal, and vascular function. In the periphery, the effects of norepinephrine generally result in the elevation of blood pressure, and any factor that alters the synthesis of norepinephrine can perturb blood pressure regulation. The inhibition of DBH in rats elicits a dose-dependent decrease in mean arterial blood pressure (Ohlstein et al., 1987 *J. Pharm. Exp. Ther.* 241:554–559).

Analysis of the pGC6 amino acid sequence shows that pGC6, unlike DBH, lacks a signal peptide sequence at the amino terminus, suggesting that pGC6 may be localized to the cytoplasm. GC6 gene products are believed to be involved in regulating and modulating the sympathetic nervous system. GC6 gene products are therefore not only indicative of cellular senescence but also of other diseases or conditions associated with adrenergic dysfunction and aging, such as hypertension and pheochromocytoma.

The present invention provides synthetic and recombinant oligonucleotides and nucleic acids relating to the GC6 gene in a variety of forms, i.e., isolatable, isolated, purified, substantially pure, or incorporated into a cell-free transcription and translation system or a recombinant host cell. Such compounds are useful for a variety of purposes, i.e., as probes or primers, as polynucleotide plasmids and vectors for producing recombinant gene products that alter senescent gene expression in host cells, as restriction fragments useful for creating useful nucleic acids, and as reagents for therapeutic, diagnostic, and other applications. In particular, the invention provides recombinant or synthetic nucleic acids comprising at least about 8 to 10 to 15 to 25 to 100 or more contiguous nucleotides substantially identical or complementary in sequence to a contiguous nucleotide sequence of the human GC6 gene. One such useful nucleic acid of the invention is the ~3 kb XhoI-XbaI restriction fragment of plasmid pCIneoGC6.

The novel oligonucleotide probes and primers of the invention typically comprise nucleotides in a sequence substantially identical or complementary to a sequence of nucleotides in a GC6 gene or gene product to allow specific hybridization thereto in a complex mixture of nucleic acids. The oligonucleotide probes and primers of the invention have useful application in a variety of diagnostic, therapeutic, and other applications. The oligonucleotides of the invention can be used as hybridization probes or PCR primers to detect the presence of GC6 gene products, to diagnose a disease characterized by the presence of an elevated or reduced GC6 mRNA level in cells, to perform tissue typing (i.e., identify tissues characterized by the expression of GC6 mRNA), and the like. Probes can be used to detect GC6-specific nucleotide sequences in a DNA sample, such as for forensic DNA analysis or for diagnosis of diseases characterized by amplification, alteration, and/or rearrangements of the GC6 gene.

The primers and probes of the invention can be used in a variety of diagnostic methods such as to determine relative levels of senescent gene products in tissues. For example, relative levels of GC6 mRNA were determined in various tissues and organs by dot-blot analysis of total RNA (commercially available from Clontech), as described in Example 4, below. The highest levels of GC6 mRNA were detected in fetal and adult kidney, uterus and lung cells. These results were consistent with reverse transcriptase-PCR (RT-PCR) analysis using the primers of the invention:

KJC32, defined by the sequence: 5'-AGCCGAAAAGCCAAGTG-3' (SEQ ID NO. 17), and

KJC33, defined by the sequence: 5'-CCTCCCCAAGTCATCTCAG-3' (SEQ ID NO. 18), as described in Example 3. This RT-PCR analysis showed a 3 to 6-fold higher expression in lung, kidney, and testis than in small intestine, thymus, fetal liver, liver and heart and that the expression levels of GC6 were 4 to 5-fold higher in late passage, senescent BJ cells than in early passage, young BJ cells.

As one example of other useful oligonucleotides of the invention, antisense polynucleotides targetting the GC6 mRNA are provided. Complementary antisense polynucleotides include antisense RNA or DNA oligonucleotides that can hybridize specifically to GC6 mRNA or the GC6 gene and so prevent either transcription of the gene or translation of the mRNA. Antisense polynucleotides of various lengths may be used, although such antisense polynucleotides typically comprise a sequence of at least about 25 consecutive nucleotides that are substantially identical to a naturally occurring GC6 gene or corresponding mRNA sequence. Antisense polynucleotides may be produced from an expression vector comprising a heterologous promoter operably linked to a sequence encoding the antisense oligonucleotide in a transfectant cell or transgenic cell. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments, the antisense polynucleotides comprise methylphosphonate or other synthetic moieties. For general methods relavent to the antisense polynucleotides of the invention, see Antisense RNA and DNA, D. A. Melton, Ed., Cold Spring Harbor Laboratory, Cold Spring Harbor, N.Y. (1988).

Thus, the present invention also provides antisense molecules comprising the nucleic acid sequence complementary to at least a portion of the polynucleotide of SEQ ID NO. 14 or SEQ ID NO: 16. In an alternatively preferred embodiment, the present invention also provides pharmaceutical compositions comprising an antisense molecules complementary in sequence to a sequence of SEQ ID NO. 14 or SEQ ID NO: 16, and a pharmaceutically acceptable excipient and/or other compound (e.g., adjuvant). Such antisense oligonucleotides have application in reducing transcription of the GC6 gene and translation of GC6 mRNA. These antisense oligonucleotides will be administered to patients and cells in which it is desired to reduce the activity or amount of pGC6. In one embodiment, the antisense oligonucleotides of the invention are administered to alter senescent gene expression by reducing the expression of the GC6 gene via transcription or translation inhibition.

Modulation of GC6 gene expression can be obtained by using the antisense molecules (DNA, RNA, PNA, and the like) of the invention to target the control regions of the GC6 gene (i.e., the promoters, enhancers, and introns). Oligonucleotides derived from the transcription initiation site (e.g., between −10 and +10 regions of the mRNA) are often preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules (for a review of recent therapeutic advances using triplex DNA; see Gee et al., in Huber and Carr, Molecular and Immunologic Approaches, Futura Publishing Co, Mt Kisco N.Y. (1994).

Antisense molecules of the invention may be prepared by a wide variety of methods known in the art. These include techniques for chemically synthesizing oligonucleotides, such as solid phase phosphoramidite chemical synthesis. Alternatively, RNA molecules may be generated by in vitro and in vivo transcription of DNA sequences complementary to either strand of the coding sequence of the GC6 gene. Such DNA sequences may be incorporated into a wide variety of vectors with suitable promoters. Alternatively, antisense cDNA constructs that synthesize antisense RNA constitutively or inducibly can be introduced into cell lines, cells or tissues.

The antisense molecules of the invention may be modified to increase intracellular stability and half-life. Such modifications include, but are not limited to, the addition of flanking sequences at the 5' and/or 3' ends of the molecule or the use of phosphorothioate or 2' O-methyl rather than phosphodiesterase linkages within the backbone of the molecule. The use of PNAs and the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases can also increase stability.

In accordance with the present invention, polynucleotide sequences which encode pGC6, or its functional equivalents, may be used in recombinant DNA molecules that direct the expression of pGC6 by appropriate host cells. Recombinant DNA techniques can be employed to engineer bacteria and other easily cultured organisms to uptake a recombinant expression vector. Other methods for introducing vectors into cells or tissues include those methods discussed infra, and which are equally suitable for in vivo, in vitro and ex vivo therapy. In addition, delivery by transfection and by liposomes are quite well known in the art.

The nucleic acid reagents of the invention also include reagents useful in identifying, isolating, and cloning nucleic acids that encode mammalian (i.e., mouse) homologs of the human GC6 gene. Homologous DNA can be readily identified by screening a genomic or cDNA clone library prepared from the mammalian cells of interest, such as a mouse, rat, rabbit, or other cells, i.e., in yeast artificial chromosomes, cosmids, or bacteriophage lambda (e.g., Charon 35), with a polynucleotide probe comprising a sequence of about at least 15 to 30 or more contiguous nucleotides (or their complement) of the human GC6 sequences disclosed herein. Typically, hybridization and washing conditions are performed at varying degrees of stringency according to conventional hybridization procedures. Positive clones are isolated and sequenced. For illustration and not limitation, a full length polynucleotide corresponding to the open reading frame sequences of the GC6 genes can be labeled and used as a hybridization probe to isolate genomic clones from a murine or other mammalian genomic clone or cDNA library (i.e., those available from Promega Corporation, Madison, Wis.).

The nucleic acids of the invention can also be employed to isolate and identify gene products that interact with or bind to GC6 gene products. The yeast "two-hybrid" system (see Chien et al., 1991, Proc. Natl. Acad. Sci. 88:9578) utilizes expression vectors that encode the predetermined polypeptide sequence as a fusion protein and is used to identify protein-protein interactions in vivo through reconstitution of a transcriptional activator (see Fields and Song, 1989 Nature 340:245). Usually the yeast Gal4 transcription protein, which consists of separable domains responsible for DNA-binding and transcriptional activation, serves as the transcriptional activator. Polynucleotides encoding two hybrid proteins, one consisting of the yeast Gal4 DNA-binding domain fused to a polypeptide sequence of a first protein and the other consisting of the Gal4 activation domain fused to a polypeptide sequence of a second protein (either the first or second protein typically is a number of different proteins to be screened for ability to interact specifically with the other protein), are constructed and introduced into a yeast host cell. Intermolecular binding, if any, between the two fusion proteins reconstitutes the Gal4 DNA-binding domain with the Gal4 activation domain, which leads to the transcriptional activation of a reporter gene (e.g., lacZ, HIS3) operably linked to the Gal4 binding site. Typically, the two-hybrid method is used to identify polypeptide sequences that interact with a known protein.

The nucleic acid sequence encoding pGC6 and variants thereof can also be used to generate hybridization probes for mapping the naturally occurring homologous genomic sequence in the human and other genomes. Mapping techniques include in situ hybridization to chromosomal spreads, flow-sorted chromosomal preparations, or artificial chromosome constructs such as yeast artificial chromosomes, bacterial artificial chromosomes, bacterial P1 constructs or single chromosome cDNA libraries as reviewed by Price, 1993, Blood Rev. 7:127, and Trask, 1991, Trends Genet. 7:149), or radiation hybrid panel mapping. Fluorescent in situ hybridization (FISH) of chromosome spreads is described in Verma et al., Human Chromosomes: A Manual of Basic Techniques, Pergamon Press, New York N.Y. (1988). See also, Hudson et al., 1995, Science 270:1945.

Correlation between the location of the sequence encoding human pGC6 on a physical chromosomal map and a specific disease (or predisposition to a specific disease) can delimit the region of DNA associated with the disease. The oligonucleotides of the present invention can also be used to detect differences in gene sequences between normal, carrier or affected individuals. Radiation hybrid panel mapping was used to determine the chromosomal location of the GC6 gene. Hybrid panel mapping entails the use of panels of hybrid cell lines established by using various media in which, for example, one species' cells, such as mouse cells, cannot grow but another species' cells, such as human cells, can. Thus, an individual human chromosome can be probed for the presence of a particular gene, for example, by testing a cell line biochemically for a particular enzyme or immunologically (with an antibody) for a surface antigen; or DNA hybridization techniques may be used to locate a particular DNA sequence. Using gene-specific PCR amplification, the GC6 gene is predicted to lie on the q arm of chromosome 6, closest to the marker D6S413 (lod score 10.8).

Another important application of the oligonucleotide and nucleic acid reagents of the invention relates to the production of recombinant peptides and proteins of the invention.

The peptides and proteins of the invention can be produced by in vitro recombinant DNA techniques, synthetic techniques and in vivo recombination or genetic recombination. Such techniques are generally described in Sambrook et al., Molecular Cloning, A Laboratory Manual, Cold Spring Harbor Press, Plainview N.Y. (1989), and Ausubel et al., Current Protocols in Molecular Biology, John Wiley & Sons, New York N.Y. (1989).

The expression vectors of the invention typically comprise expression control sequences operatively linked to a nucleotide sequence, the coding sequence, encoding amino acids in a sequence identical to a at least a portion of the sequence of amino acids in pGC6. The coding sequence typically encodes at least 6 to 10 amino acids, or encodes all of or at least an active portion of the pGC6, or encodes from 6 to 15 to 20 to 25 to 100 or more contiguous amino acids in a sequence of pGC6, i.e., SEQ ID NO:15, or variant but related sequence.

Useful GC6 variant proteins include fusion proteins, in which all or a portion of pGC6 is fused to peptide or polypeptide that imparts some useful feature, such as a binding site for use in affinity purification, i.e., a polyhistidine tag of about six histidine residues or the maltose binding protein. Preferably, these amino acid sequences occur in the given order of the naturally occurring proteins (in the amino-terminal to carboxy-terminal orientation) but may comprise other intervening and/or terminal sequences; generally such polypeptides are less than about 500 amino acids in length.

These and other expression vectors of the invention have many useful applications, including in therapeutic methods of the invention as gene therapy vectors for modulating senescence in a target cell or tissue. In one embodiment, recombinant pGC6 is produced in a cell to increase the activity or amount of pGC6 in that cell or an organism comprising the cell. The pGC6 produced in this embodiment of the invention has application to the treatment of diseases caused or exacerbated by inadequate production of pGC6. Variants of pGC6 that have pGC6 activity or enhanced, relative to naturally occurring pGC6, activity are also useful in the treatment of such diseases. In another embodiment, a recombinant pGC6 variant that lacks activity or has diminished, relative to naturally occurring pGC6, activity is administered to treat diseases or conditions in which pGC6 activity is causative or contributes to the disease state.

Thus, the gene therapy expression vectors of the invention also include those that encode variants or "muteins" of pGC6, i.e., express proteins that differ from pGC6 by deletion, substitution, and/or addition of one or more amino acids, and the invention also provides such muteins, whether produced by recombinant or synthetic means. As noted above, the gene therapy vectors of the invention may also, however, encode other useful nucleic acids, such as antisense nucleic acids or ribozymes that target GC6 mRNA. The vectors of the invention can also code for the expression of a protein which, when presented as an immunogen, elicits the production of an antibody that specifically binds to pGC6 or cells expressing those proteins. Such antibodies would be desired to treat or prevent diseases characterized by overexpression of pGC6 or where pGC6 contributes to the disease state or condition. Such vectors can also code for a structurally-related protein, such as a pGC6 fragment or analog.

The nucleotide sequence encoding pGC6 is useful when placed in an expression vector for making quantities of protein for therapeutic or other use. The antisense nucleotide sequence of the GC6 gene is useful in vectors designed for gene therapy directed at diseases associated with senescence. Alternatively, pGC6 encoding nucleotide sequences can be used to direct the expression pGC6 in situations where it is desirable to increase the amount of cellular senescence, i.e., when it is desired to facilitate cellular senescence, for example but not limited to, diseases in which the cell type is proliferative to control growth proliferation.

Expression vectors of the invention comprise expression and replication or chromosomal integration signals or elements compatible with the host cell of interest, i.e., sequences that facilitate transcription and translation (expression sequences) of the coding sequences, such that the encoded polypeptide product is produced. Construction of such polynucleotides is generally well known in the art and is described further in Maniatis et al., supra. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication or chromosmal integration of a vector.

A typical eukaryotic expression vector or plasmid of the invention includes a polynucleotide sequence encoding a GC6 polypeptide linked downstream (i.e., in translational reading frame orientation) of a promoter such as the HSV, tk, PGK, metallothionein, or any of a wide variety of other promoters suitable for use in mammalian cells, optionally linked to an enhancer and a downstream polyadenylation site (e.g., an SV40 large T Ag poly A addition site). Expression vectors useful for expressing the recombinant pGC6 of this invention include viral vectors derived from viruses such as retroviruses, herpes viruses, vaccinia viruses, adenoviruses and adeno-associated viruses, i.e., for therapeutic methods; plasmid vectors such as pcDNA1 (Invitrogen, San Diego, Calif.), in which the expression control sequence comprises the CMV promoter; cosmids, and the like. Viral and plasmid vectors are often preferred for transfecting mammalian cells. Expression vectors can be used for delivery of nucleotide sequences (sense or antisense) to the targeted organ, tissue or cell population.

The polynucleotides comprising the full length cDNA sequence and/or its regulatory elements enable sense (Youssoufian and Lodish, 1993, *Mol. Cell. Biol.* 13:98–104) or antisense (Eguchi et al., 1991, *Ann. Rev. Biochem.* 60:631–652) regulation of gene function. Such technology is now well known in the art for other applications, and sense or antisense oligomers, or larger fragments, can be designed from various locations along the coding or control regions of the GC6 gene. In addition, genes encoding pGC6 can be "turned off" or down-regulated by transfecting a cell or tissue with expression vectors that express high levels of a desired pGC6 fragment. Such constructs can flood cells with untranslatable sense or antisense sequences. Even in the absence of integration into the DNA, such vectors may continue to transcribe RNA molecules until all the pGC6 or GC6 mRNA is rendered non-functional. Transient expression can last from a day to a week or up to a month or more with a non-replicating vector, and such transient expression vectors are useful and provided by the present invention.

Once a recombinant expression vector is contained within a host or host cell, mRNA synthesis and translation of that mRNA can produce large quantities of a desired protein for use in, for example, medicine, agriculture, and research. The protein can also be used for making a variety of reagents, such as peptides, antibodies, and labeled proteins. Likewise, an unlimited amount of the pure gene can be obtained by replicating the vector and extracting the DNA from the host cell. Thus, in a preferred embodiment, the recombinant expression vectors of the invention are contained within a host cell. Other host cells provided by the invention include those that comprise GC6-derived recombinant or synthetic peptides or proteins.

A variety of expression vector/host systems may be utilized to contain and express a GC6 protein-encoding sequence. These include, but are not limited to, microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificity and include enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla Calif.) or pSport1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of the sequence encoding pGC6, vectors based on SV40 or EBV may be used with an appropriate selectable marker.

In bacterial systems, a number of expression vectors may be selected depending upon the intended use. For example, when large quantities of pGC6, or GC6 peptides, are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding pGC6 may be ligated into the vector in frame with sequences for the amino-terminal Met and residues of beta-galactosidase so that a hybrid protein is produced (e.g., pIN vectors; Van Heeke and Schuster, 1989, *J. Biol. Chem.* 264:5503–5509). The pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems include heparin, thrombin or factor Xa protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGK may be used. For reviews, see Ausubel et al. (supra), and Grant et al., 1987, *Meth. Enzymol.* 153:516–544.

In cases where plant expression vectors are used, the expression of a sequence encoding pGC6 may be driven by any of a number of promoters. For example, viral promoters such as the 35S and 19S promoters of CaMV (Briton et al., 1984, *Nature* 310:511–514) may be used alone or in combination with the omega leader sequence from TMV (Takamatsu et al., 1987, *EMBO J.* 6:307–311). Alternatively, plant promoters such as the small subunit of RUBISCO (Coruzzi et al., 1984, *EMBO J.* 3:1671–1680; Broglie et al., 1984, *Science* 224:838–843) or heat shock promoters (Winter and Sinibaldi, 1991, *Results Probl. Cell Differ.* 17:85–105) may be used. These constructs can be introduced into plant cells by direct DNA transformation or pathogen-mediated transfection (for reviews of such techniques, see Hobbs and Murry, in McGraw Hill Yearbook of Science and Technology McGraw Hill New York N.Y., pp. 191–196 (1992); or Weissbach, Methods for Plant Molecular Biology, Academic Press, New York N.Y., pp. 421–463 (1988)).

An alternative expression system which could be used to express pGC6 is an insect system. In one such system, *Autographa californica* nuclear polyhedrosis virus (AcNPV) is used as a vector to express foreign genes in *Spodoptera frugiperda* cells or in Trichoplusia larvae. The sequence encoding the pGC6 sequence of interest may be cloned into a nonessential region of the virus, such as the polyhedrin gene, and placed under control of the polyhedrin promoter. Successful insertion of the sequence encoding pGC6 will render the polyhedrin gene inactive and produce recombinant virus lacking coat protein. The recombinant viruses are then used to infect *S. frugiperda* cells or Trichoplusia larvae in which the pGC6 sequence is expressed (Smith et al., 1983, *J. Virol.* 46:584; Engelhard et al., 1994, *Proc. Natl. Acad. Sci.* 91:3224–7).

In mammalian host cells, a number of viral-based expression systems may be utilized. In cases where an adenovirus is used as an expression vector, a sequence encoding pGC6 may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk, 1984, *Proc. Natl. Acad. Sci.,* 81:3655–59). In addition, transcription enhancers, such as the Rous sarcoma virus (RSV) enhancer, may be used to increase expression in mammalian host cells.

Specific initiation signals may also be required for efficient translation of a sequence encoding pGC6. These signals include the ATG initiation codon and adjacent sequences. In cases where the sequence encoding pGC6, its initiation codon and upstream sequences are inserted into an appropriate expression vector, no additional transcriptional or translational control signals may be needed. However, in cases where only the coding sequence, or a portion thereof, is inserted, exogenous transcriptional control signals including the ATG initiation codon must typically be provided. Furthermore, the initiation codon must be in the correct reading frame to ensure translation of the entire coding sequence. Exogenous transcriptional elements and initiation codons can be of various origins, both natural and synthetic. Efficiency of expression may be enhanced by the inclusion of enhancers appropriate to the cell system in use (Scharf et al., 1994, *Results Probl. Cell Differ.* 20:125, and Bittner et al., 1987, *Meth. Enzymol.* 153:516).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Host cells, such as CHO (ATCC: American Type Culture Collection, Rockville, Md., CCL 61 and CRL 9618), HeLa (ATCC CCL 2), MDCK (ATCC CCL 34 and CRL 6253), HEK 293 (ATCC CRL 1573), WI-38 (ATCC CCL 75), have specific cellular machinery and characteristic mechanisms for such post-translational activities and may be chosen to ensure the correct modification and processing of the introduced protein.

For long-term, high-yield production of recombinant proteins, stable expression is preferred. For example, cell lines which stably express pGC6 may be transformed using expression vectors which contain viral origins of replication or endogenous expression elements and a selectable marker gene. Following the introduction of the vector, cells may be allowed to grow for 1–2 days in an enriched media before they are exposed to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus tk or thymidine kinase (Wigler et al., 1977, *Cell* 11:223–32) and aprt or adenine phosphoribosyltransferase (Lowy et al., 1980, *Cell* 22:817) genes which can be employed in tk⁻ or aprt⁻ cells, respectively. Also, antimetabolite, antibiotic, or herbicide resistance can be used as the basis for selection; for example, dhfr which confers resistance to methotrexate (Wigler et al., 1980, *Proc. Natl. Acad. Sci.* 77:3567); npt, which confers resistance to the aminoglycosides neomycin and G-418 (Colbere-Garapin et al., 1981, *J. Mol. Biol.* 150:1); and als or pat, which confer resistance to chlorsulfuron and phosphinotricin acetyltransferase, respectively (Murry, In McGraw Hill Yearbook of Science and Technology, McGraw Hill, New York N.Y., pp 191–196 (1992)), can be employed. Additional selectable genes have been described, for example, trpB, which allows cells to utilize indole in place of tryptophan, or hisD, which allows cells to utilize histinol in place of histidine (Hartman and Mulligan, 1988, *Proc. Natl. Acad. Sci.* 85:8047). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes et al., 1995, *Meth. Mol. Biol.* 55:121).

The recombinant host cells of the invention have application in many useful methods of the invention. For example, the invention provides recombinant host cells for use in screens to identify agents that alter senescent gene expression expression, as well as for a variety of other purposes described more fully below. The recombinant host cells of the invention can also be incorporated into the germ line and/or somatic tissues of transgenic mammals, as well as be administered to mammals for therapeutic purposes.

Thus, genomic clones of a senescent-related gene such as the human GC6 gene, or recombinant versions thereof, including versions that encode mutein GC6 gene products, may be used to construct homologous targeting constructs for generating cells and transgenic nonhuman animals having at least one functionally disrupted (or otherwise altered) allele. Guidance for construction of homologous targeting constructs may be found in the art, including: Rahemtulla et al., 1991, *Nature* 353:180; Jasin et al., 1990, *Genes Devel.* 4:157; Koh et al., 1992, *Science* 256:1210; Molina et al., 1992, *Nature* 357:161; Grusby et al., 1991, *Science* 253:1417; and Bradley et al., 1992, *Bio/Technology* 10:534. See also U.S. Pat. Nos. 5,464,764 and 5,487,992. Transgenic cells and/or transgenic non-human animals may be used to screen for agents that alter senescent gene expression expression. Homologous targeting can be used to generate so-called "knockout" mice, which are heterozygous or homozygous for an inactivated allele. Such knockout mice or other mammals may be sold commercially as research animals for investigation of senescence or other purposes.

Chimeric transgenic mice are derived according to Hogan et al., 1988 Manipulating the Mouse Embryo: A Laboratory Manual, Cold Spring Harbor Laboratory, and Teratocarcinomas and Embryonic Stem Cells: A Practical Approach, E. J. Robertson, ed., IRL Press, Washington, D.C. (1987). Embryonic stem cells are manipulated according to published procedures (PCT patent publication No. 96/22362; Zjilstra et al., 1989, *Nature* 342:435; and Schwartzberg et al., 1989, *Science* 246:799, each of which is incorporated herein by reference).

Additionally, a GC6 cDNA or genomic clone may be used to construct transgenes for expressing polypeptides at high levels and/or under the transcriptional control of transcription control sequences which do not naturally occur adjacent to the gene (or vice-versa, i.e., the promoter of the GC6 gene is positioned in front of a reporter gene for use in screening or other use). For example, but not limitation, a constitutive promoter (e.g., an HSV-tk or pgk (phosphoglycerate kinase) promoter) or a cell-lineage specific transcriptional regulatory sequence (e.g., an CD4 or CD8 gene promoter/enhancer) may be operably linked to a protein encoding polynucleotide sequence to form a transgene (typically in combination with a selectable marker such as a neo gene expression cassette). Such transgenes can be introduced into cells (e.g., ES cells, hematopoietic stem cells, cancer cells), and transgenic cells, cell lines, and transgenic animals may be obtained according to conventional methods therewith.

A variety of methods of purifying recombinantly produced pGC6, variant proteins, and peptides derived from either can be used in accordance with the present invention. In addition, such compounds can be produced by wholly synthetic means. For example, host cells transformed with a nucleotide sequence encoding pGC6 may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing pGC6 encoding sequence can be designed with signal sequences which direct secretion of pGC6 through a prokaryotic or eukaryotic cell membrane. Other recombinant constructions may join the sequence encoding pGC6 to a nucleotide sequence encoding a heterologous polypeptide.

The pGC6 or related variant or peptide may also be expressed as a recombinant protein with one or more additional polypeptide domains added to facilitate protein purification. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and pGC6 is useful to facilitate purification. One such expression vector of the invention provides for expression of a fusion protein comprising the sequence encoding pGC6 and nucleic acid sequence encoding 6 histidine residues followed by thioredoxin and an enterokinase cleavage site. The histidine residues facilitate purification while the enterokinase cleavage site provides a means for purifying pGC6 from the fusion protein. Literature pertaining to vectors containing fusion proteins is available in the art (see e.g., Kroll et al., 1993, DNA Cell. Biol. 12:441–53).

Thus, the present invention also provides methods for producing polypeptides comprising the amino acid sequence of SEQ ID NO: 15. This method comprises the steps of: culturing a host cell under conditions suitable for the expression of the polypeptide of SEQ ID NO: 15; and recovering the polypeptide from the host cell culture.

In addition to recombinant production, fragments of pGC6 may be produced by direct peptide synthesis using solid-phase techniques (See e.g., Merrifield, 1963, J. Am. Chem. Soc. 85:2149). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of pGC6 may be chemically synthesized separately and combined using chemical methods to produce the full length molecule.

The newly synthesized peptide can be substantially purified by preparative high performance liquid chromatography (e.g., Creighton, Proteins, Structures and Molecular Principles, W. H. Freeman and Co, New York N.Y. (1983)). The composition of the synthetic peptides may be confirmed by amino acid analysis or sequencing (e.g., the Edman degradation procedure; Creighton, supra). Additionally the amino acid sequences of pGC6, or any part thereof, may be altered during direct synthesis and/or combined using chemical methods with sequences from other proteins, or any part thereof, to produce a variant polypeptide.

The protein may also have deletions, insertions, or substitutions of amino acid residues that result in a functionally equivalent pGC6 unit. Deliberate amino acid substitutions may be made on the basis of similarity in polarity, charge, solubility, hydrophobicity, hydrophilicity, and/or the amphipathic nature of the residues as long as the biological activity of the pGC6 is retained, if such activity is desired. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine; and phenylalanine, tyrosine.

The present invention provides the peptides and proteins encoded by the GC6 gene, as well as fragments and analogs thereof, in isolatable form from eukaryotic or prokaryotic host cells expressing recombinant pGC6, or from an in vitro translation system, as well as in purified and substantially pure form from synthesis in vitro or by purification from recombinant host cells or by purification of the naturally occurring proteins using antibodies or other reagents of the invention. Methods for expression of heterologous proteins in recombinant hosts, chemical synthesis of polypeptides, and in vitro translation are well known in the art and are described further in Maniatis et al. and Berger and Kimrnmel, supra. Such proteins have application in screens for therapeutic agents, for diagnostic tests, and for other applications.

Because they are expressed differentially between senescent and non-senescent cells, the GC6 gene and gene products serve as markers of cell senescence. Polypeptides having the full or partial amino acid sequence of pGC6 are useful, for example, in the production of antibodies against pGC6 that are useful in the detection of pGC6 in cells.

Useful pGC6 proteins of the invention may include heterologous sequences linked at the amino- or carboxy-terminus, wherein the heterologous sequence(s) confer a functional property to the resultant analog not shared by the native protein. Such analogs are referred to as fusion proteins and for purposes of the present invention typically comprise pGC6 or its analog and an additional peptide or protein moiety. Fusion proteins usefully combine properties of two different polypeptides or proteins, and can be used, for example, to confer a label, such as a polyhistidine polypeptide or a maltose binding protein, useful in affinity isolation of the fusion protein or to protect the fusion protein from degradation inside a cell. The fusion protein may comprise a linker peptide with desired properties, for example, a peptidase site that renders pGC6 or its analog cleavable from the remainder of the fusion protein. The fusion protein can also confer an antigenic epitope to pGC6; antibodies that bind the epitope could then be used to immunoprecipitate the fusion protein for purification or to identify associated proteins.

One such example is the recombinant GS-GC6 fusion protein. This recombinant fusion protein was produced by inserting a restriction fragment from pGC6L into the bacterial expression vector pGEX-5 (Promega) to form the GS-GC6 bacterial fusion protein vector. The DNA sequence and the encoded amino acid sequence of the GS-GC6 bacterial fusion protein vector is shown below (nucleic acid sequences are shown in the 5' to 3' direction; amino acid sequences are shown in the amino to carboxy terminus direction; an * designates a stop codon).

```
                                                              (SEQ ID NO. 19)
AGCTTATCGACTGCACGGTGCACCAATGCTTCTGGCGTCAGGCAGCCATCGGAAGCTGTG      60

GTATGGCTGTGCAGGTCGTAAATCACTGCATAATTCGTGTCGCTCAAGGCGCACTCCCGT     120

TCTGGATAATGTTTTTTGCGCCGACATCATAACGGTTCTGGCAAATATTCTGAAATGAGC     180

TGTTGACAATTAATCATCGGCTCGTATAATGTGTGGAATTGTGAGCGGATAACAATTTCA     240

M   S   P   I   L   G   Y   W   K   I   K   G   L   V   Q     15
CACAGGAAACAGTATTCATGTCCCCTATACTAGGTTATTGGAAAATTAAGGGCCTTGTGC    300

P   T   R   L   L   L   E   Y   L   E   E   K   Y   E   E   H   L   Y   E   R     35
AACCCACTCGACTTCTTTTGGAATATCTTGAAGAAAAATATGAAGAGCATTTGTATGAGC    360
```

```
                                            -continued

D   E   G   D   K   W   R   N   K   K   F   E   L   G   L   E   F   P   N   L       55
GCGATGAAGGTGATAAATGGCGAAACAAAAAGTTTGAATTGGGTTTGGAGTTTCCCAATC                          420

P   Y   Y   I   D   G   D   V   K   L   T   Q   S   M   A   I   I   R   Y   I       75
TTCCTTATTATATTGATGGTGATGTTAAATTAACACAGTCTATGGCCATCATACGTTATA                          480

A   D   K   H   N   M   L   G   G   C   P   K   E   R   A   E   I   S   M   L       95
TAGCTGACAAGCACAACATGTTGGGTGGTTGTCCAAAAGAGCGTGCAGAGATTTCAATGC                          540

E   G   A   V   L   D   I   R   Y   G   V   S   R   I   A   Y   S   K   D   F      105
TTGAAGGAGCGGTTTTGGATATTAGATACGGTGTTTCGAGAATTGCATATAGTAAAGACT                          600

E   T   L   K   V   D   F   L   S   K   L   P   E   M   L   K   M   F   E   D      125
TTGAAACTCTCAAAGTTGATTTTCTTAGCAAGCTACCTGAAATGCTGAAAATGTTCGAAG                          660

R   L   C   H   K   T   Y   L   N   G   D   H   V   T   H   P   D   F   M   L      145
ATCGTTTATGTCATAAAACATATTTAAATGGTGATCATGTAACCCATCCTGACTTCATGT                          720

Y   D   A   L   D   V   V   L   Y   M   D   P   M   C   L   D   A   F   P   K      165
TGTATGACGCTCTTGATGTTGTTTTATACATGGACCCAATGTGCCTGGATGCGTTCCCAA                          780

L   V   C   F   K   K   R   I   E   A   I   P   Q   I   D   K   Y   L   K   S      185
AATTAGTTTGTTTTAAAAAACGTATTGAAGCTATCCCACAAATTGATAAGTACTTGAAAT                          840

S   K   Y   I   A   W   P   L   Q   G   W   Q   A   T   F   G   G   G   D   H      205
CCAGCAAGTATATAGCATGGCCTTTGCAGGGCTGGCAAGCCACGTTTGGTGGTGGCGACC                          900

P   P   K   S   D   L   I   E   G   R   G   I   P   R   N   S   A   R   E   D      225
ATCCTCCAAAATCGGATCTGATCGAAGGTCGTGGGATCCCCAGGAATTCGGCACGAGAGG                          960

Y   F   T   N   A   N   R   E   L   K   K   D   A   Q   Q   D   Y   H   L   E      245
ATTATTTTACAAATGCAAATAGAGAGTTGAAAAAAGATGCTCAGCAAGATTACCATCTAG                         1020

Y   A   M   E   N   S   T   H   T   I   I   E   F   T   R   E   L   H   T   C      265
AATATGCCATGGAAAATAGCACACACACAATAATTGAATTTACCAGAGAGCTGCATACAT                         1080

D   I   N   D   K   S   I   T   D   S   T   V   R   V   I   W   A   Y   H   H      285
GTGACATAAATGACAAGAGTATAACGGATAGCACTGTGAGAGTGATCTGGGCCTACCACC                         1140

E   D   A   G   E   A   G   P   K   Y   H   D   S   N   R   G   T   K   S   L      305
ATGAAGATGCAGGAGAAGCTGGTCCCAAGTACCATGACTCCAATAGGGGCACCAAGAGTT                         1200

R   L   L   N   P   E   K   T   S   V   L   S   T   A   L   P   Y   F   D   L      325
TGCGGTTATTGAATCCTGAGAAAACTAGTGTGCTATCTACAGCCTTACCATACTTTGATC                         1260

V   N   Q   D   V   P   I   P   N   K   D   T   T   Y   W   C   Q   M   F   K      345
TGGTAAATCAGGACGTCCCCATCCCAAACAAAGATACAACATATTGGTGCCAAATGTTTA                         1320

I   P   V   F   Q   E   K   H   H   V   I   K   V   E   P   V   I   Q   R   G      365
AGATTCCTGTGTTCCAAGAAAAGCATCATGTAATAAAGGTTGAGCCAGTGATACAGAGAG                         1380

H   E   S   L   V   H   H   I   L   L   Y   Q   C   S   N   N   F   N   D   S      385
GCCATGAGAGTCTGGTGCACCACATCCTGCTCTATCAGTGCAGCAACAACTTTAACGACA                         1440

V   L   E   S   G   H   E   C   Y   H   P   N   M   P   D   A   F   L   T   C      405
GCGTTCTGGAGTCCGGCCACGAGTGCTATCACCCCAACATGCCCGATGCATTCCTCACCT                         1500

E   T   V   I   F   A   W   A   I   G   G   E   G   F   S   Y   P   P   H   V      425
GTGAAACTGTGATTTTTGCCTGGGCTATTGGTGGAGAGGGCTTTTCTTATCCACCTCATG                         1560

G   L   S   L   G   T   P   L   D   P   H   Y   V   L   L   E   V   H   Y   D      445
TTGGATTATCCCTTGGCACTCCATTAGATCCGCATTATGTGCTCCTAGAAGTCCATTATG                         1620

N   P   T   Y   E   E   G   L   I   D   N   S   G   L   R   L   F   Y   T   M      465
ATAATCCCACTTATGAGGAAGGCTTAATAGATAATTCTGGACTGAGGTTATTTTACACAA                         1680

D   I   R   K   Y   D   A   G   V   I   E   A   G   L   W   V   S   L   F   H      485
TGGATATAAGGAAATATGATGCTGGGGTGATTGAGGCTGGCCTCTGGGTGAGCCTCTTCC                         1740

T   I   P   P   G   M   P   E   F   Q   S   E   G   H   C   T   L   E   C   L      505
ATACCATCCCTCCAGGGATGCCTGAGTTCCAGTCTGAGGGTCACTGCACTTTGGAGTGCC                         1800

E   E   A   L   E   A   E   K   P   S   G   I   P   G   S   T   R   A   A   A      525
TGGAAGAGGCTCTGGAAGCCGAAAAGCCAAGTGGAATTCCCGGGTCGACTCGAGCGGCCG                         1860

S   *                                                                               526
CATCGTGACTGACTGACGATCTGCCTCGCGCGTTTCGGTGATGACGGTGAAAACCTCTGA.                         1920
```

The resulting plasmids were introduced into *E. coli* host bacterial strains, and the cultures were analyzed for the presence of recombinant GS-GC6 fusion protein. Bacterial strains were derived that expressed the recombinant GS-GC6 fusion protein and the resultant protein was purified. The amino acid sequence of the pGS-GC6 fusion protein of the invention is shown below in the amino to carboxy terminus direction.

```
MSPILGYWKIKGLVQPTRLLLEYLEEKYEE      30  (SEQ ID NO. 20)
HLYERDEGDKWRNKKFELGLEFPNLPYYID      60
GDVKLTQSMAIIRYIADKHNMLGGCPKERA      90
EISMLEGAVLDIRYGVSRIAYSKDFETLKV     120
DFLSKLPEMLKMFEDRLCHKTYLNGDHVTH     150
PDFMLYDALDVVLYMDPMCLDAFPKLVCFK     180
KRIEAIPQIDKYLKSSKYIAWPLQGWQATF     210
GGGDHPPKSDLIEGRGIPRNSAREDYFTNA     240
NRELKKDAQQDYHLWYAMENSTHTIIEFTR     270
ELHTCDINDKSITDSTVRVIWAYHHEDAGE     300
AGPKYHDSNRGTKSLRLLNPEKTSVLSTAL     330
PYFDLVNQDVPIPNKDTTYWCQMFKIPVFQ     360
EKHHVIKVEPVIQRGHESLVHHILLYQCSN     390
NFNDSVLESGHECYHPNMPDAFLTCETVIF     420
AWAIGGEGFSYPPHVGLSLGTPLDPHYVLL     450
EVHYDNPTYEEGLIDNSGLRLFYTMDIRKY     480
DAGVIEAGLWVSLFHTIPPGMPEFQSEGHC     510
TLECLEEALEAEKPSGIPGSTRAAAS.       536
```

These and other fusion proteins of the invention can be isolated in accordance with standard procedures and then used to immunize animals, i.e., mouse and rabbits, for the production of polyclonal antisera and monoclonal antibodies, as described in the following section.

The pGC6, analogs, peptides, and polypeptides can also be prepared by chemical synthesis using well known methods. For example, various peptides with amino acid sequences corresponding to sequences of pGC6 can be chemically synthesized in vitro and used to generate antibodies that specifically bind to pGC6. An illustrative peptide of the invention includes the GS-GC6 fusion protein, SEQ. ID NO: 20, which has been chemically synthesized in vitro and used to immunize animals to generate antibodies specific for pGC6.

Such peptides may correspond to structural and functional domains identified by comparison of the nucleotide and/or amino acid sequence data of a gene or protein to public or other sequence databases. Computerized comparison methods can be used to identify sequence motifs or predicted protein conformation domains that occur in other proteins of known structure and/or function. See Proteins, Structures and Molecular Principles, Creighton (ed.), W. H. Freeman and Company, New York (1984), incorporated herein by reference. Methods to identify protein sequences that fold into a known three-dimensional structure are known. See Bowie et al., 1991, *Science* 253:164. Recognized sequence motifs and structural conformations may be used to define structural and functional domains. Computer programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology. Neural network methods, whether implemented in hardware or software, may be used to: (1) identify related protein sequences and nucleotide sequences, and (2) define structural or functional domains in polypeptides. See Brunak et al., 1991, *J. Mol. Biol.* 220:49, incorporated herein by reference.

One important application of the peptides and proteins of the invention is the generation of antibodies that specifically bind to pGC6. The proteins and peptides of the invention can be used to generate antibodies specific for pGC6, or for particular epitopes on those proteins. The pGC6, fragments thereof, or analogs thereof, can be used to immunize an animal for the production of specific antibodies. For the production of antibodies, various hosts, including goats, rabbits, rats, and mice, may be immunized by injection with pGC6 or any portion, fragment or oligopeptide which retains immunogenic properties. Depending on the host species, various adjuvants may be used to increase immunological response. Such adjuvants are commercially available, and include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Monoclonal antibodies to pGC6 can be prepared using any technique which provides for the production of antibody molecules by continuous cell lines in culture. These include but are not limited to the hybridoma technique originally described by Koehler and Milstein, 1975, *Nature* 256:495–497, the human B-cell hybridoma technique (Kosbor et al., 1983, *Immunol. Today* 4:72; Cote et al., 1983, *Proc. Natl. Acad. Sci.* 80:2026–2030) and the EBV-hybridoma technique (Cole et al., Monoclonal Antibodies and Cancer Theraphy, Alan R Liss Inc., New York N.Y., pp. 77–96 (1985)). Antibodies may also be produced by inducing in vivo production in the lymphocyte population or by screening recombinant immunoglobulin libraries or panels of highly specific binding reagents as disclosed in Orlandi et al., 1989, *Proc. Natl. Acad. Sci.* 86: 3833; and Winter and Milstein, 1991, *Nature* 349:293.

For example and without limitation, a recombinantly produced fragment of a pGC6 fusion protein was injected into a rabbit along with an adjuvant following immunization protocols known to those of skill in the art so as to generate an immune response. Specifically, the purified recombinant GS-GC6 fusion protein was injected into rabbits (BABCO) and the resulting serum was tested for reactivity against the fusion proteins by Western blot analysis. Antiserum to the protein was determined to be sensitive and specific.

Alternatively, or in combination with a recombinantly produced polypeptide, a chemically synthesized peptide having an amino acid sequence corresponding to a pGC6 may be used as an immunogen to raise antibodies which bind a pGC6. Immunoglobulins that bind the target protein with a binding affinity of at least about $1 \times 10^6$ $M^{-1}$ can be harvested from the immunized animal as an antiserum, and may be further purified by immunoaffinity chromatography or other means.

Additionally, spleen cells can be harvested from the immunized animal (typically rat or mouse) and fused to myeloma cells to produce a bank of monoclonal antibody-secreting hybridoma cells. The bank of hybridomas can be screened for clones that secrete immunoglobulins that bind the protein of interest specifically, i.e., with an affinity of at least 1×107 M$^{-1}$. A variety of animals may be used to raise antibodies; for example, mice, rats, goats, rabbits, sheep, and chickens may also be employed to raise antibodies reactive with pGC6. Transgenic animals having the capacity to produce substantially human antibodies also may be immunized and used for a source of antiserum and/or for making monoclonal antibody secreting hybridomas.

Thus, the invention provides polyclonal and monoclonal antibodies that specifically bind to pGC6. In particular, the present invention also provides antibodies that binds specifically to a polypeptide comprising at least a portion of the amino acid sequence of SEQ ID NO: 15 or SEQ ID NO. 20. In one embodiment, the present invention provides a pharmaceutical composition comprising at least one antibody, and a pharmaceutically acceptable excipient.

Bacteriophage antibody display libraries may also be screened for phage able to bind peptides and proteins of the invention specifically. Combinatorial libraries of antibodies have been generated in bacteriophage lambda expression systems and may be screened as bacteriophage plaques or as colonies of lysogens. For general methods to prepare antibodies, see Antibodies: A Laboratory Manual, E. Harlow and D. Lane, Cold Spring Harbor Laboratory, Cold Spring Harbor, N.Y. (1988), incorporated herein by reference.

These antibodies can in turn be used to isolate pGC6 from normal or recombinant cells and so can be used to purify the proteins as well as other proteins associated therewith. Antibodies directed against pGC6 are useful in the diagnosis and treatment of conditions and diseases associated with senescence. Such antibodies include, but are not limited to, polyclonal, monoclonal, chimeric, single chain, Fab fragments and fragments produced by a Fab expression library. These antibodies are useful in the detection of pGC6 in samples and in the detection of cells comprising pGC6 in complex mixtures of cells. Such detection methods have application in screening, diagnosing, and monitoring diseases and other conditions associated with aging, such as hypertension, particularly as pGC6 exhibits significant homology to DBH.

For some applications of the antibodies of the invention, such as identifying immuno-crossreactive proteins, the desired antiserum or monoclonal antibody(ies) is/are not monospecific. In these or other instances, it may be preferable to use a synthetic or recombinant fragment of a pGC6 as an antigen rather than the entire protein. More specifically, where the object is to identify immuno-crossreactive polypeptides that comprise a particular structural moiety, it is preferable to use as an antigen a fragment corresponding to part or all of a commensurate structural domain in pGC6.

Cationized or lipidized antibodies reactive with pGC6 can be used therapeutically to treat or prevent diseases of excessive or inappropriate expression of these proteins and the processes regulated thereby. Other methods of the invention are discussed in the following section.

III. Methods to Identify Agents that Modulate Senescebt Gene Expression

One important use of the oligonucleotide and antibody probes of the present invention is in a method for screening compounds to identify compounds that can alter senescent gene expression, which method comprises: (a) contacting said cells with an agent; (b) measuring an amount of a GC6 gene product of said treated cells; (c) comparing said measured amount of said GC6 gene product with a measured amount of said GC6 gene product of a control cell not contacted with said agent; and (d) identifying as agents that alter senescent gene expression in cells as any agent that produces an increased or decreased amount of said GC6 gene product in said treated cells in relative to said control cells.

Any GC6 gene product can be used in the method; for example, GC6 mRNA or pGC6. In addition, the assay or screen can be conducted in combination with analysis of the affect of the agent on other known senescent specific markers such as beta-galactosidase, collagenase, interferon gamma, collagen I, collagen III, elastase, elastin, TIMP3, or IL-Ia, autofluorescence, acridine-orange fluorescence, and telomere length. Thus, while one marker can be used to identify agents that alter senescent gene expression expression, a preferred method is to use a combination of markers.

This screening method identifies compounds with the capacity to reverse, partially reverse, inhibit, or enhance gene expression that is altered as a consequence of senescence. The present invention also encompasses the compounds identified by this method and the use of those compounds to alter gene expression in senescent cells. Such screening can also identify compounds that activate young-specific genes or prevent cells from entering a senescent state. In this method, the oligonucleotide or antibody probes of the invention can serve as indicators of whether a test compound can alter the expression levels of a senescence-related gene.

Compounds ideally suited for testing in this method include compounds identified in primary screens based on other senescent specific markers. However, such testing for other markers can take place before or after screening for agents that modulate GC6 expression. In general, the basic format of the screen is as follows. Cells are cultured in 96-well microtiter plates. After an incubation period, i.e., three days in culture, the medium will be removed and the cells can optionally be assayed for one or more senescence-specific markers, providing a "before treatment" baseline, if desired. The medium will be replaced with fresh medium containing a test agent or its vehicle. The cells will be cultured for an additional period, i.e., two to four days or more in culture, in the presence of the test agent. The cells and/or medium will then be assayed for GC6 gene products ("after treatment" measurement) and compared to non-treated controls.

Compounds found active in the above described screens can then be tested to determine whether the compound inhibits the expression of other senescence-related, specifically old-related, genes or activates the expression of young-related genes, or both. The method can employ Northern analysis to examine the effects of the lead compounds on panels of genes that show altered expression or abundance in senescence. Based on the results of this screen, one can determine which compounds normalize the expression of those genes that are altered in senescence and contribute to age-related pathologies. Furthermore, it will be possible to determine the level at which the compound acts to reverse the pattern of altered expression. Complete reversal to a young pattern of gene expression would suggest that a single common mechanism is involved. Reversal of defined groups of genes would be indicate that several mechanisms are operating and that each is affecting a different set of genes. A compound may also act to modulate the activity of individual genes. This information will in turn influence primary screening strategy. If, for example, all active compounds seem to reverse the altered expression of batteries of genes, or of only individual genes, then the screen can be expanded so that many more markers, including members from each of the putative batteries, if appropriate, are included.

Cell-based screens have traditionally been labor intensive and so have not often been used for high-throughput screening. However, the present method is amenable to high-throughput screening. Liquid handling operations can be performed by a Microlab 2000™ pipetting station (Hamilton Instruments). Other equipment needed for the screen (e.g., incubators, plate washers, plate readers) can either be adapted for automated functioning or purchased as automated modules. Movement of samples through the assay can be performed by an XPTM robot mounted on a 3 m-long track (Zymark).

In addition, pGC6 or its catalytic or immunogenic fragments or oligopeptides thereof can be used for screening therapeutic compounds in any of a variety of other drug screening techniques. In particular, the GC6 gene product is a useful target for therapeutic intervention because that gene product is involved in disease pathology and a change in its expression parallels that of gene products involved in disease pathology. One can quantitate changes in the level of gene expression caused by a compound using high-throughput screening techniques. The GC6 gene product or fragment thereof employed in such a test may be free in solution, affixed to a solid support, born on a cell surface, or located intracellularly. The formation of binding complexes, between the gene product and the agent being tested, may be measured.

One such screening method uses in situ hybridization to quantitate the expression levels of mRNA before and after treatment of the cells with an agent. Labeled RNA or DNA that is complementary to a specific mRNA, e.g., GC6 mRNA, is prepared. Cells or tissue slices are briefly exposed to heat or acid, which fixes the cell contents, including the mRNA, in place on a glass slide, the fixed cell or tissue is then exposed to the labeled complementary RNA for hybridization. Removal of unhybridized labeled RNA and coating the slide with a photographic emulsion is followed by autoradiography to reveal the presence and even the location of specific mRNA within individual cells.

Alternatively, the amount of mRNA in a sample can be measured and quantitated by competition hybridization. In this method, a measured sample of a specific labeled RNA is exposed to just enough complementary DNA to completely hybridize with it, and a sample of unlabeled RNA is then added. If the unlabeled RNA sample contains the same sequence as the labeled RNA, they compete for the DNA, increasing the ratio of unlabeled to labeled samples decreases the amount of labeled RNA hybridized. The extent to which this takes place is a measure of the amount of competing RNA in the unlabeled sample. Using active agents (agents previously determined to alter expression of senescent genes other that GC6), one can determine whether and at what level coordinate modulation of gene expression occurs (i.e., does the compound affect senescence-related gene globally, in groups, or individually), and if by group, to which group an individual gene belongs.

Another technique for drug screening which may be used for high throughput screening of compounds having suitable binding affinity to the pGC6 is described in detail for other applications in "Determination of Amino Acid Sequence Antigenicity" by Geysen, PCT Application 84/03564, published on Sep. 13, 1984, incorporated herein by reference. In summary, large numbers of different small peptide test compounds are synthesized on a solid substrate, such as plastic pins or some other surface. The peptide test compounds are reacted with fragments of pGC6 and washed. Bound pGC6 is then detected by methods well known in the art. Substantially purified pGC6 can also be coated directly onto plates for use in the aforementioned drug screening techniques. Alternatively, non-neutralizing antibodies can be used to capture the peptide and immobilize it on a solid support.

Through these screens, libraries of synthetic organic compounds, natural products, peptides, and oligonucleotides can be evaluated for their capacity to alter senescent gene expression that contributes to the disease process. Specifically, compounds can be identified that will down-regulate genes that are up-regulated during senescence or, conversely, will increase the expression of genes that are down-regulated during senescence. Active compounds can be optimized, if desired, via medicinal chemistry. Initially, one can define a pharmacophore(s) using modern computational chemistry tools representative of the structures found to be active in the high throughput screens. Once a consensus pharmacophore is identified, one can design focused combinatorial libraries of compounds to probe structure-activity relationships. Finally, one can improve the biopharmaceutical properties, such as potency and efficacy, of a set of lead structures to identify suitable compounds for clinical testing.

IV. Methods to Identify, or Distinguish Between, Senescent and Non-Senescent Cells In another aspect, the present invention provides diagnostic methods for identifying or distinguishing between senescent and young (also designated herein as quiescent, presenescent, or non-senescent) cells in tissues or in culture. One such method comprises contacting a GC6 gene product within a cell or tissue with an agent that binds specifically to said GC6 gene product under conditions such that said agent and said GC6 gene product bind to one another; determining whether specific binding has occurred; and correlating the presence of senescent and non-senescent cells with the occurrence of binding.

The present invention further provides methods for the detection of pGC6 in a biological sample comprising the steps of: providing a biological sample suspected of expressing human pGC6; and at least one antibody that binds specifically to at least a portion of the amino acid sequence of SEQ ID NO: 15 or SEQ ID NO. 20; combining the biological sample and antibody(ies) under conditions such that an antibody:protein complex is formed; and detecting the complex, wherein the presence of the complex correlates with the expression of the protein in the biological sample. Thus, the present invention provides novel methods and reagents for identifying senescent cells in tissue or culture, which methods generally comprise determining whether a cell expresses a senescence-related gene product, which can include a mRNA or other RNA or a protein, and correlating the presence of that gene product with the state of senescence of the cell or tissue.

Typically, such methods will be practiced using oligonucleotide probe hybridization to the mRNA of the cell, or antibody binding to pGC6 protein either in situ or in a cell extract, quantitating the amount of hybridization or binding, and comparing that amount to a standard or control, such as the amount observed in an untreated young or senescent cell. In one such method, probes specific for the mRNA corresponding to a senescence-related gene are immobilized on a membrane or filter. Then, the cells of interest are cultured under conditions conducive to gene expression and flash-frozen. The cells are then thawed in the presence of a labeled mRNA or protein precursor, so that the label is incorporated into transcripts or proteins that were being transcribed or translated when the cells were frozen. The labeled mRNA or protein is then harvested from the cell and hybridized or bound to the immobilized probes on the filter. The pattern of hybridization or binding will identify whether senescence-related genes are being expressed by the cell. Probes, as described above, specific for GC6 gene products can be used or other probes specific for GC6 gene products can be made by one of skill in the art as provided by the present invention.

The present invention also provides methods for detecting the presence of nucleotide sequences encoding at least a portion of pGC6 in a biological sample, comprising the steps of, providing: a biological sample suspected of containing nucleic acid corresponding to the nucleotide sequence set forth in SEQ ID NO. 14 or SEQ ID NO: 16; the polynucleotide of SEQ ID NO. 14 or SEQ ID NO: 16 or fragment(s) thereof; combining the biological sample with the polyucleotide under conditions such that a hybridization complex is formed between the nucleic acid and the nucleotide; and detecting the hybridization complex.

In one embodiment of the method the nucleic acid corresponding to the nucleotide sequence of SEQ ID NO. 14 or SEQ ID NO: 16 is ribonucleic acid, while in an alternative embodiment, the nucleotide sequence is deoxyribonucleic acid. In yet another embodiment of the method the detected hybridization complex correlates with expression of the polynucleotide of SEQ ID NO. 14 or SEQ ID NO: 16 in the biological sample. Other identification methods of the invention and diagnostic applications are described below.

The expression of pGC6 in cell lines can be used as a diagnostic for identifying senescent cells and is useful in the diagnosis of diseases associated with senescence and aging. The oligonucleotides of the invention may be used in hybridization protocols to diagnose the induced expression of messenger RNA sequences early in the disease process. Such techniques often employ signal or target amplification, such as PCR, LCR, TAS, 3SR, b-DNA, tyramide signal amplification, and the like. Likewise the protein can be used to produce antibodies useful in ELISA assays or a derivative diagnostic format. Such diagnostic tests allow different classes of senescent cells that exacerbate or induce diseases associated with aging to be distinguished and thereby facilitate the selection of appropriate treatment regimens.

The methods of the invention are especially useful in conjunction with therapeutic regimes and strategies. For example, one aspect of the invention is to provide methods for detecting polynucleotide sequences, including genomic sequences encoding variant pGC6 proteins, to identify the senescent (or young) cells in a tissue sample or to identify cells that produce a disease-causing pGC6 variant protein. The specificity of the probe, whether it is made from a highly specific region (e.g., 10 unique nucleotides in the 5' regulatory region), or a less specific region (e.g., especially in the 3' region), and the stringency of the hybridization or amplification (maximal, high, intermediate or low) will determine whether the probe identifies only naturally occurring pGC6 or variant sequences.

By appropriately labeling the probe for detection (e.g., with a fluorescent molecule or a molecule that serves as a binding partner for another molecule), one can label the senescent (or young) cells in a tissue and then separate the young from the senescent cells. In addition, a detectable reagent (e.g., a contrast molecule for magnetic resonance imaging) can be attached to an antibody or other substance which is specific for a GC6 senescence-related gene product, and can specifically label senescent cells. With such a preparation of cells enriched for either the young or senescent phenotype, one can then perform many useful procedures, including reintroduction of young cells into a host or treatment of senescent cells for reintroduction to the host.

Polynucleotide sequences encoding pGC6 also may be used for the diagnosis of conditions or diseases with which the abnormal expression of pGC6 is associated. For example, polynucleotide sequences encoding human pGC6 may be used in hybridization or PCR assays of fluids or tissues from biopsies to detect pGC6 expression. Such qualitative or quantitative methods may include Southern or Northern analysis, dot blot or other membrane-based technologies; PCR technologies; dip stick, pin, chip and ELISA technologies. All of these techniques are well known in the art for other purposes and are the basis of many commercially available diagnostic kits.

The oligonucleotide or antibody probe may be labeled by methods known in the art, such as by a variety of reporter groups, including commercially available radionucleotides such as $^{32}P$ or $^{35}S$, or enzymatic labels such as alkaline phosphatase coupled to the probe via avidin/biotin coupling systems, and the like, and added to a fluid or tissue sample from a patient under conditions suitable for the formation of hybridization or binding complexes. After an incubation period, the sample is washed with a compatible fluid which optionally contains a dye (or other label requiring a developer) if the probe has been labeled with an enzyme. After the compatible fluid is rinsed off, the dye is quantitated and compared with a standard. If the amount of dye in the biopsied or extracted sample is significantly elevated over that of a comparable control sample, the probe has bound to GC6 gene products in the sample, and the presence of elevated levels of the gene product in the sample indicates the presence of the associated disease. Alternatively, the loss of expression of GC6 gene products in a tissue which normally expresses them indicates the reversal of senescence or an associated disease state.

Particular pGC6 antibodies are useful for the diagnosis of conditions or diseases characterized by expression of pGC6, or in assays to monitor patients being treated with agonists or inhibitors (including antisense transcripts) of GC6 gene expression. Diagnostic assays for GC6 gene expression include methods utilizing the antibody and a label to detect pGC6 in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above. In particular, the present invention is useful for diagnosis of human disease, although it is contemplated that the present invention will find use in the veterinary arena as well.

A variety of protocols for measuring pGC6 using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on pGC6 is preferred, but a competitive binding assay may be employed. These assays are described, among other places, in Maddox et al., 1983, *J. Exp. Med.* 158:1211.

Such assays may also be used to evaluate the efficacy of a particular therapeutic treatment regime in animal studies, in clinical trials, or in monitoring the treatment of an individual patient. To provide a basis for the diagnosis of disease, a normal or standard profile for human pGC6 expression is usually established. This is accomplished by combining body fluids or cell extracts taken from normal subjects, either animal or human, with pGC6, under conditions suitable for hybridization or amplification. Standard hybridization may be quantified by comparing the values obtained for normal subjects with a dilution series of human pGC6 run in the same experiment where a known amount of substantially purified human pGC6 is used. Standard values obtained from normal samples may be compared with values obtained from samples from patients affected by senescence induced or exacerbated diseases. Deviation between standard and subject values can establish the presence of a disease state. In addition, the deviation can indicate, within a disease state, a particular clinical outcome.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Additionally, methods which may be used to quantitate the expression of a particular molecule include radiolabeling (Melby et al., 1993, *J. Immunol. Meth.* 159:235–44) or biotinylating (Duplaa et al., 1993, *Analyt. Biochem.* 229–36) nucleotides, co-amplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition.

V. Therapeutic Applications and Pharmaceutical Compositions

In another aspect of the invention the oligonucleotides, proteins, antibodies, and pGC6 agonists, antagonists, or inhibitors, are employed to inhibit or reverse senescent gene expression expression and to treat age-related disease induced or exacerbated by cellular senescence. Those of skill in the art will recognize that the senescence-related genes and gene products of the invention provide a wide array of such agents that can be used to target or direct therapeutic reagents to young or senescent cells. In one embodiment, antisense oligonucleotides, can be targeted to senescence-specific genes. Such antisense oligonucleotides can be comprised of ribonucleic acids, deoxyribonucleic acids, modified nucleic acids, or mixtures.

In addition, it will be appreciated that therapeutic benefits from treatment of a disease or disease condition induced or exacerbated by senescence can be realized by combining an agent of the invention which alters the senescent genotype or phenotype with other agents. Thus, in its therapeutic applications, the present invention also relates to pharmaceutical compositions which may comprise GC6 nucleotides, proteins, antibodies, agonists, antagonists, or inhibitors, alone or in combination with at least one other agent such as another drug or a stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipient(s), adjuvants, and/or pharmaceutically acceptable carriers.

The choice of such combinations will depend on various factors including, but not limited to, the type of disease, the age and general health of the patient, the aggressiveness of disease progression, and the ability of the patient to tolerate the agents that comprise the combination. In addition, in some cases it may be advisable to combine a modulating agent of senescent gene expression expression of the invention with one or more agents that treat the side effects of a disease, e.g., an analgesic, or agents effective to stimulate the patient's own immune response (e.g., colony stimulating factor).

In another embodiment, the present invention includes compounds and compositions in which a modulating agent of the senescent phenotype is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into diseased cells with greater specificity. Thus, the active form of the cytotoxic agent (ie., the free form) will be present only in cells targeted by the antibody. Of course, the modulating agents of the senescent phenotype of the invention may also be combined with monoclonal antibodies that have therapeutic activity against pGC6.

In general, a suitable effective does of a compound of the invention will be in the range of 0.001 to 1000 milligram (mg) per kilogram (kg) of body weight of the recipient per day, preferably in the range of 0.001 to 100 mg per kg of body weight perday, more preferrably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day. These subdoses can be administered as unit dosage form, for example, containing 5 to 10,000 mg, preferably 10 to 1000 mg of active ingredient per unit dosage form. Preferably, the dosage is present once per day at a dosing at least equal to TID.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., location of the disease, age, weight, and gender of the patient, diet, time and frequency of administration, drug combination(s), reaction sensitivities, and tolerance/response to therapy). Long acting pharmaceutical compositions might be administered every 3 to 4 days, every week, or once every two weeks depending on half-life and clearance rate of the particular formulation. General guidance as to particular dosages and methods of delivery for other applications is provided in the literature (see U.S. Pat. Nos. 4,657,760; 5,206,344; and 5,225,212, herein incorporated by reference). Those skilled in the art will typically employ different formulations for oligonucleotides and gene therapy vectors than for proteins or their inhibitors. Similarly, delivery of polynucleotides or polypeptides will be specific to particular cells, conditions, locations, and the like.

The compositions used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., Remington's Pharmaceutical Science, Mack Publishing Co.; Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one agent which alters the GC6 senescent genotype of this invention in a therapeutically or pharmaceutically effective dose together with one or more pharmaceutically or therapeutically acceptable carriers and optionally other therapeutic ingredients. Various considerations for preparing such formulations are described, e.g., in Goodman and Gilman's Pharmacological Bases of Therapeutics, 8th Ed., Pergamon Press (1990); and Remington's supra, each of which is incorporated herein by reference. Methods for administration are discussed therein, e.g., for oral, intravenous, intraperitoneal, intramuscular, and other forms of administration.

Typically, methods for administering pharmaceutical compositions will be either topical, parenteral, or oral. Oral administration is a preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be placed directly onto the backing material or can be applied to the skin to form an adherent coating. See, e.g., U.S. Pat. Nos. 4,310,509; 4,560,555; and 4,542,012.

In other embodiments, the compounds of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,5005,891; 3,843,480; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a poly-urethane foam. The drug, and enhancers, vehicles, stabilizers, and the like are combined with the foam precursors. The foam is allowed to cure to produce a tack, elastomeric matrix which can be directly affixed to the backing material. See, e.g., U.S. Pat. Nos. 4,542,013; 4,460,562; 4,466,953; 4,482,543; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and cremes may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases associated with the skin.

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds or agents of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a senescent modulating agent of the invention would be enhanced, one can select a composition for delivery to a mucosal membrane.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example, as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solutions or suspension in liquid prior to injection, or as emulsions. Suitable excipients are, for example, water, buffered water saline, dextrose, glycerol, ethanol, or the like. These compositions will be sterilized by conventional, well know sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as, for example, sodium acetate, sorbitan monolaurate, and triethanolamine oleate.

Another method of parenteral administration employs the implantation of a slow-release or sustained-release system, such that a constant level of dosage is maintained. See, e.g., U.S. Pat. No. 3,710,795, incorporated herein by reference.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosages forms are known and will be apparent to those skilled in this art; for example, see Remington's, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of the active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Therapeutic efficacy and toxicity of such compounds can be determined by standard pharmaceutical procedures in cell cultures or experimental animals (e.g., ED50, the dose therapeutically effective in 50% of the population; and LD50, the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

In addition to internal (in vivo) administration, the compounds and compositions of the invention may be applied ex vivo to achieve therapeutic effects, as, for example, in the case of a patient suffering from AIDS. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agents for longer periods or at higher concentration than otherwise available.

Once improvement of the patient's conditions has occurred, a maintenance dose is administered, if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

As will be apparent to those of skill in the art upon reading of this disclosure, the present invention provides valuable methods, compounds, and compositions relating to cellular senescence. It is contemplated that these compounds, for example, antisense molecules capable of reducing the expression of GC6 gene products can be used as therapeutic molecules to treat age-related diseases associated with the expression of GC6. Likewise, antibodies directed against GC6 and capable of neutralizing the biological activity of this gene also may be used as therapeutic molecules to treat age-related diseases such as, for example, hypertension. Thus, the above description of necessity provides a limited and merely illustrative sampling of specific methods, compounds, and compositions and should not be construed as limiting the scope of the invention. Other features and advantages of the invention will be apparent from the following examples and claims.

EXAMPLES

The following examples are provided to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); mg (micrograms); ng (nanograms); l or L (liters); rnl (milliliters); ml (microliters); cm (centimeters); mm (millimeters); μm (micrometers); nm (nanometers); °C. (degrees Centigrade); dNTP (deoxyribonucleotide); dH2O (distilled water); DDT (dithiothreitol); PMSF (phenylmethylsulfonyl fluoride); TE (10 mM Tris HCl, 1 mM EDTA, approximately pH 7.2); KGlu (potassium glutamate); SSC (salt and sodium citrate buffer); SDS (sodium dodecyl sulfate); and PAGE (polyacrylamide gel electrophoresis). Although any methods and materials similar or equivalent to those described herein can be used in the practice or testing of the present invention, preferred methods and materials are described.

Example 1

Standard Mehtods in Molecular Genetics

Standard techniques are used for recombinant nucleic acid methods, polynucleotide synthesis, in vitro polypeptide synthesis, microbial culture and transformation (e.g., electroporation), and the like. Generally enzymatic reactions and purification steps using commercially available starting materials are performed according to the manufacturer's specifications. The techniques and procedures are generally performed according to conventional methods in the art and various general references (see, generally, Sambrook et al. Molecular Cloning: A Laboratory Manual, 2d ed., Cold Spring Harbor Laboratory Press, Cold Spring Harbor, N.Y. (1989), incorporated herein by reference) referenced herein.

Oligonucleotides can be synthesized on an Applied Bio Systems or other commercially available oligonucleotide synthesizer according to specifications provided by the manufacturer. Polynucleotide primers may be prepared using any suitable method, such as, for example, the phosphotriester and phosphodiester methods, or automated embodiments thereof. In one such automated embodiment, diethylphosphoramidites are used as starting materials and may be synthesized as described by Beaucage et al., 1981 *Tetrahedron Letters* 22:1859, and U.S. Pat. No. 4,458,066.

Methods for PCR amplification are known in the art (PCR Technology: Principles and Applications for DNA Amplification, Ed. Erlich, Stockton Press, New York, N.Y. (1989); PCR Protocols: A Guide to Methods and Applications, eds. Innis, Gelfland, Sninsky, and White, Academic Press, San Diego, Calif. (1990); Mattila et al., 1991, *Nucleic Acids Res.* 19:4967; Eckert and Kunkel, 1991, *PCR Methods and Applications* 1:17; and the U.S. Patents noted above. Optimal PCR and hybridization conditions will vary depending upon the sequence composition and length (s) of the targeting polynucleotide(s) primers and target(s) employed, and the experimental method selected by the practitioner. Various guidelines may be used to select appropriate primer sequences and hybridization conditions (see, Sambrook et al., supra). Generally PCR is carried out in a buffered aqueous solution, preferably at a pH of 7–9, most preferably about 8. The deoxyribonucleoside triphosphates dATP, dCTP, dGTP, and TTP are also added to the synthesis mixture in adequate amounts, and the resulting solution is heated to about 85–100° C. for about 1 to 10 minutes, preferably from 1 to 4 minutes. After this heating period, solution is allowed to cool to about 20–40° C., for primer hybridization. To the cooled mixture is added an agent for polymerization, and the reaction is allowed to occur under conditions known in the art. This synthesis reaction may occur at from room temperature up to a temperature just over which the agent for polymerization no longer functions efficiently. Thus, for example, if a heat-labile DNA polymerase is used as the agent for polymerization, the synthesis temperature is generally no greater than about 45° C. The agent for polymerization may be any compound or system that will function to accomplish the synthesis of primer extension products, including enzymes. Suitable enzymes for this purpose include, for example, *E. coli* DNA polymerase I or the Klenow fragment thereof, Taq DNA polymerase, and other available DNA polymerases.

The newly synthesized strand and its complementary nucleic acid strand form double-stranded molecules used in the succeeding steps of the process. In the next step, the strands of the double-stranded molecule are separated using any of the procedures described above to provide single-stranded molecules. The steps of strand separation and extension product synthesis can be repeated as often as needed to produce the desired quantity of the specific nucleic acid sequence. The amount of the specific nucleic acid sequence produced will accumulate in an exponential fashion.

Enhanced differential display of subtracted cDNA involves PCR amplification with 5' arbitrary primer(s) and a 3' oligo dT primer with two randomized bases at the 3' end, recovery of bands identified as containing cDNA corresponding to differentially expressed mRNAs, and PCR amplification, sequencing, and/or cloning of the bands identified. Add 1 μl of one 5' primer (20 μM stock) or two 5' primers (half of each) or 1.2 μl of one 5' primer (1 μl) and one 3' primer (0.2 μl) to the tube. Add 1 μl of subtracted DNA to the same tube. To this mixture, add 8 μl of cocktail mix containing 1 μl of 10× PCR buffer for Pfu polymerase (commercially available), 1 μl of dNTP (2.5 mM each), 0.3 mM alpha-$^{32}$P-dATP, 0.1 μl of Taq polymerase, 0.2 μl of Pfu polymerase (Stratagene), 0.02 μl of T4 gene 32 protein (Boehringer Mannheim), and 5.38 μl water. Overlay one drop of mineral oil, and PCR amplify for 4 cycles at 94 degrees C. for 45 sec., 39 degrees C. for 1 min., and 72 degrees C. for 1 min., and then 22 cycles at 94 degrees C. for 45 sec., 60 degrees C. for 1 min., and 72 degrees C. for 1 min., with a final extension for 5 min. at 72 degrees C. About 5 μl of formamide/dye is added to the PCR product, and the products are denatured at 95 degrees C. for 2–3 min. and loaded onto a prewarmed 6% polyacrylamide sequencing gel, which is run at 1900 to 2000 constant voltage (do not allow current to reach 50 mA) until the xylene cyanol dye is one inch from the bottom of the gel. The gel is dried under vacuum at 80 degrees C. for 45 min. and exposed to PhosphorImager™ screen (for notebook record) and/or then to X-ray film at room temperature for one or two days (tape the gel to the film and punch three holes at the three corner of the gel and film for easy identification of bands).

Differentially expressed gene fragments appear as bands on the screen or film that are present in the lanes on the gel corresponding to the cDNA of the tester cells but present at lower levels or absent from the lanes corresponding to the cDNA of the control lanes. The bands can be recovered from the gel by first aligning the gel with the film or screen (based on the three holes and marks) and then excising the bands of interest with a razor blade and transferring the gel slice to an Eppendorf™ tube. Rinse the razor blade between each cutting operation to avoid cross contamination. To remove the urea and paper backing used with sequencing gels without substantial loss of the desired DNA, add about 900 μl of TE buffer to the tube containing the gel slice, incubate the tube at room temperature for 10 min., and then remove and discard the paper and TE buffer. To prepare a solution of the desired DNA from the gel slice, the gel slice is suspended in 40 μl of TE buffer containing 100 mM NaCl and heated for 10 min. at 95–98 degrees C. The liquid is collected (a short centrifugation collects the liquid at the bottom of the tube) and serves as a source of the desired DNA.

This DNA can be PCR-amplified by placing 1–3 μl of recovered DNA in a 50 μl total reaction volume in a reaction mixture containing 6 μl of total primer(s), 5 μl of 10× PCR buffer for Pfu polymerase, 6 μl of dNTP (2.5 mM each), 0.25 μl of Taq polymerase, 0.5 μl of Pfu polymerase, 0.05 μl of T4 gene 32 protein, and water. The PCR is performed for 25 cycles at 94 degrees C. for 45 sec., 60 degrees C. for 1 min., and 72 degrees C. for 1 min., with a 5 min. extension at 72 degrees C. at the end of the last cycle. The PCR products can be stored or further processed, i.e., subcloned and sequenced.

Example 2

GC6 Senescence-Related Gene Expression Screen

To determine the effect of a compound on the expression levels of a GC6 gene product, such as mRNA or pGC6, according to the method of the present invention, cells are seeded at 10,000 to 20,000 cells/plate in DMEM medium plus 10% Bovine Calf Serum (BCS) and grown in a 10 or 15 cm plate. In a preferred embodiment, senescent fibroblast lines derived from human foreskin (BJ cells) are used at Passage Doubling Level (PDL) 92. Other cells, in the appropriate media, can also be used. After 6 hours, the medium is removed and replaced with DMEM plus 0.5% BCS. After 3 days, the medium is replaced with fresh medium. One plate is then incubated with the test compound, and another plate is incubated with the compound test vehicle alone. In a preferred embodiment, 2 μl of agent dissolved in DMSO (1 μM final concentration), or of DMSO alone, are added to 200 μl of medium. Other volumes, vehicles, and compound concentrations can also be used. In addition, mixtures of compounds, rather than single compounds, can be added to the cells.

After four days of incubation, the cells are lysed in GITC (guanidium isothiocyanate), and either mRNA or pGC6 is analyzed. The RNA can analyzed with the senescence-related gene probes of the invention by Northern analysis or by other suitable methods, such as RT-PCR. The results of this analysis will indicate the efficacy of the compound in altering the mRNA expression level on the GC6 senescence-related gene. In, a preferred embodiment, the expression levels of at least one additional, and preferably 3 to 5 to 10 to 20 or more, senescence-related genes will be determined. In a similar manner, quantitative levels of pGC6 can be determined by the use of pGC6 specific antibodies of the invention.

Thus, agents are tested to determine whether a specific agent alters the expression of the young- and old-specific senescence-related genes identified by EDD and in the scientific literature. If a compound has the effect of complete reversal to a young pattern of gene expression, then the compound impacts a single common mechanism driving cell senescence. Reversal of defined groups of genes indicates that several mechanisms are operating in senescence and that different mechanisms can affect different panels of genes. A compound may also act to modulate the activity of an individual gene, suggesting the absence of a common mechanism.

An alternative screen for compounds that alter the expression of senescence-related gene involves the use of a genetic construct comprising a promoter of a senescence-related gene positioned for expression of a coding sequence from a reporter gene, such as an alkaline phosphatase gene, the expression of which can be efficiently and readily monitored. Such a construct would be used to generate stable transfectants in very early passage cells, such as dermal fibroblasts, and then the cells could be used at any stage up to and including senescence to identify agents that up or down-regulate the expression of the reporter gene.

Example 3

RT-PCR Method to Determine GC6 mRNA Levels in Various Tissues

One can detect GC6 mRNA by an RT-PCR protocol. First, cDNA synthesis is carried out by mixing together, in an appropriate tube: 1 μg total RNA; 1 μg random hexamer or GC6-specific primer; and deionized water to 10 μl. The tube is heated to 95° C. for 10 seconds and then placed immediately on ice.

Then, 4 μl of first strand buffer (Promega); 2 μl of 0.1 M DTT; 1 μl of 10 mM dNTPs; 1 μl of RNAse Guard (Pharmacia); and 1 μl of SuperScript II™ Reverse Transcriptase buffer (Promega) are added, and the reaction is incubated at 42° C. for 1 hour. The reaction is stopped by heating the mixture to 95° C. for 10 minutes.

The PCR reaction is carried out by adding, in an appropriate tube: 1, 3, or 10 μl of the above cDNA reaction mixture; 3 μl of 10× AmpliTaq™ buffer (Perkin-Elmer) 1.8 μl of 25 mM MgCl$_2$; 1.5 μl of 10 μM KJC32 primer; 1.5 μl of 10 μM KJC33 primer; 0.3 μl of AmpliTaq™ polymerase (Perkin-Elmer); 3 μl of 10× dNTP mix (2 mM each of dGTP, dCTP, dCTP, and dTTP, 0.2 mM of dATP); 0.3 μl alpha-$^{32}$P-dATP (3000 Ci/mMol; NEN-Dupont) and deionized water to 30 μl. The tube is then placed in a thermal cycler programmed to perform 25 cycles of 94° C. for 10 seconds; 55° C. for 10 seconds; and 72° C. for 60 seconds.

For comparative purposes, one can perform parallel reactions in which a gene expressed at a known level or a constitutively expressed gene, i.e., 28S RNA, is amplified; the number of cycles of PCR amplification can be adjusted in such instances, i.e., for 28S RNA, the PCR amplificantion may be performed for only 7 cycles. Suitable primers for PCR amplification of 28S RNA include primer 28SF, defined by the sequence: 5' GCTAAATACCGGCAC-GAGAC CGATAG -3' (SEQ ID NO. 21), and 28SR, defined by the sequence: 5' GGTTTCACGCCCTCT-TGAACTCTCT C-3' (SEQ ID NO. 22). About 10 μl of each PCR reaction are then resolved using native 6% polyacrylamide gels, run in 0.6× TBE buffer. After an appropriate time, the gels are dried and exposed to a PhosphorImager™ plate (Molecular Dynamics). The appropriate bands are then identified and quantified using the PhosphorImager quantification software.

Other useful primers of the invention for amplifying or detecting GC6 gene or mRNA include KJC54, defined by the sequence: 5'-GGACCTGATTCCCCAGTTGG (SEQ ID NO. 23); KJC55, defined by the sequence: 5'-AGTACTGGCCAGATGAGTTT (SEQ ID NO. 24); KJC56, defined by the sequence: 5'-TCACACGGCCTGTCTTTGAT (SEQ ID NO. 25); KJC58, defined by the sequence: 5'-CATGCCCAAAGTGGACACAG (SEQ ID NO. 26); and KJC59, defined by the sequence: 5'-GAATTCTTTTCTCTCTGTATTTAGGTATCCTG (SEQ ID NO. 27).

Example 4

Dot-Blot Method to Determine GC6 mRNA Levels in Various Tissues

One can also detect GC6 gene products using a dot blot protocol. A dot blot array (Master Blot) of human RNA samples can be obtained from ClonTech. A $^{32}$P-labeled probe was prepared using an EcoRI restriction enzyme digest product from the GC6 cDNA and and was used as a hybridization probe as described in the manufacturer's protocol.

The probe was produced as follows. Approximately 100 ng of an EcoRI restriction fragment from pGC6L was prepared. This fragment was labeled with 3$^2$P using a Ready-To-Go™ kit (Pharmacia) according to the manufacturer's instructions. The labeling reaction products were then purified using a Sephacryl S400 HR spin column (Pharmacia) as per the manufacturer's instructions.

The purified probe was hybridized to the Master Blot as instructed by the manufacturer. Briefly, the blot was first pre-hybridized at 65° C. in an ExpressHyb™ solution containing 1 mg/ml salmon sperm DNA, then hybridized in a similar solution that contains the prepared, denatured probe and Cot-1 human DNA. Following an overnight incubation at 65° C., the blot was washed under stringent solution conditions and then exposed for an appropriate time to a PhosphorImager™ screen (Molecular Dynamics).

Example 5

Multiplex Probing for GC6 mRNA Together with Other Senescence-Specific Gene Products In one embodiment, the GC6 mRNA is measured using an array of senescence-specific gene products. High density DNA array technology is useful method used to detect and quantify the levels of specific transcripts in a nucleic acid mixture. In general, these arrays consist of ordered patterns of DNA molecules, called targets, fixed to a solid-phase matrix, typically silicon. These targets may be manufactured by a variety of means. For example, Affymetrix, Inc., produces DNA arrays using a photolithographic technique in which short oligonucleotides are synhesized in situ, while Synteni Corp. deposits solutions containing the target DNAs using high density printing techniques.

To prepare a DNA chip using the latter technique, bacterial clones containing the ESTs (nucleic acids encoding expressed sequence "tags") are grown in an appropriate antibiotic-containing medium, and the plasmid DNA in the clones is amplified using PCR and vector-specific primers. A portion of the amplification products are checked on an agarose gel to verify the size and amount of the amplified target. The remainder of the sample is purified and arrayed onto glass slides.

Poly A+ mRNA samples are purified as described below and fluorescently-labeled. These probes are hybridized to the DNA arrays, which are then subsequently washed, and the bound fluorescence is quantified. Poly(A+) mRNA is isolated from total RNA using poly-dT resin from the Qiagen OligoTex™ isolation kit. There are kits from Qiagen to isolate polyA directly from cell culture, but it is preferred to isolate total RNA first.

To isolate total RNA, 150 mm cell culture plates containing the cells of interest are washed twice with dilute PBS (Ca and Mg free), About 1 ml of 4 M guanidine isothiocyanate (GITC)/25 mM Na acetate, pH6/0.8% mercaptoethanol is added to the 150 mm plate to facilitate cell lysis and extraction of RNA. The resulting mixture is scraped to one side and pippetted into 6 ml of a GITC/Na acetate/ mercaptoethanol solution for a total volume of 7 ml. This mixture is layered this onto an Ultraclear 14×89 mm polycarbonate tube (Beckman 34059) that has 4 ml of 5.7 M CsCl2 as a bedding.

These samples are centrifuged at 32K rpm for 20 hours at 16° C. in a SW41 swinging bucket rotor using a Beckman XL-80 ultracentrifuge. The supernatant is removed, and the pellet allowed dry for ~10 minutes. The pellet is resuspended in 360 µl of DEPC water (2×180 µl suspensions). About 40 µl of 3M Na acetate (pH 6 or 5.2) is added to the mixture together with 1 ml of 100% cold EtOH, and the resulting mixture is centifuged for 20–30 minutes at 14K rpm under cold room conditions. The ethanol is removed, and the pellet is allowed to dry and resuspended in an appropriate volume of DEPC water. Purity is checked by measuring OD and 260/280 ratios.

Poly-A mRNa is isolated from total mRNA using a Qiagen Oligotex kit. About 1–250 µg of total RNA is dissolved in DEPC water to 250 µl, and then 250 µl of 2× Binding Buffer and 15 µl of the the Oligotex polydT resin suspension are added, the contents mixed in a 1.5 ml Eppendorf tube and incubated at 65° C. for three minutes. The mixute is allowed to stand at room temperature for 15–20 minutes and then centrifuged at maximal speed on a benchtop centrifuge at room temperature for 2 minutes. The supernatant is discarded, and the pellet washed once with 400 µl of Wash Buffer QW2.

The contents are transferred to a spin column, which is centrifuged at full speed for about 2 minutes, and then transferred to another 1.5 ml microcentrifuge tube, and washed again with 400 µl of QW2 wash buffer and centrifuged again for 2 minutes at maximum speed. The flowthrough is discarded, and the polyA RNA is washed off by adding 20 µl of DEPC water warmed to 70° C. The above procedure is repeated once, and the eluted material contains polyA mRNA. From 100 µg of total RNA from cell culture, about 1–3 µg of polyA RNA are obtained. Purity and quantity are checked by measuring OD 260/280 ratios and 1% agarose/EtBr gel electrophoresis. This material is suitable for labeling and hybridization to a DNA chip.

An illustrative DNA chip for screening in accordance with the present invention is described below. First, the various nucleic acids, defined by Genbank accession and clone numbers are described; then, a protocol for preparing the nucleic acids to be placed on the chip is described. Thus, one panel of preferred nucleic acids is described in tabular form below.

| GenBankID | CloneID | Gene or Marker |
|---|---|---|
| w49497 | 325050 | interstitial collagenase precursor |
| n69322 | 285780 | collagenase 3 precursor |
| aa034203 | 471174 | stromelysin-3 precursor |
| aa046659 | 487394 | plasminogen activator inhibitor-1 (PAI-1) |
| H48533 | 201890 | TNFa |
| aa283090 | 713145 | hyaluronic acid receptor (CD44) |

-continued

| GenBankID | CloneID | Gene or Marker |
|---|---|---|
| t80285 | 24664 | hyaluronidase |
| aa293101 | 726240 | collagen 1a1 |
| aa398701 | 727729 | collagen 1a3 |
| t79116 | 113513 | elastin |
| w88847 | 417799 | fibronectin |
| aa127854 | 501773 | fibronectin receptor alpha subunit |
| aa236739 | 876065 | ATM |
| h68922 | 212078 | integrin alpha subunit (laminin receptor) |
| aa292578 | 723936 | TIMP-1 |
| aa043969 | 487021 | TIMP-3 |
| h15949 | 48452 | Acid sphingomyelinase |
| aa029514 | 366842 | N-CAM |
| aa281410 | 705220 | mortalin |
| aa284503 | 713672 | prohibitin |
| aa009762 | 429771 | aldehyde dehydrogenase (ALDH-1) |
| aa293501 | 726105 | 80K-L |
| aa001357 | 427894 | lipoprotein-associated coagulation inhibitor |
| aa046260 | 488870 | secretory granule proteoglycan core protein precursor |
| r21396 | 36200 | human tissue factor |
| aa058472 | 489366 | IGF binding protein 1 |
| aa040602 | 376184 | IGF binding protein 3 |
| aa029472 | 366793 | IGF binding protein 5 |
| n44809 | 272210 | rho8 |
| r48580 | 153589 | stanniocalcin |
| t75438 | 23176 | follistatin-related protein |
| aa215765 | 683517 | GC4 |
| w47081 | 325063 | GC6 |
| w37627 | 321886 | GC7 |
| aa005169 | 429074 | GC10 |
| r01968 | 124540 | Cu/Zn SOD |
| h65391 | 210401 | MnSOD |
| aa007652 | 429455 | glutathione synthetase |
| r46847 | 152524 | p21/SDI1/CIP1/WAF1 |
| w00390 | 291057 | p16 |
| r18972 | 33368 | p27 |
| t89175 | 110022 | cyclin D1 |
| h62385 | 236338 | p53 |
| n25402 | 264214 | Rb susceptibility gene |
| aa287985 | 701394 | Werner's Syndrome gene |
| r72795 | 157725 | retinoic acid inducible factor |
| aa292734 | 726275 | osteonectin |
| r96180 | 231021 | cyclooxygenase-1 (COX-1) |
| w93945 | 357451 | EPC-1/PEDF |
| r08428 | 127318 | ALDH-1 (mitochondrial) |
| H74252 | 229341 | VEGF |
| w80716 | 415588 | presenilin 1 |
| aa041277 | 376303 | insulin like growth factor(IGF) |
| H16473 | 49060 | TGF-b1 |
| aa037699 | 484975 | TGF-bbinding protein (endoglin) |
| w95660 | 357811 | TGF breceptor type 1 |
| r14113 | 27430 | acidic fibroblast growth factor (FGF) |
| R84654 | 180204 | basic fibroblast growth factor receptor |
| aa278581 | 703433 | FGF-receptor activating protein I |
| aa403247 | 758523 | platelet-derived growth factor (PDGF-alpha) |
| w72000 | 345645 | platelet-derived growth factor (PGDF-beta) |
| aa054505 | 489395 | PDGF-alpha receptor |
| aa075724 | 545136 | epidermal growth factor (EGF) |
| aa026175 | 469272 | EGF receptor |
| aa207063 | 682639 | TNF a |
| w72329 | 345232 | TNF beta |
| w89178 | 417861 | transferrin receptor |
| aa001614 | 427812 | Insulin receptor |
| aa009608 | 365515 | keratinocyte growth factor |
| w74536 | 346604 | RAGE receptor |
| R17089 | 129839 | protein kinase C zeta |
| N80314 | 290412 | b-Catenin |
| r39221 | 23173 | Mitosis activating protein (MAP) kinase |
| aa278157 | 712516 | MAPKK1 |
| aa425826 | 769579 | MAPKK2 (MEK1/erk activating kinase) |
| w90037 | 417357 | MAPK phosphatase-1 |
| h87371 | 252443 | MAPK phosphatase-2 |
| N67917 | 286709 | c-fos |
| W23847 | 309864 | junB |
| w87741 | 417226 | c-myc |
| aa058523 | 489327 | c-raf |
| H61706 | 206186 | c-src |
| w38444 | 328467 | c-ras |

-continued

| GenBankID | CloneID | Gene or Marker |
|---|---|---|
| h05603 | 43504 | c-erbA (thyroid hormone receptor) |
| aa293570 | 714213 | FAS |
| h74208 | 232714 | BCL-2 |
| t95052 | 120106 | ICE |
| n76118 | 299429 | ICAM-1 |
| aa281973 | 712849 | Poly (ADP-ribose) polymerase |
| r17189 | 32026 | DNA-PK |
| T72581 | 22040 | 92 kDa type IV collagenase precursor |
| T80285 | 24664 | hyaluronidase |
| T75563 | 112912 | Von Hippel-Lindau Disease tumor suppressor |
| T79116 | 113513 | elastin |
| T85543 | 114712 | proteinase 3 precursor |
| T96150 | 121022 | human monocyte activation antigen (PAI receptor) |
| R01893 | 124488 | soluble epoxide hydrolase |
| R05275 | 125077 | fibrinogen gamma-B |
| R42288 | 30689 | proteoglycan link protein precursor |
| R18972 | 33368 | p27 |
| R52103 | 40205 | cathepsin B |
| R67275 | 41676 | collagen alpha 1(XI) |
| R36670 | 136956 | tumor suppressor SNC6 |
| R68482 | 139242 | tumor suppressor, PDGF receptor beta-like |
| R64102 | 139584 | Rb-binding protein 2 |
| R67214 | 140827 | tumor suppressor DPC4 |
| R79223 | 146311 | 72 kDa type IV collagenase precursor (gelatinase A) |
| R80235 | 147075 | MDM-2 |
| R81706 | 147787 | plakoglobin |
| R46847 | 152524 | p21/SDI1/CIP1/WAF1 |
| R48414 | 153530 | procollagen-lysine, 2-oxoglutarate 5-dioxygenase precursor |
| R72075 | 155716 | heregulin |
| H21471 | 159990 | Cdk2 |
| H08667 | 45851 | collagen, type XVIII, alpha |
| H15949 | 48452 | acid sphingomyelinase |
| H15147 | 49898 | APC-1 |
| H49433 | 178772 | Human mRNA for senescence marker protein-30 |
| R83615 | 187615 | calcium-dependent protease, small |
| H45943 | 188230 | ATM |
| H48122 | 193736 | BRCA2 |
| R98783 | 200898 | kininogen, LMW precursor |
| H53852 | 202647 | collagen, type II, alpha 1 |
| H58247 | 204519 | cathepsin E |
| H58473 | 205905 | glutathione-S-transferase |
| R98080 | 206806 | tumor suppressor LUCA-1 |
| H61812 | 236374 | Cdk4 |
| N53585 | 245614 | cathepsin S |
| H81981 | 249453 | tumor suppressor HTS1 |
| N29616 | 257294 | M-phase inducer phosphatase 2 |
| N30878 | 258129 | trichohyalin |
| N30678 | 258294 | p57KIP2 |
| N25120 | 262198 | beta-catenin |
| N20106 | 263118 | cartilage homeoprotein 1, CART-1 |
| N62929 | 278705 | Rb susceptibility gene |
| N58841 | 288791 | proliferation-associated protein PAG (peroxidase antioxidant) |
| N67639 | 290753 | citrate synthase |
| N71998 | 290871 | integrin alpha-3 subunit (lam,fibro,collagen receptor) |
| N72115 | 291057 | p18 (CDK6 inhibitor) |
| N67818 | 291622 | putative tumor suppressor EXT1 |
| N68071 | 292115 | collagen 1 alpha 2 |
| N80868 | 300702 | thrombospondin 4 |
| W19086 | 302057 | Cockayne's Syndrome gene |
| N93844 | 369199 | collagen XV alpha 1 |
| N93959 | 309345 | membrane-type matrix metalloprotease-2 |
| N94385 | 309515 | thrombospondin 4 (cartilage oligomeric matrix protein) |
| N94405 | 309560 | collagen III( 1 |
| W30775 | 309591 | p300 (E1A binding protein) |
| W42634 | 323181 | Human fibroblast activation protein mRNA |
| W44410 | 323621 | growth defect suppressor HCP1 homolog |
| W47091 | 324700 | stromelysin-1 precursor |
| W47129 | 324700 | stromelysin-2 precursor |
| W49497 | 325050 | interstitial collagenase precursor |
| W49820 | 325720 | probable hyaluronan synthase Has2 |
| W68308 | 342670 | corticosterone methyl oxidase |
| W68308 | 342670 | brighter band in amp. check comparison of dots. |
| W67555 | 343187 | HIC-1 tumor suppressor |
| W68086 | 343362 | paxillin |
| W73785 | 344109 | PCNA |
| W73874 | 345538 | cathepsin L |

-continued

| GenBankID | CloneID | Gene or Marker |
|---|---|---|
| W92603 | 357681 | cathepsin G |
| W95471 | 357807 | cyclin E |
| W94563 | 358017 | fibrinogen gamma-A |
| W94858 | 358441 | growth arrest specific clone 1 (gas1) |
| AA017532 | 361203 | plasma glutathione peroxidase |
| AA018325 | 361518 | p19 |
| AA019833 | 363365 | Drosophila tumor-suppressor homolog DLG2 |
| AA025310 | 364715 | thrombospondin 3 |
| AA009519 | 365465 | P-TEN |
| AA025750 | 366323 | HE4 mRNA for extracellular proteinase inhibitor homologue |
| AA026625 | 366539 | fibrinogen alpha |
| AA026137 | 366639 | proteoglycan 2 |
| AA029408 | 366789 | fibromodulin |
| AA029472 | 366793 | IGF binding protein 5 |
| AA055178 | 377215 | cathepsin C |
| AA055445 | 377516 | fibrinogen beta |
| W80458 | 415495 | glutathione peroxidase |
| W86006 | 416134 | thrombospondin 2 |
| W89129 | 417320 | tissue plasminogen activator precursor |
| W89002 | 417469 | catalase |
| AA001329 | 427857 | cyclin A |
| AA004918 | 428443 | laminin B-1 |
| AA007652 | 429455 | glutathione synthetase |
| AA009433 | 429859 | ezrin |
| AA010398 | 430308 | BRCA1-associated RING protein |
| AA026112 | 469281 | HUGL tumor suppressor |
| AA029360 | 470346 | laminin B-2 |
| AA031483 | 470679 | collagen IV alpha 1 |
| AA034203 | 471174 | stromelysin-3 precursor |
| AA035118 | 471736 | beta-galactosidase precursor |
| AA044261 | 486375 | fibronectin receptor beta subunit |
| AA043969 | 487021 | TIMP-3 |
| AA045473 | 487887 | tenascin |
| AA045285 | 487934 | vinculin |
| AA047455 | 488455 | cathepsin D |
| AA056585 | 489181 | thrombospondin 1 |
| AA056736 | 489224 | Human retinoblastoma-binding protein (RbAp46) mRNA |
| AA058337 | 489348 | cathepsin H |
| AA284503 | 713672 | prohibitin |
| AA284825 | 713858 | aggrecan |
| AA291692 | 724729 | AT (group D) |
| aa293101 | 726240 | collagen 1(1 |
| AA393564 | 727855 | glutathione reductase |
| AA393647 | 728263 | alpha-catenin |
| AA421151 | 728610 | integrin alpha-6 subunit |
| AA405362 | 742884 | Cdc2 |
| AA400097 | 743271 | TIMP-2 |
| AA425535 | 773289 | cytochrome C oxidase polypeptide IV |
| AA454160 | 795309 | extracellular superoxide dismutase precursor |
| AA453479 | 795352 | focal adhesion kinase-1(FAK-1) |
| AA461383 | 796853 | cartilage link protein |
| AA464438 | 809919 | focal adhesion kinase-2(FAK-2) |
| T65090 | 21703 | NF2 |
| T89023 | 22560 | 1-phosphatidylinositol -4,5-bisphosphate phosphodiesterase beta |
| T74988 | 23022 | calcium-binding protein BDR-1 (hippocalcin) |
| R38701 | 23354 | neurite growth-promoting factor 1 |
| R38385 | 23806 | N-cadherin |
| T77200 | 23820 | aryl hydrocarbon receptor nuclear translocator |
| T78739 | 24067 | tyrosine-protein kinase receptor CEK5 |
| T90203 | 110589 | Stat5B |
| T90467 | 110999 | CAMP response element binding protein CRE-BP1 |
| T91043 | 112500 | tyrosine-protein kinase receptor UFO |
| T79177 | 113583 | tel, ets-related |
| T86845 | 114648 | NF-KB p105 |
| T85572 | 114760 | 6-O-methylguanine-DNA methyltransferase |
| T87961 | 115767 | dual specificity mitogen-activated protein kinase kinase 1 |
| T89493 | 116268 | interleukin 6 gp 130 (IL-6 signal transducer) |
| T89622 | 116781 | FGF receptor 3 |
| T95052 | 120106 | ICE |
| T95187 | 120157 | integrin alpha 9 |
| T95289 | 120468 | ERCC1 |
| R00391 | 123360 | topoisomerase 1 |
| R00830 | 123586 | syndecan-1 precursor |
| R01393 | 123738 | cell death supression-interacting protein NIP1 |
| R01192 | 123755 | ETS-related erg |
| R01509 | 123914 | melanocyte-specific protein PMEL-17 |

-continued

| GenBankID | CloneID | Gene or Marker |
|---|---|---|
| R01921 | 124542 | keratin, type I cytoskeletal 13 |
| R05275 | 125077 | fibrinogen gamma-B |
| R05278 | 125092 | beta-1,4 N-acetylgalactosaminyltransferase |
| R07270 | 126812 | FGF receptor 4 |
| R08017 | 127089 | c-jun |
| R09550 | 128100 | syndecan-4 precursor |
| R10006 | 128773 | ERCC3 (XP-B) |
| R11690 | 25392 | RAS-related protein RAL-B |
| R38513 | 26871 | FGF receptor 2 (keratinocyte growth factor receptor) |
| R37762 | 26820 | neuronal membrane glycoprotein M6b |
| R39148 | 26811 | Human XRCC4 mRNA |
| R14080 | 27516 | cyclophilin ligand, calcium modulating |
| R14113 | 27430 | acidic fibroblast growth factor (FGF) |
| R40903 | 28573 | multidrug resistance protein 1 |
| R13451 | 28375 | opioid-binding cell adhesion molecule |
| R14153 | 28513 | topoisomerase 2 |
| R14230 | 28422 | neurofilament, subunit L |
| R41176 | 29204 | glycosyl phosphatidylinositol |
| R15029 | 29363 | neuromedin-B receptor |
| R14703 | 30066 | ankrin (integrin-linked kinase) |
| R14937 | 30125 | Vimentin |
| R18500 | 30373 | cell death supression-interacting protein NIP3 |
| R42752 | 31267 | JNK2 |
| R17189 | 32026 | DNA-PK |
| R17458 | 32432 | cdk8 |
| R44542 | 34005 | pSK1 interferon gamma receptor accessory factor-1 (AF-1) |
| R44553 | 33800 | HSP70B |
| R21092 | 36232 | carbonic anhydrase I |
| R34402 | 36987 | ETS-realted ergB |
| R49611 | 37522 | osteocalcin |
| R50771 | 38829 | Human mRNA for protein-tyrosine phosphatase |
| R51032 | 38853 | EGF receptor kinase substrate |
| R54467 | 39602 | steroid receptor TR2 |
| R56618 | 41289 | transcriptional regulator, via glucocorticoid receptor |
| R59031 | 41138 | FHF2 |
| R59202 | 41480 | MADS/MEF2 |
| R66467 | 41882 | Poly (ADP-ribose) polymerase |
| R59620 | 42122 | lysosomal membrane 85K sialoglycoprotein precursor |
| R60862 | 42291 | diacylglycerol kinase, gamma |
| R60583 | 37855 | onconeural ventral antigen 1 |
| R59442 | 37827 | tropomyosin-related protein, neuronal |
| R59498 | 37836 | retinoic acid receptor (RAR) X b |
| R22815 | 130324 | E-cadherin |
| R23999 | 131137 | perlecan |
| R25994 | 132574 | arachidonate 5-lipoxygenase |
| R31984 | 134322 | MU-type opioid receptor |
| R32041 | 134451 | wee1 |
| R68531 | 137794 | activin receptor isoform IIB2 |
| R63093 | 138002 | interferon b1 |
| R53921 | 138209 | laminin-related protein A3 |
| R63470 | 138644 | Cadherin 5 |
| R62703 | 138797 | VEGF-receptor |
| R62940 | 139073 | interleukin-2 receptor beta chain |
| R64353 | 139288 | 5,10-methenyltetrahydrofolate synthetase |
| R62384 | 139840 | noradrenaline transporter |
| R67970 | 140689 | vitamin K-dependent gamma-carboxylase |
| R63819 | 141321 | grancalcin |
| R71212 | 143014 | bone morphogenetic protein-1 |
| R77028 | 144233 | tumor necrosis factor receptor 2 related protein |
| R79900 | 146042 | inhibin beta A chain |
| R79028 | 146213 | cell death supression-interacting protein NIP2 |
| R80217 | 147050 | cyclooxygenase-2 (COX-2) |
| R81583 | 147727 | kappa-type opioid receptor |
| H12306 | 148420 | p21-activated protein kinase (Pak1) |
| H12367 | 148425 | beta-globin |
| R82176 | 148968 | MAD-related gene SMAD7 |
| H04544 | 150163 | neuropeptide Y receptor Y1 |
| H01810 | 150495 | keratin, type I cytoskeletal 19 |
| H01971 | 150638 | fibulin 1, isoform B |
| H02312 | 151213 | c-K-ras |
| H03104 | 152206 | RagA |
| R50456 | 152778 | 11-cis retinol dehydrogenase |
| R50193 | 153195 | human rad51 |
| R48368 | 153826 | transforming protein RHOB |
| R53012 | 154269 | keratin, type I cytoskeletal 14 |
| R53185 | 154359 | H-twist |
| R55303 | 154790 | low-affinity nerve growth factor receptor |

-continued

| GenBankID | CloneID | Gene or Marker |
|---|---|---|
| R72820 | 156180 | lethal G protein-mutation suppressor, Gps1 |
| R72827 | 156183 | ICAM-3 |
| R72598 | 156272 | p38 Beta (MAP kinase p38Beta) |
| R73050 | 156431 | CNTF receptor |
| R73919 | 156753 | E2F |
| R72898 | 157881 | ras-related GTPase, membrane associated, ARP1 |
| H26723 | 158231 | N-acetylgalactosamine-6-sulfatase |
| H24504 | 159795 | plasma retinol-binding protein |
| H24956 | 160664 | proto-oncogene tyrosine-protein kinase receptor RET |
| H25136 | 161038 | inositol 1,4,5-triphosphate receptor (type 3) |
| H25797 | 161569 | presenilin 2 |
| H27557 | 162772 | early grownth response protein 1 |
| H05603 | 43504 | c-erbA (thyroid hormone receptor) |
| H06322 | 44296 | HPRT |
| H11003 | 47359 | endothelin-1 |
| H11603 | 47510 | vesicle coat protein, neuron-specific |
| H14704 | 48653 | transcription factor ETV1/ER81, ets-related |
| H16591 | 49164 | vascular cell adhesion protein 1 precursor |
| H15590 | 49284 | FHF3 |
| H19129 | 50930 | FGF homologous factor 1 (FHF 1) |
| H24237 | 51940 | beta-2-microglobulin precursor |
| H29687 | 52854 | b-Catenin |
| H14285 | 163644 | early response protein NAK1 |
| H22542 | 173707 | neuron-specific growth-associated protein / stathmin homolog |
| H23818 | 173839 | PMS3 homolog mismatch repair protein |
| H29847 | 174868 | cysteine dioxygenase |
| H40230 | 175266 | heat shock protein, 75 kDa, mitochondrial |
| H45381 | 176537 | basic fibroblast growth factor (FGF) |
| H40775 | 177310 | ribosomal protein S9 |
| H46925 | 178048 | estrogen receptor hSNF2b |
| H46845 | 178308 | neuronal pentraxin 1 (NPTX1) |
| H51148 | 179603 | RAB-3A |
| R85117 | 180726 | 2',3'-cyclic nucleotide 3'-phosphodiesterase |
| H41908 | 182295 | cytochrome P450 IIB6 |
| H43131 | 182987 | keratin, type II cytoskeletal8 |
| H43783 | 184238 | MMP-like, disintegrin-like, cysteine-rich protein (MDC) |
| H39991 | 186132 | E-selectin |
| R83789 | 186615 | GDP-dissociation inhibitor rho |
| R83224 | 187147 | ras inhibitor INX |
| H37967 | 190593 | paraneoplasyic encephalomyelitis antigen HUD (ELAV-like) |
| H38240 | 191664 | thrombospondin 2 |
| H39144 | 192435 | TATA-binding protein (TBP) |
| R89150 | 195614 | phenylalanine hydroxylase |
| R89340 | 195702 | ionizing radiation resistance-conferring protein |
| R89340 | 195702 | ionizing radiation resistance-conferring protein |
| R95185 | 198775 | erythropoietin receptor |
| H82878 | 198873 | b-actin |
| H48460 | 200579 | laminin, M polypeptide (merosin heavy chain) |
| R99791 | 200978 | iron-responsive element-binding protein |
| H48602 | 202057 | Toll protein |
| H48596 | 202058 | lysosome-associated membrane glycoprotein 2 precursor |
| H53585 | 202765 | keratin, type II cytoskeletal7 |
| H54347 | 203089 | hepatoma-derived growth factor |
| H60824 | 205239 | protein kinase C theta |
| H59352 | 206509 | E2F2 |
| R98050 | 206795 | asialoglycoprotein receptor 2 |
| H60775 | 209153 | fructose-bisphosphonate aldolase B |
| H62035 | 209227 | FGF receptor k-sam |
| R39221 | 209283 | Mitosis activating protein (MAP) kinase |
| H69011 | 211285 | sno oncogene |
| H66704 | 211864 | TNF receptor II associated protein (TRAF2) |
| H69474 | 212414 | retinoic acid receptor |
| H85143 | 220177 | fructose-bisphosphonate aldolase C |
| R50354 | 220419 | LIF |
| H91647 | 221076 | Human mRNA for rod photoreceptor protein |
| H91651 | 221092 | nuclear respiratory factor 2 gamma subunit |
| H92621 | 221653 | neural cell adhesion and axonal path-finding molecule homolog |
| H86642 | 223350 | ceruloplasmin |
| H79373 | 229335 | insulin-like growth factor II |
| H92681 | 231542 | neurofilament triplet M protein |
| H73424 | 232622 | 23K highiy basic protein |
| H74208 | 232714 | protein BCL-2-alpha |
| H72723 | 232772 | metallothionein-IIB |
| H78484 | 233583 | interleukin-1 receptor, type II |
| H77454 | 233684 | RAB-8 |

-continued

| GenBankID | CloneID | Gene or Marker |
|---|---|---|
| H66259 | 234198 | Cdk6 |
| H79456 | 235135 | integrin a4 |
| H52673 | 235938 | BAK |
| H61204 | 236306 | keratin, type I cytoskeletal 17 |
| H80710 | 241484 | B-myb |
| H92970 | 241993 | HMG-CoA reductase |
| H95081 | 243320 | a-1 antitrypsin |
| N39046 | 243508 | rap-1B (ras related protein) |
| N49908 | 243678 | vitamin D3 binding protein |
| N39202 | 243879 | Wilm's tumor gene |
| N54791 | 244301 | phospholipase A2 (Ca2+sensitive) |
| N54435 | 244827 | TGF-beta induced gene product (BIGH3) |
| N53549 | 245490 | cytochrome P450 monooxygenase CYP2J2 |
| N78068 | 248244 | haptoglobin 1 |
| N58777 | 248613 | c-myb |
| H83566 | 249361 | osteoclast stimulating factor |
| H84388 | 249568 | guanine nucleotide-binding protein rab5c-like protein |
| H96326 | 250269 | thiol-specific antioxidant protein |
| H96451 | 251200 | c-kit |
| H96505 | 251421 | BMP-4 receptor, type II |
| H96519 | 251469 | BMP-2 receptor |
| N26291 | 256842 | ADP/ATP translocase |
| N30606 | 257766 | cyclin H |
| N30878 | 258129 | trichohyalin |
| N56778 | 258504 | inhibin a |
| N32142 | 258584 | cAMP-responsive element modulator |
| N56815 | 258589 | C-REL proto-oncogene |
| N29501 | 259291 | integrin beta-5 |
| N57463 | 259363 | RAS-related protein RAB-9 |
| N32784 | 259642 | Human GTP cyclohydrolase I mRNA |
| N42072 | 259927 | 5-lipoxygenase activating protein |
| H99256 | 260332 | thrombospondin 4 |
| H97938 | 260737 | glucocorticoid receptor, alpha |
| H99410 | 262686 | Mad homolog JV5-1 |
| H99414 | 262691 | glucocorticoid receptor, beta |
| N28416 | 263688 | Bfl-1, Bcl-2-related |
| N20079 | 263732 | ceramide glucosyltransferase |
| N28551 | 263940 | helicase II (RAD54L) |
| N20556 | 264074 | IQGAP1 (ras GTPase activating-like protein) |
| N20574 | 264099 | tyrosinase |
| N21349 | 265151 | protein kinase, cAMP-dependent, catalytic, alpha subunit |
| N20844 | 265267 | heat shock 70 KD protein 1 |
| N31113 | 265344 | acid sphingomyelinase-like phosphodiesterase 3a, ASML3a |
| N24967 | 267422 | epidemial growth factor receptor HER3 |
| N29996 | 268231 | calcineurin |
| N26851 | 269647 | erm, ets-related |
| N24811 | 269753 | p190-B, rho GAP Family |
| N27159 | 269815 | inhibin bA |
| N42732 | 270927 | guanine nucleotide-binding protein Rab5B |
| N46403 | 273750 | guanine nucleotide-binding protein Rab26 |
| N38781 | 273941 | disintegrin-metalloprotease |
| H49613 | 274134 | carbonic anhydrase II |
| R93351 | 275610 | thromboxane-A synthase |
| N39219 | 276946 | Ca2+/calmodulin-dependent protein kinase isoform gamma C |
| N66100 | 278409 | JNK activating kinase 1 |
| W01322 | 278490 | RAS-like protein TC21 |
| N62906 | 278638 | bone inducing protein |
| N48784 | 279435 | ERK3 |
| N48796 | 279470 | Mch3 |
| N57553 | 279970 | adenosine A2A receptor |
| N48082 | 281778 | TGF-b2 |
| N51103 | 281981 | protein kinase C mu |
| N51472 | 282060 | ERCC2(XP-D) |
| N52079 | 282563 | CDK-activating kinase |
| N53393 | 284031 | transforming protein P21/N-RAS |
| N52338 | 284459 | protein kinase C beta II |
| N62083 | 287500 | scatter factor (HGF) |
| N59150 | 287687 | interferon-alpha/beta receptor alpha chain |
| N76623 | 289268 | calcium-binding protein S100E, EF-hand |
| N59268 | 289600 | lactotransferrin |
| N77150 | 289941 | DNA alkylation damage repair protein ABH |
| N90839 | 290366 | neurofilament, 66 kDa |
| N62377 | 290563 | prostaglandin G/H synthase 1 |
| W02974 | 291350 | P-cadherin |
| W03390 | 291571 | histamine N-methyltransferase |
| W03485 | 291982 | SMAD5 |

-continued

| GenBankID | CloneID | Gene or Marker |
|---|---|---|
| N68268 | 292326 | DNA primase 58 kDa subunit |
| N91234 | 292477 | MAX delta |
| N63852 | 293111 | uracil-DNA glycosylase 1 precursor |
| N70358 | 295389 | growth hormone receptor |
| W05062 | 298676 | HSP27 |
| N75376 | 298898 | cardiac actin, alpha |
| W15554 | 301138 | phospholipase A2, membrane associated |
| N89581 | 301449 | vasopressin V2 receptor |
| N89782 | 302071 | hevin, antiadhesive extracellular matrix protein-related |
| N78944 | 302383 | alpha-N-acetylgalactosaminidase |
| W19257, | 302808, | ??? |
| W38564 | 302490 | G2/mitotic-specific cyclin B1 |
| H41433 | 302484 | protein kinase C zeta |
| W38932 | 304843 | heme oxygenase 2 |
| W38689 | 305014 | ornithine decarboxylase |
| W39150 | 305149 | IAP (inhibitor of apoptosis) |
| N91919 | 306848 | mineralocorticoid receptor |
| W24300 | 306951 | retinol-binding protein I, cellular |
| N95176 | 307293 | rap-1A (ras related protein) |
| N92931 | 307710 | natriuretic factor ANP |
| N94440 | 309615 | G1/S-specific cyclin D3 |
| N94500 | 309926 | TRAF-interacting protein (I-TRAF) |
| N99151 | 310021 | gamma-interferon-inducible protein IP-30 |
| W24218 | 310084 | peptidyl-glycine alpha-amidating monooxygenase precursor |
| N98563 | 310105 | retinoic acid/interferon-inducible 58K protein RI58 |
| W24356 | 310148 | activin receptor-like kinase (ALK-1) |
| N98591 | 310406 | interleukin 6 |
| W19208 | 310786 | urokinase plasminogen activator surface receptor, GPI-anchored |
| W04648 | 320377 | interleukin-1 receptor, type I |
| W32272 | 321386 | IQGAP2 (ras GTPase activating-like protein) |
| W33156 | 321853 | Huntington |
| W37817 | 321997 | Human G/T mismatch-specific thymine DNA glycosylase |
| W39728 | 322720 | secretory phospholipase A2 receptor precursor, soluble form |
| W42469 | 323158 | keratin, type I cytoskeletal18 |
| W45586 | 323438 | extracellular signal-regulated kinase 1 (ERK1) |
| W45388 | 323477 | melanoma differentiation associated mRNA, mda-6 |
| W44316 | 323500 | Mch2 (apopain) |
| W44326 | 323626 | interferon a |
| W47335 | 324244 | probable translocase hTOM34, outer mitochondrial membrane |
| W47667 | 324358 | ESTs, Highly similar to stress-activated protein kinase JNK3 |
| W46900 | 324437 | melanoma growth stimulatory activity protein |
| W46792 | 324578 | DP2 (E2F dimerization partner) |
| W47101 | 324655 | interleukin 1 b |
| AA284113 | 324751 | Notch 3 |
| W49512 | 324760 | B1 bradykinin receptor |
| W47169 | 324794 | laminin S |
| W47311 | 324799 | ESTs similar to AHRNT |
| W48569 | 324990 | BRAIN-derived neurotrophic factor |
| W49706 | 325077 | uPA surface receptor, GPI-anchored FORM |
| W48562 | 325145 | TNF-inducible binding protein (PENTAXIN-related protein PTX3) |
| W48807 | 325202 | RAS-like protein TC10 |
| W52204 | 325355 | latent transforming growth factor-beta binding protein |
| W56439 | 326462 | calcium-sensing receptor |
| W56465 | 326463 | guanine nucleotide-binding protein G(S), alpha subunit |
| W01956 | 327284 | vasoactive intestinal polypeptide receptor 1 |
| W51953 | 340525 | cytochrome P450 XXIB |
| W56754 | 340644 | integrin beta-8 |
| W57705 | 340877 | guanine nucleotide-binding protein, G(i) alpha subunit |
| W57891 | 340918 | cystatin A |
| W58583 | 341108 | placental alkaline phosphatase |
| W58386 | 341609 | ICE-re1II |
| W58437 | 341694 | lysosome-associated membrane glycoprotein 1 precursor |
| W60764 | 341763 | ICE-re1III/TY |
| W68454 | 342608 | hnRNP B1 |
| W68281 | 342647 | Human MAPKAP kinase (3pK)mRNA, complete cds |
| W68291 | 342721 | integrin beta-2 |
| W67677 | 342833 | hnRNPE-2 |
| W67380 | 343091 | nuclear respiratory factor 2 alpha subunit |
| W67650 | 343304 | keratin, type II cytoskeletal1 |
| W69163 | 343681 | N-MYC proto-oncogene protein |
| W69649 | 343871 | MAPK/ERK kinase 5 |
| W70161 | 344234 | osteonidogen |

-continued

| GenBankID | CloneID | Gene or Marker |
|---|---|---|
| W73154 | 344345 | metallothionein-IE |
| W73473 | 344430 | bone morphogenetic protein-7 (OPI) |
| W73199 | 344613 | amyloid precursor protein-binding protein 1 |
| W74681 | 344775 | transducin 1 |
| W70203 | 344816 | telomerase repeat binding factor (TRF) |
| W77811 | 345839 | RAC-alpha serine/threonine kinase |
| W74233 | 346396 | r-ras |
| W74434 | 346587 | bone-derived growth factor 1 (BPGF-1) |
| W81376 | 347548 | ER lumen protein retaining receptor 1 |
| W84535 | 356636 | ADP-ribosylation factor 4 |
| W84436 | 356649 | ubiquitin-conjugating enzyme |
| W84340 | 356653 | IGF Binding Protein 6 |
| W92683 | 356964 | c-Abl(p150) |
| W93558 | 357252 | type 1A angiotensin II receptor |
| W93783 | 357309 | DNA-repair protein complementing XP-C cells |
| W93713 | 357374 | retinoic acid receptor (RAR) b 2 |
| W94002 | 357513 | fibulin-2 |
| W95362 | 357760 | ubiquitin |
| W94563 | 358017 | fibrinogen gamma-A |
| W95623 | 358198 | alpha-tubulin |
| W95867 | 358350 | ETS-related EWS (RNA binding) |
| W96099 | 358433 | retinoic acid receptor (RAR) X g |
| W92221 | 359017 | ERBB-3 receptor protein-tyrosine kinase precursor (EGF recepetor) |
| AA010301 | 359254 | Trypsinogen IV |
| AA011135 | 359793 | ESTs, Highly similar to insulin-like growth factor II |
| AA010830 | 359813 | titin |
| AA035545 | 359914 | melanoma growth regulatory protein MIA |
| AA063522 | 359984 | collagen V1 alpha 1 |
| AA013202 | 360133 | GAPDH |
| AA011014 | 360854 | interphotoreceptor retinoid-binding protein |
| AA012846 | 360862 | phospholipase D |
| AA001025 | 362009 | GADD153 |
| AA001186 | 362256 | fructose-bisphosphonate aldolase A |
| AA021512 | 363981 | osteopontin |
| AA021568 | 364277 | S-arrestin |
| AA022535 | 364339 | fibulin D |
| AA025344 | 364752 | Rho C |
| AA024625 | 365131 | interferon gamma receptor alpha chain |
| AA025141 | 365147 | ERBB-2 receptor protein-tyrosine kinase precursor |
| AA025225 | 365391 | Human PMS4 mRNA (yeast mismatch repair gene PMS1 homologue) |
| AA025251 | 365437 | inositol polyphosphate 5-phosphatase signal (SIP-110) |
| AA009608 | 365515 | FGF7 |
| AA009970 | 365566 | vitamin D3 receptor |
| AA009638 | 365597 | folate receptor beta precursor |
| AA009991 | 365609 | carbonic anhydrase III |
| AA025937 | 365641 | DNA primase 49 kDa subunit |
| AA025599 | 366254 | Human cysteine-rich fibroblast growth factor receptor (CFR-1) |
| AA026057 | 366276 | Ku |
| AA025672 | 366305 | TNF receptor II |
| AA025940 | 366341 | AH receptor precursor |
| AA026428 | 366412 | G1/S-specific CYCLIN D2 |
| AA026359 | 366420 | MAP kinase kinase 6 (MKK6) |
| AA026528 | 366425 | rab-11A |
| AA026625 | 366539 | fibrinogen alpha chain |
| AA026688 | 366583 | nebulin |
| AA029381 | 366716 | osteonectin |
| AA029408 | 366789 | fibromodulin |
| AA029443 | 366819 | laminin Ah (A4) |
| AA026677 | 366961 | ATP synthase beta chain |
| AA037787 | 375835 | ATP synthase COUPLING factor 6 |
| AA040602 | 376184 | IGF Binding Protein 3 |
| AA040781 | 376234 | Human XP group E UV-damaged DNA binding factor |
| AA040792 | 376260 | bradykinin receptor |
| AA046925 | 376820 | keratin, type II cytoskeletal5 |
| AA055349 | 377252 | adenosine A2B receptor |
| AA055480 | 377559 | DNA damage/retinoic acid-induce protein |
| AA056036 | 377671 | integrin alpha 7B |
| AA056184 | 377680 | Nucleolin |
| AA047869 | 380329 | arrestin-C |
| AA047765 | 380403 | Rho A |
| AA053838 | 380652 | ALK-2 |
| AA052906 | 381380 | inositol polyphosphate 1-phosphatase |
| AA058999 | 381600 | Deoxyribonuclease I homolog (DHP1) |
| W93118 | 415060 | erythropoietin precursor |

-continued

| GenBankID | CloneID | Gene or Marker |
|---|---|---|
| W80596 | 415481 | apyrimidinic/apurinic endonuclease (HAP) (APEX) |
| W85701 | 415703 | cdc2O |
| W86199 | 415899 | insulin degrading enzyme |
| W85871 | 416076 | hnRNP D |
| W87857 | 417218 | retinoic acid receptor (RAR) X a |
| W87790 | 417285 | fibroblast growth factor receptor BFR-2receptor |
| W88589 | 417475 | vacuolar ATP synthase subunit E |
| W90705 | 418004 | Bmi1 |
| W90426 | 418064 | steroid receptor coactivator (SRC-1) |
| W90102 | 418105 | rab-2 (ras related protein) |
| W90085 | 418138 | nuclear hormone receptor (shp) |
| AA001257 | 427786 | FLICE-like inhibitory protein |
| AA001772 | 427985 | endothelin converting enzyme 1 |
| AA004216 | 428356 | human rad50 |
| AA005393 | 428542 | NADH-ubiquinone dehydrogenase 24 KD subunit (mitochondrial) |
| AA011614 | 429598 | angiogenin precursor |
| AA009795 | 429851 | Homo sapiens 5,10-methenyltetrahydrofolate synthetase |
| AA033966 | 429883 | cytochrome P450 IIC8 |
| AA034057 | 429925 | a-1 acid glycoprotein |
| AA034051 | 429926 | APC |
| AA033993 | 429934 | DNA-binding protein inhibitor ID-2 |
| T91369 | 116501 | flk-1/KDR (VEGF receptor 2) |
| AA034015 | 430006 | dermatopontin |
| AA026197 | 469275 | prostaglandin-I synthase (prostacyclin synthase) |
| AA027039 | 469378 | TNF initial response protein B94 |
| AA027942 | 469737 | ESTs, Highly similar to cartilage matrix protein precursor |
| AA029824 | 469894 | bone morphogenetic protein-2 |
| AA028894 | 469936 | silencing mediator of retinoid and thyroid hormone action |
| AA029292 | 470101 | oxytocin receptor |
| AA029848 | 470196 | ERCC5 (XP-G) |
| AA031513 | 470393 | matrilysin (MMP-7) |
| AA031642 | 470480 | autocrine motility factor receptor |
| AA031933 | 470602 | steroid hormone receptor ERR1 |
| AA031671 | 479730 | ESTs, Highly similar to focal adhesion kinase |
| AA033842 | 471058 | Alzheimer's disease amyloid A4 protein |
| AA033924 | 471252 | retinoic acid receptor (RAR) g1 |
| AA034511 | 471365 | heat shock protein HSP 90-beta |
| AA034522 | 471394 | adenosylhomocysteinease |
| AA035241 | 471494 | integrin beta-4 |
| AA035527 | 471649 | dual specificity mitogen-activated protein kinase kinase 3 |
| AA035564 | 471679 | inositol 1,3,4 triphosphate 5/6 kinase |
| AA035099 | 471739 | OX40L receptor |
| AA035488 | 471756 | laminin gamma-1 |
| AA0355500 | 471778 | bone proteoglycan II |
| AA036770 | 471918 | ICAM-2 |
| AA036881 | 472008 | C-C chemokine receptor type 1 |
| AA037014 | 484641 | prostaglandin transporter |
| AA037376 | 484898 | EBV-induced G protein-coupled receptor 2 |
| AA040911 | 485039 | APO-A1 |
| AA039507 | 485227 | peroxisomal targeting signal 1 (SKL type) receptor |
| AA041538 | 485701 | serum response factor |
| AA040199 | 486001 | VEGF related factor (VRF) |
| AA043141 | 486055 | cytochrome P450 CYP1B1 (dioxin-inducible) |
| AA040942 | 486099 | N-acetylgalactosamine-6-sulfatase |
| AA040732 | 486161 | proto-oncogene tyrosine-protein kinase LCK |
| AA040617 | 486208 | TGF-b3 |
| AA040727 | 486215 | urokinase plasmiogen activator precursor |
| AA044018 | 486268 | amyloid-like protein 2 |
| AA043363 | 486547 | importin-alpha6 |
| AA044619 | 486757 | cathepsin K |
| AA043226 | 486785 | plasminogen |
| AA045303 | 487092 | interferon-inducible protein 1-8D |
| AA043718 | 487341 | endothelin receptor |
| AA046659 | 487394 | plasminogen activator inhibitor-1 (PAI-1) |
| AA046720 | 487416 | IGF Binding Protein 4 |
| AA044993 | 487513 | connective tissue growth factor precursor |
| AA045364 | 487811 | peptidyl-glycine alpha-amidating monooxygenase (PAM) |
| AA045473 | 487887 | tenascin |
| AA044736 | 487913 | TAU |
| AA044734 | 487916 | ADP-ribosylation factor 3 |
| AA054721 | 487979 | zyxin |
| AA058722 | 488163 | cellular growth-regulating protein |
| AA058543 | 488223 | Human Down syndrome critical region protein (DSC1) |
| AA046654 | 488383 | PDGF-beta receptor |
| AA047296 | 488596 | low-density LIPOprotein receptor |
| AA045826 | 488653 | PKC substrate 80 kDa, heavy chain |

-continued

| GenBankID | CloneID | Gene or Marker |
|---|---|---|
| AA047489 | 488678 | ferritin light chain |
| AA045836 | 488697 | ESTs, Highly similar to VEGF |
| AA045054 | 488801 | nerve growth factor (HBNF-1)(pleiotrophin) |
| AA046245 | 488842 | osteoblast specific factor 2 (OSF-2p1) |
| AA045058 | 488873 | syndecan-2 precursor |
| AA046249 | 488891 | ubiquitin-conjugating enzyme E2-17KD (RAD6-B) |
| AA047379 | 488932 | importin-beta |
| AA046892 | 488974 | defender against cell death 1 |
| AA047092 | 488999 | protein kinase C inhibitor |
| AA047161 | 489042 | CD30 |
| AA057189 | 489055 | RhoG |
| AA058523 | 489327 | Human mRNA for raf oncogene |
| AA058472 | 489366 | IGF binding protein 1 |
| AA101829 | 489545 | rad GTPase |
| AA152305 | 491243 | interferon gamma-inducible early response protein |
| AA150399 | 491485 | glucocorticoid receptor-associated protein |
| AA127170 | 502738 | acid phosphatase 2, lysosomal |
| AA151555 | 503115 | mutL homolog PMS2 |
| AA151583 | 503146 | prostaglandin E2 receptor, EP3 subtype |
| AA131511 | 503525 | bcl-6 |
| AA133853 | 503612 | protein kinase, cAMP-dependent, catalytic, beta |
| AA131709 | 503869 | epidermal growth factor receptor kinase substrate 8 |
| AA130179 | 504090 | Stat5A |
| AA133993 | 504138 | calmodulin |
| AA130219 | 504164 | hnRNP E-1 |
| AA151567 | 504347 | Rad6A |
| AA151070 | 504896 | CRADD |
| AA142907 | 505132 | regulator of chromosome condensation (RCC1) |
| AA142866 | 504375 | cellular apoptosis susceptibility protein |
| N99070 | 505877 | junB |
| AA194838 | 664989 | integrin beta-6 |
| AA195182 | 665314 | SMAD3 |
| AA195321 | 665324 | neuroendocrine convertase 2 |
| AA253089 | 667085 | renin |
| AA242743 | 668262 | XP-A |
| AA234523 | 668388 | Macrophage scavenger receptor (MSR)I/ll |
| AA236659 | 687850 | Patched |
| AA235927 | 687970 | ERK2 |
| AA284985 | 714160 | Ku(86kDa subunit) |
| AA410788 | 724317 | integrin beta-3 |
| AA291790 | 724701 | integrin beta-5 |
| AA291505 | 724805 | smooth muscle protein 22-alpha |
| AA394198 | 725709 | Trypsinogen I |
| AA292229 | 725816 | CD25 |
| AA292230 | 725818 | bcl-3 |
| AA292409 | 725875 | DNA polymerase gamma |
| AA292302 | 725883 | TFIIS |
| AA399446 | 726030 | testicular angiotensin converting enzyme |
| AA293360 | 726031 | activin receptor II |
| AA293432 | 726144 | integrin alpha-3 |
| AA293368 | 726153 | Ku (70kDa subunit) |
| AA397905 | 726506 | Thrombin receptor |
| AA394212 | 726536 | tristetraproline (zinc-finger transcriptional regulator) |
| AA398273 | 726722 | tyrosine-protein kinase receptor FLT4 (VEGF3 receptor) |
| AA398424 | 726898 | reticulin |
| AA435903 | 728710 | COUP transcription factor (V-erbA related ear-3 protein) |
| AA398782 | 729256 | cap-binding protein eIF-4E |
| AA421225 | 739222 | TNRF2-TRAF associated IAP |
| AA478022 | 740445 | ESTs, Highly similar to DNA damage response protein kinase DUN1 |
| AA401543 | 742536 | FHF4 |
| AA400276 | 742657 | heparin-binding EGF-like growth factor |
| AA411316 | 755032 | MAD2 |
| AA423811 | 755456 | IGF binding protein 2 |
| AA496426 | 755832 | placental ribonuclease/angiogenin inhibitor |
| AA496611 | 755964 | natriuretic peptide receptor |
| AA482111 | 756377 | collagenase inhibitor |
| AA429058 | 756936 | monoamine oxidase |
| AA496096 | 757144 | Activin B-c chain |
| AA442853 | 757873 | P35 regulatory subunit of CDK5 |
| AA393689 | 758424 | AKT (rac protein kinase) |
| AA442793 | 758863 | fibrinogen receptor (glycoprotein IIb) |
| AA444171 | 759500 | ALK-3 |
| AA424414 | 760179 | peripherin (RDS) |
| AA418421 | 767295 | merlin |
| AA426526 | 768137 | CD40 |
| AA429144 | 769750 | beta-galactosidase |

-continued

| GenBankID | CloneID | Gene or Marker |
|---|---|---|
| AA405452 | 772116 | prostaglandin E receptor, EP1 |
| AA441865 | 774635 | angio-associated migratory cell protein |
| AA442193 | 774731 | nuclear respiratory factor 2 beta subunit 1 |
| AA432381 | 782115 | nitric oxide synthase, inducible |
| AA476747 | 784605 | Death receptor 3 (DR3) |
| AA448430 | 784836 | CPP32 |
| AA448311 | 784866 | neurotrophin-3 |
| AA451970 | 786611 | vacuolar ATP synthase subunit AC39 |
| AA452575 | 788513 | MAD-related protein MADR1 |
| AA452691 | 788830 | p33ING1 |
| AA461579 | 795729 | BAD protein |
| AA461131 | 796251 | nuclear respiratory factor 1 |
| AA461028 | 796724 | FGF-5 |
| AA463285 | 796875 | RagB |
| AA463252 | 797061 | retinoic acid receptor (RAR) g |
| AA464261 | 810149 | vitamin D3 25-hydroxylase |
| AA464064 | 810276 | adenovirus E1A enhancer binding protein |
| AA455830 | 811619 | beta galactosidase-related protein |
| AA463854 | 811669 | alpha-galactosidase A |
| AA463610 | 811740 | integrin alpha 2 |
| AA447751 | 813654 | tyrosine hydroxylase |
| AA453898 | 813751 | Gal-beta(1-3/1-4)GlcNAc alpha-2.3-sialyltransferase |
| T66180 | 22074 | c-erbA (thyroid hormone receptor alpha-2) |
| T90176 | 110491 | integrin alpha-V (vitronectin receptor) |
| T84505 | 111589 | GATA4 |
| T96440 | 121045 | protocadherin 42 |
| R00364 | 123034 | follistatin |
| R01267 | 124182 | MnSOD |
| R06576 | 126414 | erythrocyte adducin beta subunit |
| R08170 | 127204 | 5-hydroxytryptamine 5-HT |
| R08797 | 127794 | integrin alpha-8 |
| R10506 | 129059 | interleukin-7 receptor alpha chain |
| R17566 | 32211 | bcl-x |
| R43551 | 32790 | DNA mismatch repair protein MSH2 |
| R44739 | 34140 | grancalcin |
| R54278 | 39576 | DNA repair protein RAD8 |
| R60890 | 42716 | TRAP3 (TNF receptor 2-associated) |
| R26041 | 132742 | prostacylin receptor |
| R28464 | 133175 | B2-microglobulin |
| R27799 | 133791 | bone morpho |
| R33129 | 136142 | fibulin 1 isoform B |
| R37527 | 137257 | sodium-dependent noradrenaline transporter |
| R39428 | 137531 | protein-tymsine phosphatase gamma |
| R74183 | 143332 | neuropeptide Y receptor Y1 |
| R80734 | 147166 | AP-2 |
| H13926 | 148121 | keratin, type II cytoskeletal7 |
| R82780 | 149809 | endothelial transcription factor GATA-2 |
| R70391 | 155268 | placental ribonuclease inhibitor (angiogenin inhibitor) |
| R72822 | 156169 | alkaline phosphatase, liver/bone/kidney-type |
| H27549 | 162744 | cytochrome P450-IIB6 |
| H27128 | 163187 | hADAMTS-1 (inflammation-associated) |
| H06193 | 43622 | glutamate receptor 2' |
| H06292 | 44205 | DNA-binding protein SATB1 |
| H05445 | 44563 | neuromodulin |
| H09305 | 45788 | adenosine A2A receptor |
| H11363 | 47641 | hTAFII31 |
| H18558 | 51204 | mitochondrial transcription factor 1 |
| H21044, | 51450 | adenosine A1 receptor |
| H29638 | 52669 | neurotensin receptor |
| H18585 | 171934 | prostaglandin D synthase |
| H19608 | 172755 | neuron-specific growth-associated protein / stathmin homolog |
| H43854 | 184240 | MMP-like, disintegrin-like, cysteine-rich protein (MDC) |
| R87278 | 185789 | GABA-noradrenaline receptor |
| H44230 | 186409 | bullous pemphigoid antigen (230 kDa) |
| H38423 | 192400 | FGF9 (GLIA-activating factor) |
| R89150 | 195614 | phenylalanine hydroxylase |
| R97461 | 199520 | beta-actin |
| R97705 | 200264 | hTAFII80 |
| H68922 | 212078 | integrin alpha 1 subunit (laminin receptor) |
| H86819 | 220383 | radixin |
| H93754 | 220841 | fodrin alpha chain |
| H79481 | 229419 | cathepsin E |
| H75460 | 230608 | alpha-actinin 1 |
| H92788 | 231963 | ROD CGMP-specific 3',5'-cyclic phosphodiesterase beta-subunit |
| H79047 | 233721 | IGF binding protein 2 |

-continued

| GenBankID | CloneID | Gene or Marker |
|---|---|---|
| H95366 | 234487 | beta-arrestin 2 |
| H53620 | 236055 | interleukin-3 receptor alpha chain |
| H90431 | 241489 | beta-2 adrenergic receptor |
| H80711 | 241481 | MCH4 |
| H94471 | 243159 | apoptosis inhibitor, neuronal |
| N55009 | 245403 | TGF beta-induclible protein |
| N53057 | 246524 | hCHK1 |
| N59524 | 248626 | placenta growth factor, VPF/VEGF-related |
| H97669 | 251528 | endothelin B receptor |
| H94631 | 256283 | DHFR |
| N40113 | 257777 | prostate-specific transglutaminase |
| N29874 | 259941 | creatin kinase |
| H99810 | 262991 | 5,10-methylenetetrahydrofolate dehydrogenase-cyclohydrolase |
| N27582 | 264523 | ribosomal protein S9 |
| N20999 | 265880 | plectin |
| N22737 | 266581 | peroxisome assembly factor-1 |
| N40099 | 269815 | inhibin beta A chain |
| N36174 | 272690 | 5-hydroxytryptamine 2B (seratonini)receptor |
| N36408 | 273053 | fos-related antigen fra2 |
| N37000 | 273653 | TRAF-interacting protein I-TRAF |
| N39116 | 276562 | cytochrome C1 |
| N47667 | 277404 | nitric-oxide synthase, brain, endthelial cell |
| N50321 | 280371 | 5-hydroxytryptamine 2C receptor |
| N47312 | 280507 | HPRT |
| N48061 | 281704 | protein kinase C beta I |
| N51506 | 282109 | prolyl 4-hydroxylase alpha subunit |
| N64756 | 284546 | glial fibrillary acidic protein |
| W02314 | 291962 | hTAFII130 |
| N62564 | 292385 | ankyrin R (erythrocytic) |
| N71388 | 294171 | Ku(p70) |
| N69896 | 297711 | desmin |
| W03835 | 298314 | SP1 |
| N74133 | 298423 | thymidylate synthase |
| W16819 | 301735 | transglutaminase 3 |
| W23646 | 306605 | beta-nerve growth factor |
| W21383 | 307932 | DP2 (E2F dimerization partner) |
| W24978 | 308571 | thymidine kinase, cytosolic |
| N94421 | 309588 | D-dopachrome tautomerase |
| W24327 | 310007 | ICAM-3 |
| W24142 | 310059 | integrin a5 (fibronectin receptor) |
| W24215 | 310071 | calreticulin |
| W24242 | 310112 | transglutaminase 1 |
| W31027 | 310424 | protein disulfide isomerase |
| W38643 | 320810 | stress activated protein kinase |
| W32474 | 321529 | RAS-related protein RAP-2A |
| W15390 | 322710 | alk-3 |
| 323114 | 323114 | integrin beta1 fibronectin receptor beta subunit |
| W46304 | 323930 | lysyl oxidase |
| W51760 | 324383 | heparin-binding growth factor precursor 2 |
| W49779 | 324921 | metal-regulatory transcription factor (MTF-1) |
| W48845 | 325148 | vimentin |
| AA037243 | 325898 | folate receptor gamma |
| W61034 | 326158 | MEK3 |
| W63567 | 326252 | hTAFII28 |
| W30956 | 327165 | maspin (tumor suppressor) |
| W57704 | 340971 | CGMP-gated cation channel protein (rod) |
| W60659 | 341810 | MAD3(IkBalpha) |
| W61162 | 342291 | annexin V |
| W68588 | 342570 | collagen alpha 1(VII) |
| W74489 | 344642 | neuromedin B precursor |
| W77832 | 345928 | MAD |
| W72751 | 346130 | spr1 protein (cornifin B) |
| W78163 | 346900 | proto-oncogene ets-2 |
| W92764 | 357031 | hyaluronate-binding protein TSG-6 (TNF-inducible) |
| W96211 | 358596 | ornithine decarboxylase |
| W94746 | 358903 | ERCC5 (XP-G) |
| AA010411 | 359434 | TAN-1 (human homologue of notch) |
| AA062943 | 359914 | melanoma derived growth regulatory protein MIA |
| AA056355 | 359925 | E-selectin |
| AA019018 | 363207 | ankyrin 2 (brain) |
| AA019775 | 363577 | 2',3'-cyclic nucleotide 3'-phosphodiesterase |
| AA020847 | 363721 | CD40 |
| AA024754 | 364936 | monocyte chemotactic protein 1 (IFN gamma-inducible) |
| AA026047 | 365836 | desmoplakin 1 |
| AA029502 | 366822 | ciliary neurotrophic factor receptor |
| AA055376 | 377475 | junD |

-continued

| GenBankID | CloneID | Gene or Marker |
|---|---|---|
| AA056154 | 380878 | rhodopsin |
| AA062992 | 382193 | folate carrier |
| AA074111 | 383172 | retinal rod rhodopsin-sensitive CGMP |
| W87498 | 416941 | 8-oxoguanine DNA glycosylase |
| W88810 | 417522 | rho8 |
| W90256 | 418011 | hTAFII30 |
| AA005397 | 428541 | interleukin-2 receptor alpha chain |
| AA011378 | 429508 | interleukin-4 receptor alpha chain |
| AA034039 | 429893 | interleukin-6 receptor beta chain(gp130 IL-6 signal transduecer) |
| AA026957 | 469346 | DNA-3-methyladenine glycosidase |
| AA031889 | 470819 | prostaglandin E2 receptor, EP2 subtype |
| AA035361 | 471667 | STAT1 |
| AA036944 | 472067 | glial maturation factor beta |
| AA036987 | 484576 | retinoid binding protein II |
| AA037699 | 484975 | TGF-binding protein (endoglin) |
| AA039960 | 485744 | thromboxane A2 receptor |
| AA043580 | 487097 | band 4.1-type protein phosphatase (PTP1E) |
| AA059307 | 487256 | collagenase inhibitor (metalloproteinase inhibitor 1) |
| AA047396 | 488499 | CHUK (protein kinase) |
| AA045013 | 488734 | guanine nucleotide-binding protein G(I), alpha-2 subunit |
| AA054505 | 489395 | PDGF-alpha receptor |
| AA054612 | 489458 | melanoma growth stimulatory activity protein |
| AA114976 | 489919 | tenascin-X |
| AA115138 | 491591 | HIC-5 |
| AA127988 | 501830 | laminin S B3 chain |
| AA151613 | 503189 | VEGF-C |
| AA131744 | 503931 | interleukin 1b |
| AA142866 | 504375 | cellular apoptosis susceptibility protein |
| AA149811 | 505122 | thrombospondin 2 |
| AA152071 | 505169 | Cu/ZnSOD |
| AA146957 | 505434 | Id-3 |
| AA193465 | 665964 | interleukin-6 receptor alpha chain |
| AA227856 | 667494 | HOX-9 |
| AA228134 | 667587 | CGMP-dependent protein kinase, beta isozyme |
| AA253491 | 669404 | NFIL-6 |
| AA256859 | 682268 | XP-F (RAD16) |
| AA291382 | 725236 | ets domain protein ERF |
| AA292292 | 725863 | envoplakin |
| AA293050 | 726147 | MEK4 (JNK activating kinase 1) |
| AA394051 | 726015 | hTAFII15/20 |
| AA399327 | 726687 | High-affinity nerve growth factor receptor (CCK4) |
| AA398472 | 726955 | talin |
| AA402573 | 727429 | prostacyclin-stimulating factor |
| AA435803 | 728441 | AMD-related protein MADR1 |
| AA469911 | 730012 | inhibin bB |
| AA417113 | 730831 | hTAFII55 |
| AA477173 | 740559 | APO-2 ligand |
| AA401408 | 743173 | Ets transcription factor (NERF-2) |
| AA419504 | 752527 | TBP |
| AA410998 | 752531 | hTAFII18 |
| AA481364 | 756512 | IL4-stat (Stat2) |
| AA429386 | 757125 | interferon-inducible protein 9-27 |
| AA442290 | 757440 | IL-10 receptor |
| AA436841 | 757798 | IkB-beta |
| AA437026 | 757875 | P35 regulatory subunit OF CDK5 kinase |
| AA425781 | 768938 | protein-tyrosine phosphatase zeta |
| AA430370 | 769863 | neuroendocrine protein 7B2 |
| AA427694 | 770458 | transcriptional repressor protein YY1 |
| AA434485 | 770862 | VEGF-B |
| AA443491 | 771182 | rantes |
| AA429941 | 774458 | ARNT interacting protein |
| AA429828 | 774488 | retinoic acid-responsive protein |
| AA446300 | 781017 | response protein 2 |
| AA447044 | 783832 | TIMP1 |
| AA447093 | 784307 | guanine nucleotide-binding protein G(O), alpha subunit 1 |
| AA443746 | 784693 | transcription initiation factor IIB |
| AA449817 | 788628 | beta-fodrin |
| AA461595 | 795764 | JNK3 |
| AA455521 | 809828 | E2F5 |
| AA464339 | 809895 | cytochrome b |
| AA464549 | 810532 | osteocalcin |
| AA459289 | 810891 | laminin alpha 5 |
| AA463640 | 811839 | galactosyltransferase associated protein kinase P58/GTA |
| AA447811 | 813588 | A28-RGS14 (p53-induced) |
| W93076 | 415078 | platelet endothelial cell adhesion molecule |
| N98621 | 310141 | GADD45 |

-continued

| GenBankID | CloneID | Gene or Marker |
|---|---|---|
| AA293501 | 726105 | 80K-L |
| R11743 | 29451 | XRCC1 |
| R56376 | 41159 | retinoic acid-responsive protein |
| R72114 | 155691 | melanocyte stimulating hormone receptor |
| H08293 | 45393 | neuronal membrane glycoprotein M6a |
| H16874 | 50121 | polypeptide N-acetylgalactosaminyltransferase |
| H24357 | 52193 | glial growth factor |
| H28884 | 186359 | nestin |
| R91570 | 196543 | Stat4 |
| R93509 | 197780 | stress responsive serine/threonine protein kinase Krs-2 |
| R96927 | 200378 | DNA repair protein RAD52 homolog |
| H58247 | 204519 | cathepsin E |
| H65504 | 209310 | NF-kB p65 |
| N80251 | 300373 | prostaglandin D synthase |
| W31804 | 320448 | cytochrome C1 |
| W37467 | 322057 | gelsolin |
| W46538 | 323858 | ferritin heavy chain |
| W68199 | 342425 | hic-1 |
| W69278 | 343659 | TRADD |
| W72209 | 345978 | Somatostatin |
| AA058479 | 380914 | S1-5 |
| AA058467 | 381144 | inositol polyphosphate 5-phosphatase |
| AA057233 | 381287 | S-arrestin |
| AA034008 | 429877 | parathyroid hormone-related peptide receptor |
| AA032091 | 470934 | plasminogen activator inhibitor-2 (PAI-2) |
| AA039846 | 485445 | DNA-binding protein inhibitor ID-1 |
| N70362 | 295412 | rad51 |
| AA453262 | 795351 | transcription factor TFIIE |
| AA455167 | 813309 | lysosome-associated membrane glycoprotein 2 |
| AA497033 | 823562 | cycteine dioxygenase |
| R92425 | 196296 | cytochrome P450 IIIA5 |
| T89901 | 116801 | cyclin F |
| R14366 | 28689 | transcription factor ITF-2 (beta catenin associated) |
| R41330 | 30149 | bone/kidney alkaline phosphatase (HALP) |
| R59027 | 41133 | phospholipase C, alpha |
| R26041 | 132742 | prostacyclin receptor |
| R67110 | 140842 | TGF breceptor type 3 |
| R77649 | 145457 | kinase suppressor of ras-1 KSR1 |
| H02648 | 150817 | importin-alpha3 |
| R54648 | 154444 | PIG11 |
| H15031 | 159431 | Endothelial cell nitric oxide synthase (EcNOS) |
| H25546 | 161456 | serum amyloid A protein (PIG4) |
| H09149 | 46513 | asialpglycoprotein receptor 1 |
| H10622 | 47297 | guanine nucleotide-binding protein Rar |
| H11660 | 48285 | PIG11 |
| H29571 | 52681 | transcription factor RELB |
| R89116 | 195539 | Thyroxin binding protein |
| H84047 | 249856 | p107 |
| N29280 | 264567 | TNF alpha-induced (PIG7) |
| R85714 | 275252 | synaptophysin |
| N95705 | 277923 | transcription factor IIF, beta subunit |
| N53900 | 281598 | Human tax1-binding protein TXBP181 (PIG9) |
| N90388 | 292637 | transferrin |
| N91624 | 293102 | heme oxygenase |
| W07320 | 300208 | PIG3, quinone oxidoreductase homologue |
| N89806 | 305482 | parathyroid hormone |
| W46929 | 324583 | guanidinoacetate N-methyltransferase (PIG2) |
| W67443 | 343305 | galectin-5 (PIG1) |
| W69471 | 343646 | ski oncogene |
| W72479 | 345449 | SMAD6 |
| AA010298 | 359250 | carbonic anhydrase IV |
| AA011239 | 359434 | notch protein homolog TAN-1 |
| AA015637 | 360481 | proline oxidase homologue (PIG6) |
| AA021106 | 364038 | GAPDH |
| AA054037 | 380223 | neural retina leucine zipper |
| AA074145 | 383098 | proline oxidase homologue (PIG6) |
| AA035313 | 471668 | protein kinase, cAMP-dependent, regulatory, type I, alpha |
| AA400745 | 727698 | protein tyrosine phosphatase, receptor type, DEP-1 |
| AA421179 | 739215 | peroxisome proliferator activated receptor beta |
| AA400982 | 741429 | protein kinase, ERK3-related, 63 kDa subunit |
| AA410905 | 756001 | Human ARNT interacting protein |
| AA429265 | 757035 | normal keratinocyte mRNA (PIG 5) |
| AA478497 | 784696 | PIG3, quinone oxidoreductase homologue |
| AA453227 | 789309 | TNF alpha-induced (PIG7) |
| AA458609 | 813086 | normal keratinocyte mRNA (PIG 5) |
| AA453682 | 813654 | tyrosine 3-monooxygenase |
| T86605 | 115240 | CCG1 (TFIID 250 kDa subunit) |

-continued

| GenBankID | CloneID | Gene or Marker |
|---|---|---|
| R36886 | 25807 | glutamate receptor 3 precursor |
| H85361 | 222197 | ABCR |
| W23646 | 306605 | nerve growth factor beta (beta-NGF) |
| AA085743 | 488254 | interferon gamma receptor beta chain |
| AA411763 | 730653 | Human DNA mismatch repair (hmlh1) |
| AA478589 | 753610 | apolipoprotein E precursor |
| AA442523 | 758772 | non-specific alkaline phosphatase |
| AA430751 | 773724 | FADD |
| AA527557 | 937420 | skin-derived antileukoproteinase (elafin) |
| W52121 | 338424 | laminin gamma-2 |
| AA074388 | 531673 | cytochrome c oxidase (COX) subunit III |
| AA480209 | 898903 | Bloom's syndrome gene |
| AA484941 | 815798 | BRCA1 |
| AA081686 | 937234 | tumor suppressor protein DCC |
| T92918 | 118629 | Keratin 4 |
| AA133469 | 586796 | keratin, type I cytoskeletal20 |
| T68473 | 83395 | tyrosine amino transferase |
| AA055586 | 510383 | interferon-inducible protein 9-27 |
| T68115 | 83139 | ESTs, Highly similar to epidermal growth factor |
| T64105 | 79829 | epidermal growth factor receptor HER4, ERBB4 |
| AA205710 | 646846 | epidermal growth factor-like cripto protein |
| AA191012 | 937216 | leptin receptor |
| AA229062 | 1011516 | androgen receptor |
| AA101473 | 563711 | epidermal growth factor-like CRIPTO protein (teratocarcinoma) |
| T52484 | 72869 | nerve growth factor beta (beta-NGF) |
| AA053166 | 510275 | peroxisome proliferator activated receptor gamma |
| AA194415 | 628595 | ryanodine receptor, skeletal muscle |
| T57875 | 71622 | protein kinase C zeta |
| AA284634 | 713193 | Jak1 |
| AA226546 | 1009247 | cap-binding protein cbp20 |
| AA459003 | 814272 | A-myb |
| T64105 | 79829 | ERBB4 |
| AA196887 | 645991 | RAB-3B |
| AA143087 | 592125 | RIP kinase |
| AA551834 | 996687 | CD40 ligand |
| AA053668 | 510375 | tumor necrosis factor type 2 receptor associated protein (TRAP3) |
| AA291199 | 700616 | XP-F repair endonuclease (rad16) |
| AA226171 | 1007868 | neuropeptide Y precursor |
| AA251994 | 684859 | hTAFII100 |
| AA568106 | 913625 | hTAFII68 |
| AA569377 | 1057458 | mitogen-activated protein kinase P38 (alpha) |
| T63549 | 81434 | arachidonate 12-lipoxygenase |
| AA558448 | 1015862 | beta-galactoside alpha-2,3-sialyltransferase hTR |
| R72863 | 157815 | retinoic acid receptor a |
| W19257 | 302808 | filagrin |
| AA291749 | 725321 | estrogen receptor TPC2 TPC3 H1 histamine receptor protein hTRT |

Those of skill in the art will recognize that, while use of each of the clones above is preferred in one embodiment of the invention, the invention encompasses the use of any subset of the clones that can be derived from the list of clones above. The clones can be produced by PCR amplification of plasmid inserts from selected bacterial clones using the two primers shown below: T7T3-pac-L 5'-GGCGATTAAGTTGGGTAACG 3' (SEQ ID NO. 28); and AB15'-GAATTGTGAGCGGATAAC 3' (SEQ ID NO. 29). Both primers were synthesized to have a modified amine residue (C6-TFA) at their 5'terminii. Certain of the clones were prepared as described below.

The H1 histamine receptor protein cDNA was amplified from cDNA prepared from total RNA using the sequence-specific, amine-modified primers shown below:

H15': 5' GGCCTTCGTCCTCTATTTCC (SEQ ID NO. 30); and

H13': 5' GCCGTCCTCTCTGCCTCTTT (SEQ ID NO. 31).

The hTR clone was amplified from plasmid pGRN83 (see also pGRN33, available from the ATCC; see U.S. Pat. No. 5,583,016) using the amine-modified primers shown below:

hTR445 comp: 5' GCATGTGTGAGCCGAGTC-CTGGGTGCA (SEQ ID NO. 32); and hTR S328: 5' TTGGGCTCTGTCAGCCGCGGGTCTCT (SEQ ID NO. 33).

The TPC2 clone was prepared using a two-part amplification strategy. First, primers 109-5' and AB1 used to amplify the clone from plasmid pGRN109 (see U.S. patent application Ser. No. 08/710,249, filed Sep. 13, 1996). This fragment was subcloned into plasmid pCR2.1 (InVitrogen, Inc.), and a subsequent amplification with amine-modified primers AB1 and T7T3-pac-L was performed to generate the final PCR product. The novel primer used is shown below:

109-5': 5' TGCGGTCGTATGTCAGTGAG (SEQ ID NO. 34).

The TPC3 clone was prepared using a two-part amplification strategy. First, primers 92-5' and AB1 were used to amplify from plasmid pGRN92 (see U.S. patent application Ser. No. 08/710,249, filed Sep. 13, 1996). This fragment was subcloned into plasmid pCR2.1 (InVitrogen, Inc.), and a subsequent amplification with amine-modified primers AB1 and T7T3-pac-L was performed to generate the final PCR product. The novel primer used is shown below:

92-5': 5' GAGAAGTCAATGCCCATCAC (SEQ ID NO. 35).

The hTRT clone was prepared using a two-part amplification strategy. First, primers 121-5' and AB1 were used to amplify from plasmid pGRN121 (see U.S. patent application Ser. Nos. 08/911,312, and 912,951, both filed Aug. 14, 1997). This fragment was subcloned into plasmid pCR2.1 (InVitrogen, Inc.), and a subsequent amplification with amine-modified primers AB1 and T7T3-pac-L was performed to generate the final PCR product. The novel primer used is shown below: 121-5': 5'TGCGGTCGTATGTCAGTGAG (SEQ ID NO. 36).

Example 6

Assay for PGC6 Activity

One can also detect GC6 gene products by an activity assay. The primary amino acid sequence of pGC6 shares approximately 30% identity with DBH. Human DBH contains 15 cysteine residues which, by analogy to studies on the bovine form of DBH (Robertson et al., 1994), are predicted to form multiple intermolecular disulfide linkages. These linkages tend to constrain the protein into an ordered conformation. A comparison of human DBH with pGC6 shows that 11 of these 15 cysteine residues are conserved, suggesting a highly similar conformation. The catalytic activity of DBH requires copper ions as a co-factor. A proposed mechanism for the monooxygenase activity suggests that the protein binds metal at histidyl-rich sites (approximately residues 230 to 500 of human DBH). Overall, this region is the most highly conserved between human DBH and pGC6, with 8 of 12 histidyl residues identical. Thus, the primary sequence not only suggests a similar overall folding pattern for the two proteins, but also a conserved catalytic activity.

The monooxygenase activity of DBH is well-described and requires an electron donor, oxygen, copper, and an appropriate substrate. DBH has a relatively relaxed substrate specificity and will convert most phenylethylamines to their corresponding phenyethanolamines. A convenient spectrophotometric assay has been described (Wimalasena and Wimalasena, 1991, *Analyt. Biochem.* 197: 353–361, incorporated herein by reference) that uses N,N'-dimethyl-1,4,phenylenediamine (DNPD) as an electron donor and tyramine as a substrate. This assay can be used to monitor the acitivity of pGC6 directly from extracts of cells in which the protein is expressed, either naturally or as the result of the expression of a pGC6 transgene. Alternatively, as has been described for human DBH (Li et al.,1995, *Biochem. J.* 313: 57–64), the pGC6 protein can be expressed in heterologous cells, such as *Drosophila sheider* cells, purified by conventional means, and assayed as a partially purified preparation.

The foregoing examples describe various aspects of the invention and how the methods of the invention can be practiced. The examples are not intended to provide an exhaustive description of the many different embodiments of the invention.

All publications and patent applications cited above are hereby incorporated herein by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule encoding an amino acid sequence as shown in SEQ ID No: 15.

2. A recombinant nucleic acid molecule comprising a promoter sequence operably linked to a nucleic acid molecule according to claim 1.

3. A recombinant nucleic acid vector comprising a nucleic acid molecule according to claim 1.

4. A host cell comprising a recombinant nucleic acid molecule according to claim 2.

5. A host cell comprising a recombinant nucleic acid vector according to claim 3.

6. An isolated nucleic acid molecule according to claim 1, wherein the molecule comprises the nucleic acid sequence shown in SEQ ID No: 16.

7. A recombinant nucleic acid molecule comprising a promoter sequence operably linked to a nucleic acid molecule according to claim 6.

8. A recombinant nucleic acid vector comprising a nucleic acid molecule according to claim 6.

9. A host cell comprising a recombinant nucleic acid molecule according to claim 7.

10. A host cell comprising a recombinant nucleic acid vector according to claim 8.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..22
      (D) OTHER INFORMATION: /note= "3' primer "E""

(xi) SEQUENCE DESCRIPTION: SEQ ID NO:1:

GCGCAAGCTT TTTTTTTTTT GG          22

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "5' primer "11""

(xi) SEQUENCE DESCRIPTION: SEQ ID NO:2:

CGGGAAGCTT ACTCCATGAC TC                                                22

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..39
        (D) OTHER INFORMATION: /note= ""11E3" "genetag""

(xi) SEQUENCE DESCRIPTION: SEQ ID NO:3:

AGGGGCACAA GAGTTTGCGG TTATTGAATC CTGAGANAA                               39

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC47"

(xi) SEQUENCE DESCRIPTION: SEQ ID NO:4:

GCAGGAAGGC GGCACGAGAG                                                   20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC48"

(xi) SEQUENCE DESCRIPTION: SEQ ID NO:5:

TTGTATCTTT GTTTGGGATG                                                   20

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..28
        (D) OTHER INFORMATION: /note= "primer KJC42"

(xi) SEQUENCE DESCRIPTION: SEQ ID NO:6:

TAGGCCCAGA TCACTCTCAC AGTGCTAT                                              28

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..28
        (D) OTHER INFORMATION: /note= "primer gt11"

(xi) SEQUENCE DESCRIPTION: SEQ ID NO:7:

CACCAGACCA ACTGGTAATG GTAGCGAC                                              28

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "primer KJC51"

(xi) SEQUENCE DESCRIPTION: SEQ ID NO:8:

ATACCGCTCG AGCGGACCTG ATTCCCCAGT TGG                                        33

(2) INFORMATION FOR SEQ ID NO:9:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..345
        (D) OTHER INFORMATION: /note= "PCR product KJC51-KJC42"

(xi) SEQUENCE DESCRIPTION: SEQ ID NO:9:

ATACCGCTCG AGCGGACCTG ATTCCCCAGT TGGAATACTC CAGCCCCTTG GAAATTCCCG           60

GGATTTATAA AATAACTCTA GACAACAAGA CTTTGTCTTT AAAGGTCCTA TGAATTCTTT          120

```
TCTCTCTGTA TTTANGTATC CTGATTTTTC TTTTCCATAT TTTCCACAGG ATTATTTTAC         180

AAATGCAAAT AGAGAGTTGA AAAAAGATGC TCAGCAAGAT TACCATCTAG AATATGCCAT         240

GGAAAATAGC ACACACACAA TAATTGAATT TACCAGAGAG CTGCATACAT GTGACATAAA         300

TGACAAGAGT ATAACGGATA GCACTGTGAG AGTGATCTGG GCCTA                        345

(2) INFORMATION FOR SEQ ID NO:10:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..230
        (D) OTHER INFORMATION: /note= "restriction fragment 5'GC6
            XhoI/NcoI"

(xi) SEQUENCE DESCRIPTION: SEQ ID NO:10:

TCGAGCGGAC CTGATTCCCC AGTTGGAATA CTCCAGCCCC TTGGAAATTC CCGGGATTTA          60

TAAAATAACT CTAGACAACA AGACTTTGTC TTTAAAGGTC CTATGAATTC TTTTCTCTCT         120

GTATTTANGT ATCCTGATTT TTCTTTTCCA TATTTTCCAC AGGATTATTT TACAAATGCA         180

AATAGAGAGT TGAAAAAAGA TGCTCAGCAA GATTACCATC TAGAATATGC                   230

(2) INFORMATION FOR SEQ ID NO:11:

(i) SEQUENCE CHARACTERISTICS:
        (A) LENGTH: 2178 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..2178
        (D) OTHER INFORMATION: /note= "restriction fragment GC6
            NcoI/XbaI, 3' end fragment of pGC61"

(xi) SEQUENCE DESCRIPTION: SEQ ID NO:11:

CATGGAAAAT AGCACACACA CAATAATTGA ATTTACCAGA GAGCTGCATA CATGTGACAT          60

AAATGACAAG AGTATAACGG ATAGCACTGT GAGAGTGATC TGGGCCTACC ACCATGAAGA         120

TGCAGGAGAA GCTGGTCCCA AGTACCATGA CTCCAATAGG GGCACCAAGA GTTTGCGGTT         180

ATTGAATCCT GAGAAAACTA GTGTGCTATC TACAGCCTTA CCATACTTTG ATCTGGTAAA         240

TCAGGACGTC CCCATCCCAA ACAAAGATAC AACATATTGG TGCCAAATGT TTAAGATTCC         300

TGTGTTCCAA GAAAAGCATC ATGTAATAAA GGTTGAGCCA GTGATACAGA GAGGCCATGA         360

GAGTCTGGTG CACCACATCC TGCTCTATCA GTGCAGCAAC AACTTTAACG ACAGCGTTCT         420

GGAGTCCGGC CACGAGTGCT ATCACCCCAA CATGCCCGAT GCATTCCTCA CCTGTGAAAC         480

TGTGATTTTT GCCTGGGCTA TTGGTGGAGA GGGCTTTTCT TATCCACCTC ATGTTGGATT         540

ATCCCTTGGC ACTCCATTAG ATCCGCATTA TGTGCTCCTA GAAGTCCATT ATGATAATCC         600

CACTTATGAG GAAGGCTTAA TAGATAATTC TGGACTGAGG TTATTTTACA CAATGGATAT         660

AAGGAAATAT GATGCTGGGG TGATTGAGGC TGGCCTCTGG GTGAGCCTCT TCCATACCAT         720
```

```
CCCTCCAGGG ATGCCTGAGT TCCAGTCTGA GGGTCACTGC ACTTTGGAGT GCCTGGAAGA       780

GGCTCTGGAA GCCGAAAAGC CAAGTGGAAT TCATGTGTTT GCTGTTCTTC TCCATGCTCA       840

CCTGGCTGGC AGAGGCATCA GGCTGCGTCA TTTTCGAAAA GGGAAGGAAA TGAAATTACT       900

TGCCTATGAT GATGATTTTG ACTTCAATTT CCAGGAGTTT CAGTATCTAA AGGAAGAACA       960

AACAATCTTA CCAGGAGATA ACCTAATTAC TGAGTGTCGC TACAACACGA AGATAGAGC       1020

TGAGATGACT TGGGGAGGAC TAAGCACCAG GAGTGAAATG TGTCTCTCAT ACCTTCTTTA      1080

TTACCCAAGA ATTAATCTTA CTCGATGTGC AAGTATTCCA GACATTATGG AACAACTTCA      1140

GTTCATTGGG GTTAAGGAGA TCTACAGACC AGTCACGACC TGGCCTTTCA TTATCAAAAG      1200

TCTCAAGCAA TATAAAAACC TTTCTTTCAT GGATGCTATG AATAAGTTTA AATGGACTAA      1260

AAAGGAAGGT CTCTCCTTCA ACAAGCTGGT CCTCAGCCTG CCAGTGAATG TGAGATGTTC      1320

CAAGACAGAC AATGCTGAGT GGTCGATTCA AGGAATGACA GCATTACCTC CAGATATAGA     1380

AAGACCCTAT AAAGCAGAAC CTTTGGTGTG TGGCACGTCT TCTTCCTCTT CCCTGCACAG     1440

AGATTTCTCC ATCAACTTGC TTGTTTGCCT TCTGCTACTC AGCTGCACGC TGAGCACCAA     1500

GAGCTTGTGA TCAAAATTCT GTTGGACTTG ACAATGTTTT CTATGATCTG AACCTGTCAT    1560

TTGAAGTACA GGTTAAAGAC TGTGTCCACT TTGGGCATGA AGAGTGTGGA GACTTTTCTT   1620

CCCCATTTTC CCTCCCTCCT TTTTCCTTTC CATGTTACAT GAGAGACATC AATCAGGTTC   1680

TCTTCTCTTT CTTAGAAATA TCTGATGTTA TATATACATG GTCAATAAAA TAAAACTGGC   1740

CTGACTTAAG ATAACCATTT TAAAAAATTG GGCTGTCATG TGGGAATAAA AGAATTCTTT  1800

CTTTCCTACT ACATTCTGTT TTATTTAAAT ACTCATTGTT GCTATTTCAC TTTTTGACTT  1860

GACTTTTATA TTTCTTTAAA AAATTCCTTC CTTTTAAAAA ATATAAAAGG GACTACTGTT  1920

CATTCCAGTT TTCTTCTTCT TTGTTGTTCT TCTAGTGTGA CTTTTCAAGT GTAACAGCCA  1980

TTCTTCCTGA CTTTAATATT GTCCAGTTCT GGTCTTTTCT GTGAATTACC ACTGGGCCCC  2040

TTACCTCAAT GCTTTTTGTT GATGCCCACT CTGGTTCCCT TGTTTATCTG AGTCTGTTGG  2100

TACCCCAAAT GACCCCACAC CCATYTTAAA GTACTTTTTT TCACCTTCCC TGTTTAGTAC  2160

TGGCCAGATG AGTTTTTT                                                    2178

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "sequenceing primer KJC52"

(xi) SEQUENCE DESCRIPTION: SEQ ID NO:12:

TAATACGACT CACTATAG                                                      18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

-continued

```
    (ii) MOLECULE TYPE: DNA (ix) FEATURE:
         (A) NAME/KEY: -
         (B) LOCATION: 1..20
         (D) OTHER INFORMATION: /note= "sequencing primer KJC53"

(xi) SEQUENCE DESCRIPTION: SEQ ID NO:13:

ATTAACCCTC ACTAAAGGGA                                                  20

(2) INFORMATION FOR SEQ ID NO:14:

(i) SEQUENCE CHARACTERISTICS:
        (A) LENGTH: 2970 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 231..1868
         (D) OTHER INFORMATION: /product= "pGC6"

(ix) FEATURE:
         (A) NAME/KEY: -
         (B) LOCATION: 1..2970
         (D) OTHER INFORMATION: /note= "5' and 3' untranslated
             regions of GC6 cDNA and complete ORF
             of GC6 gene"

(xi) SEQUENCE DESCRIPTION: SEQ ID NO:14:
```

```
ACTTTCCAAG GAAGGAAAGG CACACAATGG TATCAAATGT TCATTCATTC CATCTCTTGA      60

TGCTCTACGA TATTATCAGT CTACACTATG CTTTCCTGAA AGGCCAGAAG TTCAAAGATG     120

GACTAGTTTC CCAGGGACCT GATTCCCCAG TTGGAATACT CCAGCCCCTT GGAAATTCCC     180

GGGATTTATA AATAACTCT AGACAACAAG ACTTTGTCTT TAAAGGTCCT ATG AAT         236
                                                        Met Asn
                                                         1

TCT TTT CTC TCT GTA TTT AGG TAT CCT GAT TTT TCT TTT CCA TAT TTT       284
Ser Phe Leu Ser Val Phe Arg Tyr Pro Asp Phe Ser Phe Pro Tyr Phe
      5                  10                  15

CCA CAG GAT TAT TTT ACA AAT GCA AAT AGA GAG TTG AAA AAA GAT GCT       332
Pro Gln Asp Tyr Phe Thr Asn Ala Asn Arg Glu Leu Lys Lys Asp Ala
 20                  25                  30

CAG CAA GAT TAC CAT CTA GAA TAT GCC ATG GAA AAT AGC ACA CAC ACA       380
Gln Gln Asp Tyr His Leu Glu Tyr Ala Met Glu Asn Ser Thr His Thr
 35                  40                  45                  50

ATA ATT GAA TTT ACC AGA GAG CTG CAT ACA TGT GAC ATA AAT GAC AAG       428
Ile Ile Glu Phe Thr Arg Glu Leu His Thr Cys Asp Ile Asn Asp Lys
                 55                  60                  65

AGT ATA ACG GAT AGC ACT GTG AGA GTG ATC TGG GCC TAC CAC CAT GAA       476
Ser Ile Thr Asp Ser Thr Val Arg Val Ile Trp Ala Tyr His His Glu
                     70                  75                  80

GAT GCA GGA GAA GCT GGT CCC AAG TAC CAT GAC TCC AAT AGG GGC ACC       524
Asp Ala Gly Glu Ala Gly Pro Lys Tyr His Asp Ser Asn Arg Gly Thr
             85                  90                  95

AAG AGT TTG CGG TTA TTG AAT CCT GAG AAA ACT AGT GTG CTA TCT ACA       572
Lys Ser Leu Arg Leu Leu Asn Pro Glu Lys Thr Ser Val Leu Ser Thr
 100                 105                 110

GCC TTA CCA TAC TTT GAT CTG GTA AAT CAG GAC GTC CCC ATC CCA AAC       620
Ala Leu Pro Tyr Phe Asp Leu Val Asn Gln Asp Val Pro Ile Pro Asn
115                 120                 125                 130

AAA GAT ACA ACA TAT TGG TGC CAA ATG TTT AAG ATT CCT GTG TTC CAA       668
```

-continued

```
Lys Asp Thr Thr Tyr Trp Cys Gln Met Phe Lys Ile Pro Val Phe Gln
            135                 140                 145

GAA AAG CAT CAT GTA ATA AAG GTT GAG CCA GTG ATA CAG AGA GGC CAT      716
Glu Lys His His Val Ile Lys Val Glu Pro Val Ile Gln Arg Gly His
            150                 155                 160

GAG AGT CTG GTG CAC CAC ATC CTG CTC TAT CAG TGC AGC AAC AAC TTT      764
Glu Ser Leu Val His His Ile Leu Leu Tyr Gln Cys Ser Asn Asn Phe
            165                 170                 175

AAC GAC AGC GTT CTG GAG TCC GGC CAC GAG TGC TAT CAC CCC AAC ATG      812
Asn Asp Ser Val Leu Glu Ser Gly His Glu Cys Tyr His Pro Asn Met
180                 185                 190

CCC GAT GCA TTC CTC ACC TGT GAA ACT GTG ATT TTT GCC TGG GCT ATT      860
Pro Asp Ala Phe Leu Thr Cys Glu Thr Val Ile Phe Ala Trp Ala Ile
195                 200                 205                 210

GGT GGA GAG GGC TTT TCT TAT CCA CCT CAT GTT GGA TTA TCC CTT GGC      908
Gly Gly Glu Gly Phe Ser Tyr Pro Pro His Val Gly Leu Ser Leu Gly
                    215                 220                 225

ACT CCA TTA GAT CCG CAT TAT GTG CTC CTA GAA GTC CAT TAT GAT AAT      956
Thr Pro Leu Asp Pro His Tyr Val Leu Leu Glu Val His Tyr Asp Asn
                230                 235                 240

CCC ACT TAT GAG GAA GGC TTA ATA GAT AAT TCT GGA CTG AGG TTA TTT     1004
Pro Thr Tyr Glu Glu Gly Leu Ile Asp Asn Ser Gly Leu Arg Leu Phe
            245                 250                 255

TAC ACA ATG GAT ATA AGG AAA TAT GAT GCT GGG GTG ATT GAG GCT GGC     1052
Tyr Thr Met Asp Ile Arg Lys Tyr Asp Ala Gly Val Ile Glu Ala Gly
            260                 265                 270

CTC TGG GTG AGC CTC TTC CAT ACC ATC CCT CCA GGG ATG CCT GAG TTC     1100
Leu Trp Val Ser Leu Phe His Thr Ile Pro Pro Gly Met Pro Glu Phe
275                 280                 285                 290

CAG TCT GAG GGT CAC TGC ACT TTG GAG TGC CTG GAA GAG GCT CTG GAA     1148
Gln Ser Glu Gly His Cys Thr Leu Glu Cys Leu Glu Glu Ala Leu Glu
                    295                 300                 305

GCC GAA AAG CCA AGT GGA ATT CAT GTG TTT GCT GTT CTT CTC CAT GCT     1196
Ala Glu Lys Pro Ser Gly Ile His Val Phe Ala Val Leu Leu His Ala
                310                 315                 320

CAC CTG GCT GGC AGA GGC ATC AGG CTG CGT CAT TTT CGA AAA GGG AAG     1244
His Leu Ala Gly Arg Gly Ile Arg Leu Arg His Phe Arg Lys Gly Lys
            325                 330                 335

GAA ATG AAA TTA CTT GCC TAT GAT GAT GAT TTT GAC TTC AAT TTC CAG     1292
Glu Met Lys Leu Leu Ala Tyr Asp Asp Asp Phe Asp Phe Asn Phe Gln
            340                 345                 350

GAG TTT CAG TAT CTA AAG GAA GAA CAA ACA ATC TTA CCA GGA GAT AAC     1340
Glu Phe Gln Tyr Leu Lys Glu Glu Gln Thr Ile Leu Pro Gly Asp Asn
355                 360                 365                 370

CTA ATT ACT GAG TGT CGC TAC AAC ACG AAA GAT AGA GCT GAG ATG ACT     1388
Leu Ile Thr Glu Cys Arg Tyr Asn Thr Lys Asp Arg Ala Glu Met Thr
                    375                 380                 385

TGG GGA GGA CTA AGC ACC AGG AGT GAA ATG TGT CTC TCA TAC CTT CTT     1436
Trp Gly Gly Leu Ser Thr Arg Ser Glu Met Cys Leu Ser Tyr Leu Leu
                390                 395                 400

TAT TAC CCA AGA ATT AAT CTT ACT CGA TGT GCA AGT ATT CCA GAC ATT     1484
Tyr Tyr Pro Arg Ile Asn Leu Thr Arg Cys Ala Ser Ile Pro Asp Ile
            405                 410                 415

ATG GAA CAA CTT CAG TTC ATT GGG GTT AAG GAG ATC TAC AGA CCA GTC     1532
Met Glu Gln Leu Gln Phe Ile Gly Val Lys Glu Ile Tyr Arg Pro Val
            420                 425                 430

ACG ACC TGG CCT TTC ATT ATC AAA AGT CTC AAG CAA TAT AAA AAC CTT     1580
Thr Thr Trp Pro Phe Ile Ile Lys Ser Leu Lys Gln Tyr Lys Asn Leu
435                 440                 445                 450
```

```
TCT TTC ATG GAT GCT ATG AAT AAG TTT AAA TGG ACT AAA AAG GAA GGT    1628
Ser Phe Met Asp Ala Met Asn Lys Phe Lys Trp Thr Lys Lys Glu Gly
                455                 460                 465

CTC TCC TTC AAC AAG CTG GTC CTC AGC CTG CCA GTG AAT GTG AGA TGT    1676
Leu Ser Phe Asn Lys Leu Val Leu Ser Leu Pro Val Asn Val Arg Cys
                470                 475                 480

TCC AAG ACA GAC AAT GCT GAG TGG TCG ATT CAA GGA ATG ACA GCA TTA    1724
Ser Lys Thr Asp Asn Ala Glu Trp Ser Ile Gln Gly Met Thr Ala Leu
                485                 490                 495

CCT CCA GAT ATA GAA AGA CCC TAT AAA GCA GAA CCT TTG GTG TGT GGC    1772
Pro Pro Asp Ile Glu Arg Pro Tyr Lys Ala Glu Pro Leu Val Cys Gly
            500                 505                 510

ACG TCT TCT TCC TCT TCC CTG CAC AGA GAT TTC TCC ATC AAC TTG CTT    1820
Thr Ser Ser Ser Ser Ser Leu His Arg Asp Phe Ser Ile Asn Leu Leu
515                 520                 525                 530

GTT TGC CTT CTG CTA CTC AGC TGC ACG CTG AGC ACC AAG AGC TTG        1865
Val Cys Leu Leu Leu Leu Ser Cys Thr Leu Ser Thr Lys Ser Leu
                535                 540                 545

TGATCAAAAT TCTGTTGGAC TTGACAATGT TTTCTATGAT CTGAACCTGT CATTTGAAGT  1925

ACAGGTTAAA GACTGTGTCC ACTTTGGGCA TGAAGAGTGT GGAGACTTTT CTTCCCCATT  1985

TTCCCTCCCT CCTTTTTCCT TTCCATGTTA CATGAGAGAC ATCAATCAGG TTCTCTTCTC  2045

TTTCTTAGAA ATATCTGATG TTATATATAC ATGGTCAATA AAATAAAACT GGCCTGACTT  2105

AAGATAACCA TTTTAAAAAA TTGGGCTGTC ATGTGGGAAT AAAAGAATTC TTTCTTTCCT  2165

ACTACATTCT GTTTTATTTA AATACTCATT GTTGCTATTT CACTTTTTGA CTTGACTTTT  2225

ATATTTCTTT AAAAAATTCC TTCCTTTTAA AAAATATAAA AGGGACTACT GTTCATTCCA  2285

GTTTTCTTCT TCTTTGTTGT TCTTCTAGTG TGACTTTTCA AGTGTAACAG CCATTCTTCC  2345

TGACTTTAAT ATTGTCCAGT TCTGGTCTTT TCTGTGAATT ACCACTGGGC CCCTTACCTC  2405

AATGCTTTTT GTTGATGCCC ACTCTGGTTC CCTTGTTTAT CTGAGTCTGT TGGTACCCCA  2465

AATGACCCCA CACCCATYTT AAAGTACTTT TTTTCACCTT CCCTGTTTAG TACTGGCCAG  2525

ATGAGTTTTT TCTAGAGCTC TGTCACTATC TGAAAAGAAA GAGGCTATGG GAAACATAGA  2585

AATGGTATGT ATTAATAACT GATCATAGGC TGAGGAGAAA AAATGTAGCT GGCTGCAAAC  2645

CCAGTGCTGT GAGGTGACTT ATATGAGGTT CCAGATCAAA GACAGGCCGT GTGAGCCAGT  2705

CCAGGAGGGT GTAAGTTCTG AATGGTTCCT TGCTGACTTT GGGTGACACA TGTACCACAT  2765

ACTGGCTCAG TTTAAGTCAT GGTTCTATTG TAGATTTATT TTTATATTAG TTAATAAATG  2825

ACTTTAAATT GTCACCAATT GAAAATCTTG TCACTCTTTT GGTTTTCTTT ATATAGCTCA  2885

GCCAAATCTC TGTTTTATGT CCTGTCCTCA TCTCTTAAGC TAAATCTGTT TGGATCATAT  2945

TAATAAACCT CGTGCCGAAT TCGAT                                       2970

(2) INFORMATION FOR SEQ ID NO:15:

(i) SEQUENCE CHARACTERISTICS:
        (A) LENGTH: 545 amino acids
        (B) TYPE: amino acid
        (D) TOPOLOGY: linear (ii) MOLECULE TYPE: protein (xi) SEQUENCE DESCRIPTION: SEQ ID NO:15:

Met Asn Ser Phe Leu Ser Val Phe Arg Tyr Pro Asp Phe Ser Phe Pro
1               5                   10                  15

Tyr Phe Pro Gln Asp Tyr Phe Thr Asn Ala Asn Arg Glu Leu Lys Lys
            20                  25                  30
```

-continued

```
Asp Ala Gln Gln Asp Tyr His Leu Glu Tyr Ala Met Glu Asn Ser Thr
         35                  40                  45

His Thr Ile Ile Glu Phe Thr Arg Glu Leu His Thr Cys Asp Ile Asn
 50                  55                  60

Asp Lys Ser Ile Thr Asp Ser Thr Val Arg Val Ile Trp Ala Tyr His
 65                  70                  75                  80

His Glu Asp Ala Gly Glu Ala Gly Pro Lys Tyr His Asp Ser Asn Arg
                 85                  90                  95

Gly Thr Lys Ser Leu Arg Leu Leu Asn Pro Glu Lys Thr Ser Val Leu
            100                 105                 110

Ser Thr Ala Leu Pro Tyr Phe Asp Leu Val Asn Gln Asp Val Pro Ile
            115                 120                 125

Pro Asn Lys Asp Thr Thr Tyr Trp Cys Gln Met Phe Lys Ile Pro Val
130                 135                 140

Phe Gln Glu Lys His His Val Ile Lys Val Glu Pro Val Ile Gln Arg
145                 150                 155                 160

Gly His Glu Ser Leu Val His His Ile Leu Leu Tyr Gln Cys Ser Asn
            165                 170                 175

Asn Phe Asn Asp Ser Val Leu Glu Ser Gly His Glu Cys Tyr His Pro
            180                 185                 190

Asn Met Pro Asp Ala Phe Leu Thr Cys Glu Thr Val Ile Phe Ala Trp
            195                 200                 205

Ala Ile Gly Gly Glu Gly Phe Ser Tyr Pro Pro His Val Gly Leu Ser
            210                 215                 220

Leu Gly Thr Pro Leu Asp Pro His Tyr Val Leu Leu Glu Val His Tyr
225                 230                 235                 240

Asp Asn Pro Thr Tyr Glu Gly Leu Ile Asp Asn Ser Gly Leu Arg
            245                 250                 255

Leu Phe Tyr Thr Met Asp Ile Arg Lys Tyr Asp Ala Gly Val Ile Glu
            260                 265                 270

Ala Gly Leu Trp Val Ser Leu Phe His Thr Ile Pro Pro Gly Met Pro
            275                 280                 285

Glu Phe Gln Ser Glu Gly His Cys Thr Leu Glu Cys Leu Glu Glu Ala
            290                 295                 300

Leu Glu Ala Glu Lys Pro Ser Gly Ile His Val Phe Ala Val Leu Leu
305                 310                 315                 320

His Ala His Leu Ala Gly Arg Gly Ile Arg Leu Arg His Phe Arg Lys
            325                 330                 335

Gly Lys Glu Met Lys Leu Leu Ala Tyr Asp Asp Phe Asp Phe Asn
            340                 345                 350

Phe Gln Glu Phe Gln Tyr Leu Lys Glu Glu Gln Thr Ile Leu Pro Gly
            355                 360                 365

Asp Asn Leu Ile Thr Glu Cys Arg Tyr Asn Thr Lys Asp Arg Ala Glu
            370                 375                 380

Met Thr Trp Gly Gly Leu Ser Thr Arg Ser Glu Met Cys Leu Ser Tyr
385                 390                 395                 400

Leu Leu Tyr Tyr Pro Arg Ile Asn Leu Thr Arg Cys Ala Ser Ile Pro
            405                 410                 415

Asp Ile Met Glu Gln Leu Gln Phe Ile Gly Val Lys Glu Ile Tyr Arg
            420                 425                 430

Pro Val Thr Thr Trp Pro Phe Ile Ile Lys Ser Leu Lys Gln Tyr Lys
            435                 440                 445
```

```
Asn Leu Ser Phe Met Asp Ala Met Asn Lys Phe Lys Trp Thr Lys Lys
    450                 455                 460

Glu Gly Leu Ser Phe Asn Lys Leu Val Leu Ser Leu Pro Val Asn Val
465                 470                 475                 480

Arg Cys Ser Lys Thr Asp Asn Ala Glu Trp Ser Ile Gln Gly Met Thr
                485                 490                 495

Ala Leu Pro Pro Asp Ile Glu Arg Pro Tyr Lys Ala Glu Pro Leu Val
            500                 505                 510

Cys Gly Thr Ser Ser Ser Ser Ser Leu His Arg Asp Phe Ser Ile Asn
        515                 520                 525

Leu Leu Val Cys Leu Leu Leu Ser Cys Thr Leu Ser Thr Lys Ser
    530                 535                 540

Leu
545
```

(2) INFORMATION FOR SEQ ID NO:16:

(i) SEQUENCE CHARACTERISTICS:
  (A) LENGTH: 1635 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: -
  (B) LOCATION: 1..1635
  (D) OTHER INFORMATION: /note= "ORF of the GC6 gene"

(xi) SEQUENCE DESCRIPTION: SEQ ID NO:16:

```
ATGAATTCTT TTCTCTCTGT ATTTAGGTAT CCTGATTTTT CTTTTCCATA TTTTCCACAG    60

GATTATTTTA CAAATGCAAA TAGAGAGTTG AAAAAAGATG CTCAGCAAGA TTACCATCTA   120

GAATATGCCA TGGAAAATAG CACACACACA ATAATTGAAT TTACCAGAGA GCTGCATACA   180

TGTGACATAA ATGACAAGAG TATAACGGAT AGCACTGTGA GAGTGATCTG GCCTACCAC    240

CATGAAGATG CAGGAGAAGC TGGTCCCAAG TACCATGACT CCAATAGGGG CACCAAGAGT   300

TTGCGGTTAT TGAATCCTGA GAAAACTAGT GTGCTATCTA CAGCCTTACC ATACTTTGAT   360

CTGGTAAATC AGGACGTCCC CATCCCAAAC AAAGATACAA CATATTGGTG CCAAATGTTT   420

AAGATTCCTG TGTTCCAAGA AAAGCATCAT GTAATAAAGG TTGAGCCAGT GATACAGAGA   480

GGCCATGAGA GTCTGGTGCA CCACATCCTG CTCTATCAGT GCAGCAACAA CTTTAACGAC   540

AGCGTTCTGG AGTCCGGCCA CGAGTGCTAT CACCCCAACA TGCCCGATGC ATTCCTCACC   600

TGTGAAACTG TGATTTTTGC CTGGGCTATT GGTGGAGAGG GCTTTTCTTA TCCACCTCAT   660

GTTGGATTAT CCCTTGGCAC TCCATTAGAT CCGCATTATG TGCTCCTAGA AGTCCATTAT   720

GATAATCCCA CTTATGAGGA AGGCTTAATA GATAATTCTG GACTGAGGTT ATTTTACACA   780

ATGGATATAA GGAAATATGA TGCTGGGGTG ATTGAGGCTG CCTCTGGGT GAGCCTCTTC    840

CATACCATCC CTCCAGGGAT GCCTGAGTTC CAGTCTGAGG GTCACTGCAC TTTGGAGTGC   900

CTGGAAGAGG CTCTGGAAGC CGAAAAGCCA AGTGGAATTC ATGTGTTTGC TGTTCTTCTC   960

CATGCTCACC TGGCTGGCAG AGGCATCAGG CTGCGTCATT TTCGAAAAGG GAAGGAAATG  1020

AAATTACTTG CCTATGATGA TGATTTTGAC TTCAATTTCC AGGAGTTTCA GTATCTAAAG  1080

GAAGAACAAA CAATCTTACC AGGAGATAAC CTAATTACTG AGTGTCGCTA CAACACGAAA  1140

GATAGAGCTG AGATGACTTG GGAGGACTA AGCACCAGGA GTGAAATGTG TCTCTCATAC  1200
```

-continued

```
CTTCTTTATT ACCCAAGAAT TAATCTTACT CGATGTGCAA GTATTCCAGA CATTATGGAA    1260

CAACTTCAGT TCATTGGGGT TAAGGAGATC TACAGACCAG TCACGACCTG GCCTTTCATT    1320

ATCAAAAGTC TCAAGCAATA TAAAAACCTT TCTTTCATGG ATGCTATGAA TAAGTTTAAA    1380

TGGACTAAAA AGGAAGGTCT CTCCTTCAAC AAGCTGGTCC TCAGCCTGCC AGTGAATGTG    1440

AGATGTTCCA AGACAGACAA TGCTGAGTGG TCGATTCAAG GAATGACAGC ATTACCTCCA    1500

GATATAGAAA GACCCTATAA AGCAGAACCT TTGGTGTGTG GCACGTCTTC TTCCTCTTCC    1560

CTGCACAGAG ATTTCTCCAT CAACTTGCTT GTTTGCCTTC TGCTACTCAG CTGCACGCTG    1620

AGCACCAAGA GCTTG                                                    1635
```

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "primer KJC32"

(xi) SEQUENCE DESCRIPTION: SEQ ID NO:17:

```
AGCCGAAAAG CCAAGTG                                                    17
```

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "primer KJC33"

(xi) SEQUENCE DESCRIPTION: SEQ ID NO:18:

```
CCTCCCCAAG TCATCTCAG                                                  19
```

(2) INFORMATION FOR SEQ ID NO:19:

(i) SEQUENCE CHARACTERISTICS:
        (A) LENGTH: 1920 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 258..1868
        (D) OTHER INFORMATION: /product= "recombinant GS-GC6
            fusion protein"

(xi) SEQUENCE DESCRIPTION: SEQ ID NO:19:

```
AGCTTATCGA CTGCACGGTG CACCAATGCT TCTGGCGTCA GGCAGCCATC GGAAGCTGTG     60

GTATGGCTGT GCAGGTCGTA AATCACTGCA TAATTCGTGT CGCTCAAGGC GCACTCCCGT    120
```

-continued

```
TCTGGATAAT GTTTTTTGCG CCGACATCAT AACGGTTCTG GCAAATATTC TGAAATGAGC    180

TGTTGACAAT TAATCATCGG CTCGTATAAT GTGTGGAATT GTGAGCGGAT AACAATTTCA    240

CACAGGAAAC AGTATTC ATG TCC CCT ATA CTA GGT TAT TGG AAA ATT AAG       290
                Met Ser Pro Ile Leu Gly Tyr Trp Lys Ile Lys
                 1               5                      10

GGC CTT GTG CAA CCC ACT CGA CTT CTT TTG GAA TAT CTT GAA GAA AAA      338
Gly Leu Val Gln Pro Thr Arg Leu Leu Leu Glu Tyr Leu Glu Glu Lys
             15                  20                  25

TAT GAA GAG CAT TTG TAT GAG CGC GAT GAA GGT GAT AAA TGG CGA AAC      386
Tyr Glu Glu His Leu Tyr Glu Arg Asp Glu Gly Asp Lys Trp Arg Asn
             30                  35                  40

AAA AAG TTT GAA TTG GGT TTG GAG TTT CCC AAT CTT CCT TAT TAT ATT      434
Lys Lys Phe Glu Leu Gly Leu Glu Phe Pro Asn Leu Pro Tyr Tyr Ile
         45                  50                  55

GAT GGT GAT GTT AAA TTA ACA CAG TCT ATG GCC ATC ATA CGT TAT ATA      482
Asp Gly Asp Val Lys Leu Thr Gln Ser Met Ala Ile Ile Arg Tyr Ile
 60                  65                  70                  75

GCT GAC AAG CAC AAC ATG TTG GGT GGT TGT CCA AAA GAG CGT GCA GAG      530
Ala Asp Lys His Asn Met Leu Gly Gly Cys Pro Lys Glu Arg Ala Glu
                 80                  85                  90

ATT TCA ATG CTT GAA GGA GCG GTT TTG GAT ATT AGA TAC GGT GTT TCG      578
Ile Ser Met Leu Glu Gly Ala Val Leu Asp Ile Arg Tyr Gly Val Ser
             95                 100                 105

AGA ATT GCA TAT AGT AAA GAC TTT GAA ACT CTC AAA GTT GAT TTT CTT      626
Arg Ile Ala Tyr Ser Lys Asp Phe Glu Thr Leu Lys Val Asp Phe Leu
         110                 115                 120

AGC AAG CTA CCT GAA ATG CTG AAA ATG TTC GAA GAT CGT TTA TGT CAT      674
Ser Lys Leu Pro Glu Met Leu Lys Met Phe Glu Asp Arg Leu Cys His
     125                 130                 135

AAA ACA TAT TTA AAT GGT GAT CAT GTA ACC CAT CCT GAC TTC ATG TTG      722
Lys Thr Tyr Leu Asn Gly Asp His Val Thr His Pro Asp Phe Met Leu
140                 145                 150                 155

TAT GAC GCT CTT GAT GTT GTT TTA TAC ATG GAC CCA ATG TGC CTG GAT      770
Tyr Asp Ala Leu Asp Val Val Leu Tyr Met Asp Pro Met Cys Leu Asp
                 160                 165                 170

GCG TTC CCA AAA TTA GTT TGT TTT AAA AAA CGT ATT GAA GCT ATC CCA      818
Ala Phe Pro Lys Leu Val Cys Phe Lys Lys Arg Ile Glu Ala Ile Pro
             175                 180                 185

CAA ATT GAT AAG TAC TTG AAA TCC AGC AAG TAT ATA GCA TGG CCT TTG      866
Gln Ile Asp Lys Tyr Leu Lys Ser Ser Lys Tyr Ile Ala Trp Pro Leu
         190                 195                 200

CAG GGC TGG CAA GCC ACG TTT GGT GGT GGC GAC CAT CCT CCA AAA TCG      914
Gln Gly Trp Gln Ala Thr Phe Gly Gly Gly Asp His Pro Pro Lys Ser
     205                 210                 215

GAT CTG ATC GAA GGT CGT GGG ATC CCC AGG AAT TCG GCA CGA GAG GAT      962
Asp Leu Ile Glu Gly Arg Gly Ile Pro Arg Asn Ser Ala Arg Glu Asp
220                 225                 230                 235

TAT TTT ACA AAT GCA AAT AGA GAG TTG AAA AAA GAT GCT CAG CAA GAT     1010
Tyr Phe Thr Asn Ala Asn Arg Glu Leu Lys Lys Asp Ala Gln Gln Asp
                 240                 245                 250

TAC CAT CTA GAA TAT GCC ATG GAA AAT AGC ACA CAC ACA ATA ATT GAA     1058
Tyr His Leu Glu Tyr Ala Met Glu Asn Ser Thr His Thr Ile Ile Glu
             255                 260                 265

TTT ACC AGA GAG CTG CAT ACA TGT GAC ATA AAT GAC AAG AGT ATA ACG     1106
Phe Thr Arg Glu Leu His Thr Cys Asp Ile Asn Asp Lys Ser Ile Thr
         270                 275                 280

GAT AGC ACT GTG AGA GTG ATC TGG GCC TAC CAC CAT GAA GAT GCA GGA     1154
Asp Ser Thr Val Arg Val Ile Trp Ala Tyr His His Glu Asp Ala Gly
     285                 290                 295
```

```
GAA GCT GGT CCC AAG TAC CAT GAC TCC AAT AGG GGC ACC AAG AGT TTG      1202
Glu Ala Gly Pro Lys Tyr His Asp Ser Asn Arg Gly Thr Lys Ser Leu
300                 305                 310                 315

CGG TTA TTG AAT CCT GAG AAA ACT AGT GTG CTA TCT ACA GCC TTA CCA      1250
Arg Leu Leu Asn Pro Glu Lys Thr Ser Val Leu Ser Thr Ala Leu Pro
                320                 325                 330

TAC TTT GAT CTG GTA AAT CAG GAC GTC CCC ATC CCA AAC AAA GAT ACA      1298
Tyr Phe Asp Leu Val Asn Gln Asp Val Pro Ile Pro Asn Lys Asp Thr
            335                 340                 345

ACA TAT TGG TGC CAA ATG TTT AAG ATT CCT GTT TTC CAA GAA AAG CAT      1346
Thr Tyr Trp Cys Gln Met Phe Lys Ile Pro Val Phe Gln Glu Lys His
        350                 355                 360

CAT GTA ATA AAG GTT GAG CCA GTG ATA CAG AGA GGC CAT GAG AGT CTG      1394
His Val Ile Lys Val Glu Pro Val Ile Gln Arg Gly His Glu Ser Leu
    365                 370                 375

GTG CAC CAC ATC CTG CTC TAT CAG TGC AGC AAC AAC TTT AAC GAC AGC      1442
Val His His Ile Leu Leu Tyr Gln Cys Ser Asn Asn Phe Asn Asp Ser
380                 385                 390                 395

GTT CTG GAG TCC GGC CAC GAG TGC TAT CAC CCC AAC ATG CCC GAT GCA      1490
Val Leu Glu Ser Gly His Glu Cys Tyr His Pro Asn Met Pro Asp Ala
                400                 405                 410

TTC CTC ACC TGT GAA ACT GTG ATT TTT GCC TGG GCT ATT GGT GGA GAG      1538
Phe Leu Thr Cys Glu Thr Val Ile Phe Ala Trp Ala Ile Gly Gly Glu
            415                 420                 425

GGC TTT TCT TAT CCA CCT CAT GTT GGA TTA TCC CTT GGC ACT CCA TTA      1586
Gly Phe Ser Tyr Pro Pro His Val Gly Leu Ser Leu Gly Thr Pro Leu
        430                 435                 440

GAT CCG CAT TAT GTG CTC CTA GAA GTC CAT TAT GAT AAT CCC ACT TAT      1634
Asp Pro His Tyr Val Leu Leu Glu Val His Tyr Asp Asn Pro Thr Tyr
    445                 450                 455

GAG GAA GGC TTA ATA GAT AAT TCT GGA CTG AGG TTA TTT TAC ACA ATG      1682
Glu Glu Gly Leu Ile Asp Asn Ser Gly Leu Arg Leu Phe Tyr Thr Met
460                 465                 470                 475

GAT ATA AGG AAA TAT GAT GCT GGG GTG ATT GAG GCT GGC CTC TGG GTG      1730
Asp Ile Arg Lys Tyr Asp Ala Gly Val Ile Glu Ala Gly Leu Trp Val
                480                 485                 490

AGC CTC TTC CAT ACC ATC CCT CCA GGG ATG CCT GAG TTC CAG TCT GAG      1778
Ser Leu Phe His Thr Ile Pro Pro Gly Met Pro Glu Phe Gln Ser Glu
            495                 500                 505

GGT CAC TGC ACT TTG GAG TGC CTG GAA GAG GCT CTG GAA GCC GAA AAG      1826
Gly His Cys Thr Leu Glu Cys Leu Glu Glu Ala Leu Glu Ala Glu Lys
        510                 515                 520

CCA AGT GGA ATT CCC GGG TCG ACT CGA GCG GCC GCA TCG TGACTGACTG      1875
Pro Ser Gly Ile Pro Gly Ser Thr Arg Ala Ala Ala Ser
    525                 530                 535

ACGATCTGCC TCGCGCGTTT CGGTGATGAC GGTGAAAACC TCTGA                    1920

(2) INFORMATION FOR SEQ ID NO:20:

(i) SEQUENCE CHARACTERISTICS:
        (A) LENGTH: 536 amino acids
        (B) TYPE: amino acid
        (D) TOPOLOGY: linear (ii) MOLECULE TYPE: protein (xi) SEQUENCE DESCRIPTION: SEQ ID NO:20:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
```

```
                    20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
         50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Ile Glu Gly
            210                 215                 220
Arg Gly Ile Pro Arg Asn Ser Ala Arg Glu Asp Tyr Phe Thr Asn Ala
225                 230                 235                 240
Asn Arg Glu Leu Lys Lys Asp Ala Gln Gln Asp Tyr His Leu Glu Tyr
                245                 250                 255
Ala Met Glu Asn Ser Thr His Thr Ile Ile Glu Phe Thr Arg Glu Leu
                260                 265                 270
His Thr Cys Asp Ile Asn Asp Lys Ser Ile Thr Asp Ser Thr Val Arg
            275                 280                 285
Val Ile Trp Ala Tyr His His Glu Asp Ala Gly Glu Ala Gly Pro Lys
            290                 295                 300
Tyr His Asp Ser Asn Arg Gly Thr Lys Ser Leu Arg Leu Leu Asn Pro
305                 310                 315                 320
Glu Lys Thr Ser Val Leu Ser Thr Ala Leu Pro Tyr Phe Asp Leu Val
                325                 330                 335
Asn Gln Asp Val Pro Ile Pro Asn Lys Asp Thr Thr Tyr Trp Cys Gln
                340                 345                 350
Met Phe Lys Ile Pro Val Phe Gln Glu Lys His His Val Ile Lys Val
            355                 360                 365
Glu Pro Val Ile Gln Arg Gly His Glu Ser Leu Val His His Ile Leu
            370                 375                 380
Leu Tyr Gln Cys Ser Asn Phe Asn Asp Ser Val Leu Glu Ser Gly
385                 390                 395                 400
His Glu Cys Tyr His Pro Asn Met Pro Asp Ala Phe Leu Thr Cys Glu
                405                 410                 415
Thr Val Ile Phe Ala Trp Ala Ile Gly Gly Glu Gly Phe Ser Tyr Pro
                420                 425                 430
Pro His Val Gly Leu Ser Leu Gly Thr Pro Leu Asp Pro His Tyr Val
            435                 440                 445
```

```
Leu Leu Glu Val His Tyr Asp Asn Pro Thr Tyr Glu Glu Gly Leu Ile
    450                 455                 460
Asp Asn Ser Gly Leu Arg Leu Phe Tyr Thr Met Asp Ile Arg Lys Tyr
465                 470                 475                 480
Asp Ala Gly Val Ile Glu Ala Gly Leu Trp Val Ser Leu Phe His Thr
                485                 490                 495
Ile Pro Pro Gly Met Pro Glu Phe Gln Ser Glu Gly His Cys Thr Leu
                500                 505                 510
Glu Cys Leu Glu Glu Ala Leu Glu Ala Glu Lys Pro Ser Gly Ile Pro
        515                 520                 525
Gly Ser Thr Arg Ala Ala Ala Ser
    530                 535
```

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "primer 28SF"

(xi) SEQUENCE DESCRIPTION: SEQ ID NO:21:

GCTAAATACC GGCACGAGAC CGATAG                                      26

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "primer 28SR"

(xi) SEQUENCE DESCRIPTION: SEQ ID NO:22:

GGTTTCACGC CCTCTTGAAC TCTCTC                                      26

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC54"

(xi) SEQUENCE DESCRIPTION: SEQ ID NO:23:

GGACCTGATT CCCCAGTTGG                                                  20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC55"

(xi) SEQUENCE DESCRIPTION: SEQ ID NO:24:

AGTACTGGCC AGATGAGTTT        20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC56"

(xi) SEQUENCE DESCRIPTION: SEQ ID NO:25:

TCACACGGCC TGTCTTTGAT        20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer KJC58"

(xi) SEQUENCE DESCRIPTION: SEQ ID NO:26:

CATGCCCAAA GTGGACACAG        20

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..32
        (D) OTHER INFORMATION: /note= "primer KJC59"

(xi) SEQUENCE DESCRIPTION: SEQ ID NO:27:

GAATTCTTTT CTCTCTGTAT TTAGGTATCC TG        32

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer T7T3-pac-L"

(xi) SEQUENCE DESCRIPTION: SEQ ID NO:28:

GGCGATTAAG TTGGGTAACG                                      20

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer AB1"

(xi) SEQUENCE DESCRIPTION: SEQ ID NO:29:

GAATTGTGAG CGGATAAC                                        18

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer H15'"

(xi) SEQUENCE DESCRIPTION: SEQ ID NO:30:

GGCCTTCGTC CTCTATTTCC                                      20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer H13'"

(xi) SEQUENCE DESCRIPTION: SEQ ID NO:31:

```
GCCGTCCTCT CTGCCTCTTT                                                     20
```

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..27
        (D) OTHER INFORMATION: /note= "primer hTR445 comp"

(xi) SEQUENCE DESCRIPTION: SEQ ID NO:32:

```
GCATGTGTGA GCCGAGTCCT GGGTGCA                                             27
```

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "primer hTR S328"

(xi) SEQUENCE DESCRIPTION: SEQ ID NO:33:

```
TTGGGCTCTG TCAGCCGCGG GTCTCT                                              26
```

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer 109-5'"

(xi) SEQUENCE DESCRIPTION: SEQ ID NO:34:

```
TGCGGTCGTA TGTCAGTGAG                                                     20
```

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer 92-5'"

(xi) SEQUENCE DESCRIPTION: SEQ ID NO:35:

```
GAGAAGTCAA TGCCCATCAC                                              20

(2) INFORMATION FOR SEQ ID NO:36:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..20
         (D) OTHER INFORMATION: /note= "primer 121-5'"

(xi) SEQUENCE DESCRIPTION: SEQ ID NO:36:

TGCGGTCGTA TGTCAGTGAG                                              20
```